United States Patent [19]
Atanasoska et al.

[11] Patent Number: 5,941,843
[45] Date of Patent: Aug. 24, 1999

[54] IONTOPHORESIS ELECTRODE

[75] Inventors: Ljiljana Atanasoska, Edina; Donald Maurer, Marine on the St. Croix; Marc Stripsky, Apple Valley, all of Minn.

[73] Assignee: Empi, Inc., St. Paul, Minn.

[21] Appl. No.: 08/679,073

[22] Filed: Jul. 12, 1996

[51] Int. Cl.⁶ .................................................. A61N 1/30
[52] U.S. Cl. .............................................. 604/20; 607/152
[58] Field of Search ............................ 604/20; 607/153; 424/443; 521/25, 27, 50, 52, 54, 65

[56] References Cited

U.S. PATENT DOCUMENTS

| | | |
|---|---|---|
| 3,024,207 | 3/1962 | Shaw et al. . |
| 4,100,920 | 7/1978 | Le Goaster ............... 128/172.1 |
| 4,141,359 | 2/1979 | Jacobsen et al. ........... 128/172.1 |
| 4,164,226 | 8/1979 | Tapper ..................... 128/419 R |
| 4,166,457 | 9/1979 | Jacobsen et al. ............ 128/639 |
| 4,239,046 | 12/1980 | Ong ........................... 128/640 |
| 4,362,165 | 12/1982 | Carmon et al. ............. 128/640 |
| 4,433,481 | 2/1984 | Szpur ............................. 29/878 |
| 4,474,570 | 10/1984 | Ariura et al. ................. 604/20 |
| 4,640,689 | 2/1987 | Sibalis ........................ 604/20 |
| 4,689,039 | 8/1987 | Masaki ........................ 604/20 |
| 4,692,328 | 9/1987 | Kitchell et al. ............... 424/78 |
| 4,702,732 | 10/1987 | Powers et al. ................ 604/20 |
| 4,706,680 | 11/1987 | Keusch et al. ............. 128/640 |
| 4,708,716 | 11/1987 | Sibalis ........................ 604/20 |
| 4,715,850 | 12/1987 | Tran ............................. 604/82 |
| 4,722,726 | 2/1988 | Sanderson et al. ........... 604/20 |
| 4,725,263 | 2/1988 | McNichols et al. .......... 604/20 |
| 4,731,049 | 3/1988 | Parsi ........................... 604/20 |
| 4,731,926 | 3/1988 | Sibalis .......................... 29/877 |
| 4,752,285 | 6/1988 | Petelenz et al. .............. 604/20 |
| 4,764,164 | 8/1988 | Sasaki ......................... 604/20 |
| 4,777,954 | 10/1988 | Keusch et al. ............. 128/640 |
| 4,820,263 | 4/1989 | Spevak et al. ............... 604/20 |
| 4,842,577 | 6/1989 | Konno et al. ................. 604/20 |
| 4,856,188 | 8/1989 | Sibalis .......................... 29/877 |
| 4,915,685 | 4/1990 | Petelenz et al. .............. 604/20 |
| 4,921,475 | 5/1990 | Sibalis ........................ 604/20 |
| 4,927,408 | 5/1990 | Haak et al. .................. 604/20 |
| 4,940,056 | 7/1990 | Heck et al. ................. 128/639 |
| 4,973,303 | 11/1990 | Johnson et al. .............. 604/20 |
| 4,973,307 | 11/1990 | Theeuwes ................... 604/85 |
| 5,002,527 | 3/1991 | Reller et al. ................. 604/20 |
| 5,006,108 | 4/1991 | LaPrade ..................... 604/20 |
| 5,057,072 | 10/1991 | Phipps ........................ 604/20 |
| 5,080,646 | 1/1992 | Theeuwes et al. .......... 604/20 |
| 5,084,006 | 1/1992 | Lew et al. .................. 604/20 |
| 5,087,241 | 2/1992 | Mathiesen et al. ......... 604/20 |
| 5,087,242 | 2/1992 | Petelenz et al. ............ 604/20 |
| 5,088,978 | 2/1992 | Hillman et al. ............. 604/20 |
| 5,147,297 | 9/1992 | Myers et al. ............... 604/20 |
| 5,158,537 | 10/1992 | Haak et al. ................. 604/20 |
| 5,160,316 | 11/1992 | Henley ...................... 604/20 |
| 5,162,042 | 11/1992 | Gyory et al. ............... 604/20 |
| 5,162,043 | 11/1992 | Lew et al. .................. 604/20 |
| 5,173,302 | 12/1992 | Holmblad et al. ......... 424/448 |
| 5,225,473 | 7/1993 | Duan ......................... 524/388 |
| 5,250,023 | 10/1993 | Lee et al. ................... 604/20 |
| 5,281,287 | 1/1994 | Lloyd et al. ............... 156/80 |
| 5,288,289 | 2/1994 | Haak et al. ................. 604/20 |
| 5,310,404 | 5/1994 | Gyory et al. ............... 604/20 |

(List continued on next page.)

OTHER PUBLICATIONS

Sanderson, John E., Robert W. Caldwell, Jane Hsiao, Ross Dixon, and Ronald R. Tuttle; Noninvasive Delivery of a Novel Inotropic Catecholamine: Iontophoretic Versus Intravenous Infusion in Dogs; *Journal of Pharmaceutical Sciences*; vol. 76, No. 3; pp. 215–218; Mar. 1987.

*Primary Examiner*—Mark Bockelman
*Attorney, Agent, or Firm*—Kinney & Lange, P.A.

[57] ABSTRACT

An iontophoresis electrode that includes a buffer component formed of a first absorbent material with a pH buffering agent dispersed within or coated upon the absorbent material, a component for delivering medicament to a body where the medicament delivery component is formed of a second absorbent material and is located adjacent to and in contact with the buffer component, and an electrical connection in electrical communication with the buffer component.

37 Claims, 13 Drawing Sheets

U.S. PATENT DOCUMENTS

| | | | |
|---|---|---|---|
| 5,328,455 | 7/1994 | Llyod et al. | 604/20 |
| 5,374,241 | 12/1994 | Lloyd et al. | 604/20 |
| 5,380,272 | 1/1995 | Gross | 604/20 |
| 5,385,543 | 1/1995 | Haak et al. | 604/20 |
| 5,405,317 | 4/1995 | Myers et al. | 604/20 |
| 5,405,366 | 4/1995 | Fox et al. | 607/50 |
| 5,423,739 | 6/1995 | Phipps et al. | 604/20 |
| 5,445,609 | 8/1995 | Lattin et al. | 604/20 |
| 5,462,743 | 10/1995 | Turner et al. | 424/448 |
| 5,496,266 | 3/1996 | Haak et al. | 604/20 |
| 5,558,632 | 9/1996 | Lloyd et al. | 604/20 |
| 5,620,580 | 4/1997 | Okabe et al. | 604/20 |

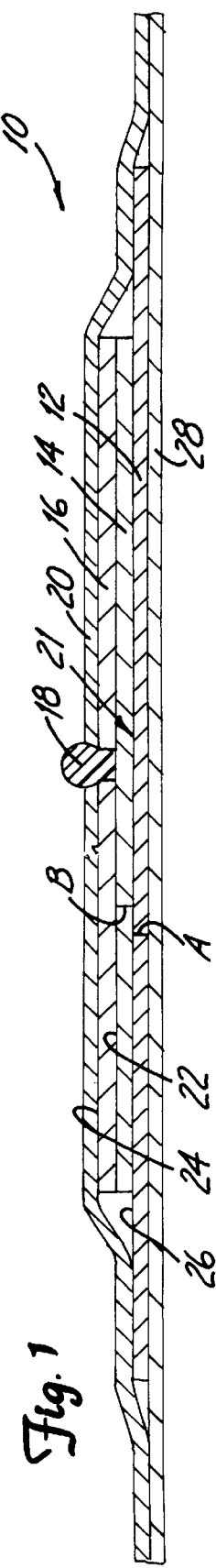
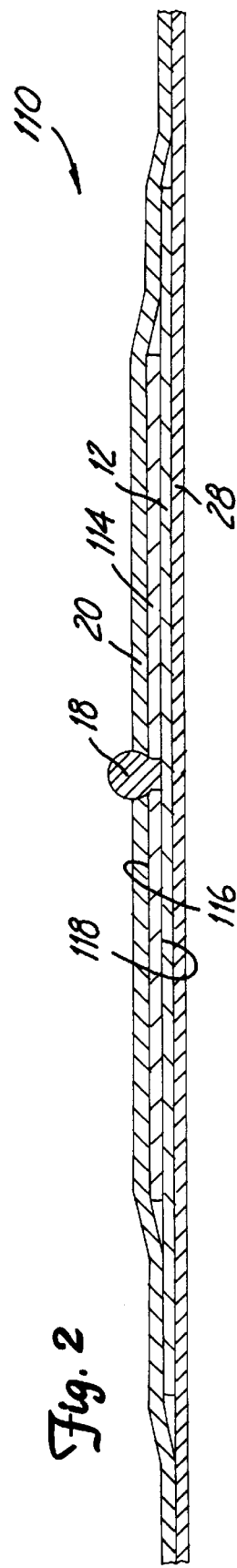
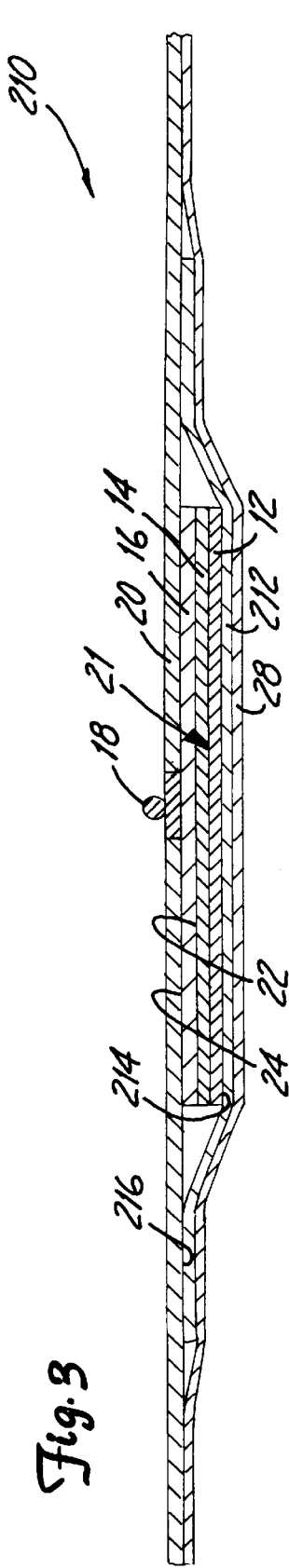
Fig. 1
Fig. 2
Fig. 3

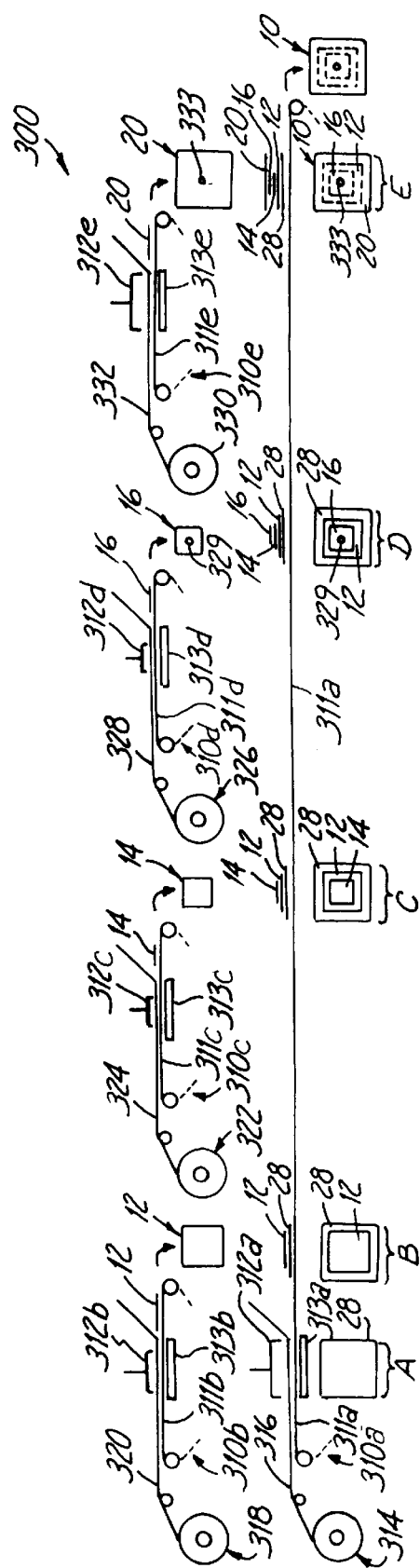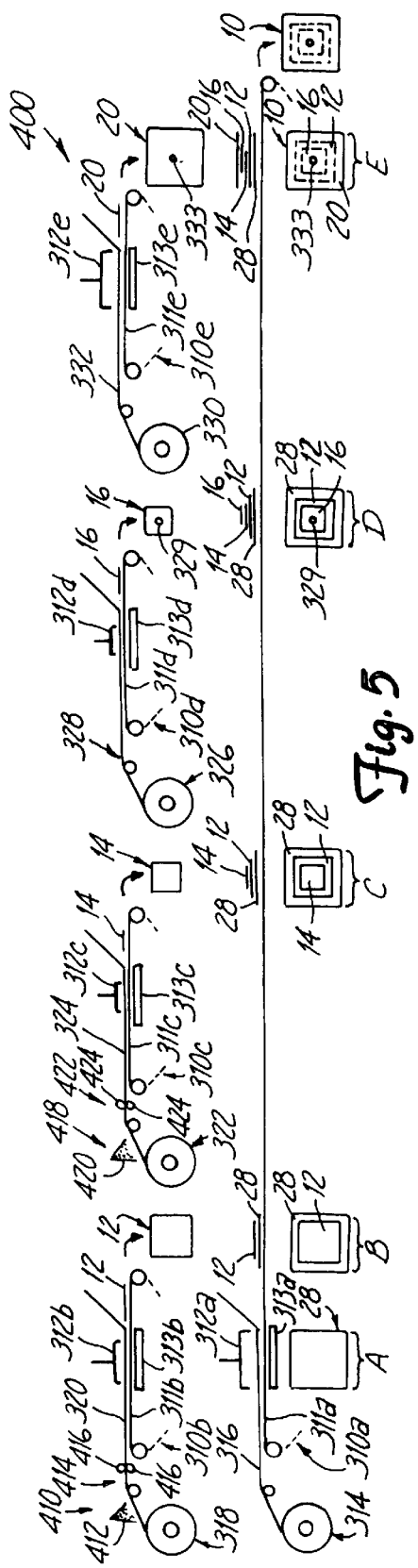

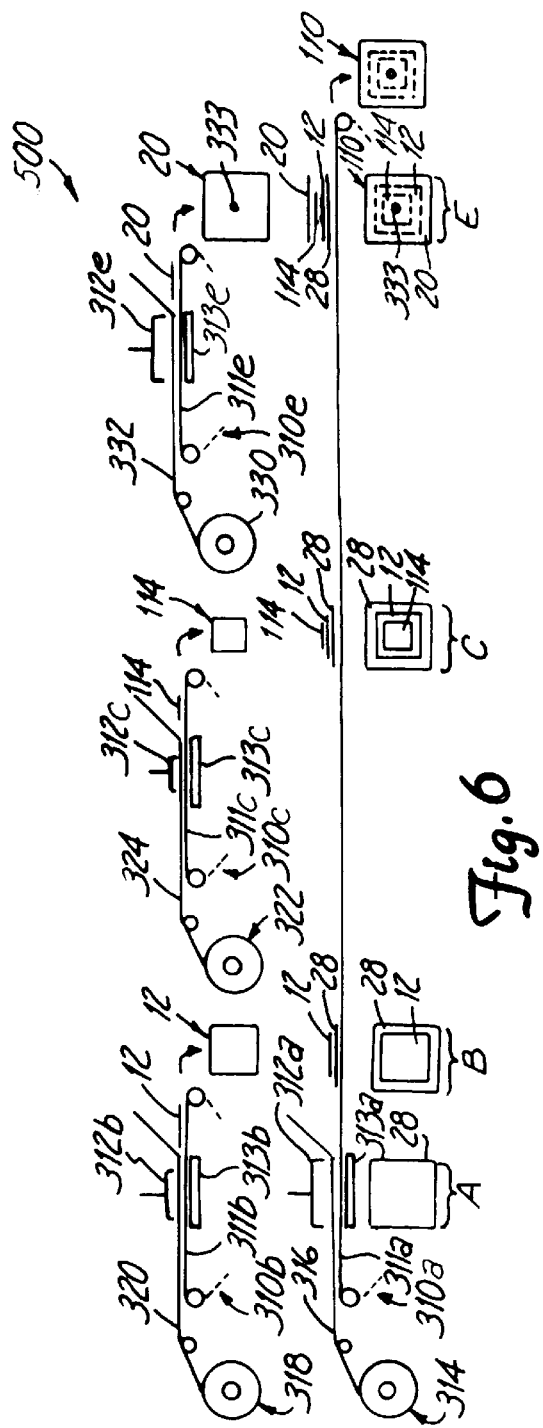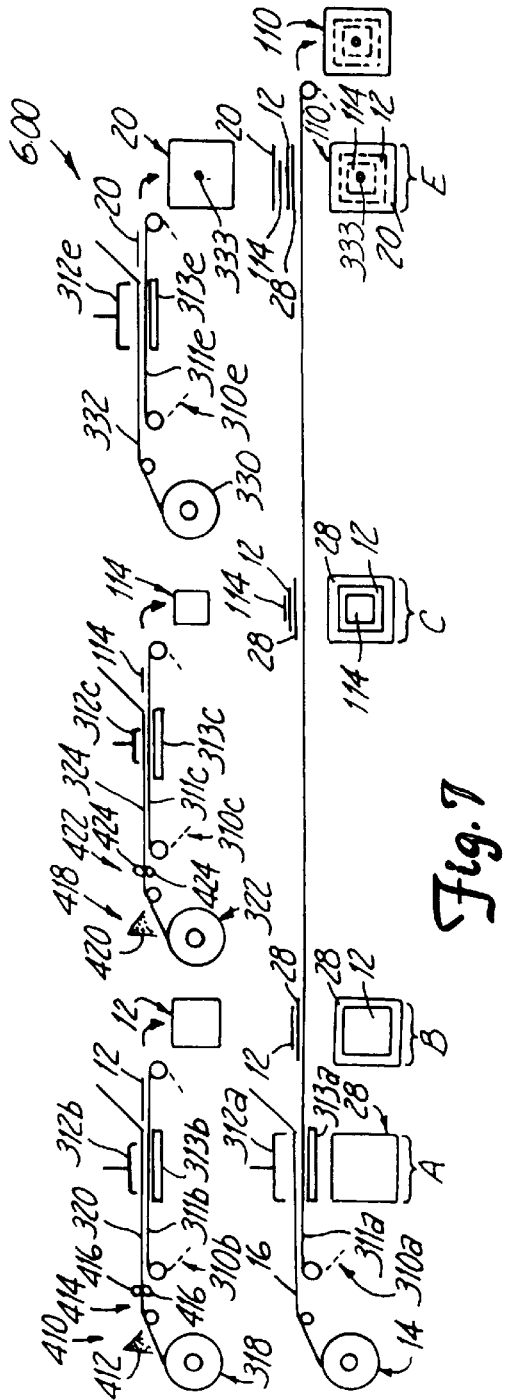

CUMULATIVE AMOUNT OF DEXAMETHASONE PHOSPHATE DELIVERED THROUGH HAIRLESS MOUSE SKIN 726 AND INTO RECEPTOR COMPARTMENT 712 PER UNIT EFFECTIVE DELIVERY AREA OF ELECTRODE ($\mu$g/cm$^2$)

CUMULATIVE AMOUNT (μg) OF PROTONATED LIDOCAINE DELIVERED THROUGH HAIRLESS MOUSE SKIN 726 AND INTO RECEPTOR COMPARTMENT 712

CUMULATIVE AMOUNT OF PROTONATED LIDOCAINE DELIVERED THROUGH HAIRLESS MOUSE SKIN 726 AND INTO RECEPTOR COMPARTMENT 712 PER UNIT EFFECTIVE DELIVERY AREA OF ELECTRODE ($\mu g/cm^2$)

CUMULATIVE AMOUNT (μg) OF MINOXIDIL IONS DELIVERED THROUGH HAIRLESS MOUSE SKIN 726 AND INTO RECEPTOR COMPARTMENT 712

CUMULATIVE AMOUNT OF MINOXIDIL IONS DELIVERED THROUGH HAIRLESS MOUSE SKIN 726 AND INTO RECEPTOR COMPARTMENT 712 PER UNIT EFFECTIVE DELIVERY AREA OF ELECTRODE ($\mu$g/cm$^2$)

IONTOPHORESIS ELECTRODE

BACKGROUND OF THE INVENTION

The present invention generally relates to an apparatus for transdermally delivering medicament ions derived from ionic substances, such as drugs or other therapeutic chemicals, into a body. More particularly, the present invention relates to an apparatus for iontophoretically introducing medicament ions into the body.

Iontophoresis may be generally described as a method of transdermally introducing medicament ions into a body. The iontophoresis process utilizes current developed by an electric field to drive medicament ions through the skin, or other biological surface, and into the body. The iontophoresis process has been found to be particularly useful in transdermal administration of medicament ions, such as charged organic medications and therapeutic metal ions.

Iontophoresis permits introduction of medicament ions directly into a patient's tissues and blood stream without the need for a needle-based injection, which typically causes pain and may create a risk of infection. Iontophoretic delivery of medicament ions also avoids premature metabolism of medicament ions that typically occurs when drugs are taken orally. Premature metabolism is of concern because medicament ions derived from drugs that are taken orally are absorbed into the blood stream from the digestive system. The blood containing the medicament ions then percolates through the liver, where the medicament ions may be prematurely metabolized, before the medicament ions arrive at the target tissue. Thus, a substantial amount of the medicament ions derived from an orally administered drug may be metabolically inactivated before the medicament ions have a chance to pharmacologically act in the body.

A typical iontophoresis device includes two electrodes. One of the electrodes is often characterized as an "active" electrode, and the other electrode is often characterized as a "return" electrode. Also, one of the electrodes is a positively charged anode and the other electrode is a negatively charged cathode. Both electrodes are in intimate electrical contact with the skin or other biological surface of the body, which may be a human body or another type of body, such as an animal body. Application of electric current to the active electrode drives the medicament ion, such as the charged organic medication, from the active electrode into the body. The other electrode, the return electrode, closes the electrical circuit to permit current flow through the active electrode and through the body.

In some cases, medicament ions may be delivered to the body from both electrodes of the iontophoresis system. In such cases, a first electrode is the active electrode for a first medicament ion that is delivered from the first electrode, and a second electrode is the return electrode with respect to the first medicament ion. Similarly, the second electrode is the active electrode for a second medicament ion that is delivered from the second electrode, and the first electrode is the return electrode with respect to the second medicament ion. The first and second medicament ions are typically different in polarity and in chemical structure from each other.

Though iontophoresis system technology has realized several advances, numerous problems remain to be solved and many opportunities for enhancing performance remain. The process of iontophoretic drug delivery may be accomplished using very simple electrodes. However, the use of more sophisticated electrode configurations is needed to solve problems that are not addressed by simple electrode systems and to realize enhanced performance characteristics. Examples of some suggested approaches for optimizing iontophoresis systems are included in U.S. Pat. Nos. 4,731,049 to Parsi; 4,915,685 to Petelenz et al.; and 5,302,172 to Sage, Jr. et al. The Parsi patent suggests a change in the iontophoresis systems that is said to increase the types of drugs deliverable by iontophoresis systems. The Petelenz patent suggests changes that are said to enhance the proportional relationship between the amount of medicament ions administered and current flow. Finally, the Sage, Jr. patent discloses the use of vasodilators in iontophoresis as a means of enhancing delivery of an active agent that is delivered along with vasodilator.

Despite the many advances in iontophoresis technology, a series of problems remain that relate to electrolysis of water in iontophoresis system electrodes. As an example, current passing through the electrodes of an iontophoresis system typically cause electrolysis of water in the electrodes. In the anode, the electrolysis reaction proceeds as follows:

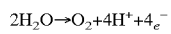

In the cathode, the electrolysis reaction proceeds as follows:

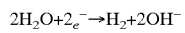

Since an operational iontophoresis system includes both an anode and a cathode, both hydrogen ions ($H^+$) and hydroxide ions ($OH^-$) are produced if electrolysis of water occurs during system operation. Absent buffering of the electrolysis products, the hydrogen ion concentration will increase at the anode and the hydroxide ion concentration will increase at the cathode.

Hydrogen ion and hydroxide ion accumulation in the electrodes of iontophoresis systems is problematic for a variety of reasons. For example, the increased hydrogen ion concentration shifts the pH downward at the anode, and the increased hydroxide ion concentration shifts the pH upward at the cathode. The pH shift typically causes at least minor skin irritation and can cause severe burning of a patient's skin, if left uncontrolled. Also, the pH shift can change the activity of the medicament ion(s) being delivered by the electrode, can significantly reduce the rate of medicament ion delivery by the electrode, and can even degrade the physical properties of the electrode components.

One technique for controlling the pH shift involves the introduction of one or more buffering species into the iontophoretic electrodes. The buffering species may be in solution with the solution of the medicament ion to be delivered in the medicament delivery portion of the electrode. However, when the buffering species is in solution with the medicament ion in the medicament delivery portion of the electrode, experience has shown that the buffering species and derivatives of the buffering species undesirably compete with medicament ions for delivery to the target body.

Another technique for incorporating buffering species in iontophoresis electrodes is disclosed in U.S. Pat. No. 4,973,303 to Johnson et al. Though there are benefits to the technique disclosed in the Johnson patent, it has been found that the amount of ion-exchange functionality included in the buffer of the Johnson electrode cannot be accurately controlled. Furthermore, the Johnson technique uses several times more buffering agent than is chemically required to buffer water electrolysis products.

Though many advances in iontophoretic electrode design and operation have been realized, challenges requiring solutions remain. For example, less complicated and more accurate techniques are needed for controlling the amount of buffering species included in iontophoresis electrodes. Also, opportunities remain for enhancing the rate of medicament ion delivery by iontophoresis electrodes. Finally, opportunities remain for simplifying electrode manufacturing techniques and automating the iontophoresis electrode manufacture.

SUMMARY OF THE INVENTION

The present invention includes an iontophoresis electrode with a buffer component, a component for delivering medicament ions to a body, and an electrical connection in electrical communication with the buffer component. The buffer component is formed of a first absorbent material and includes a pH buffering agent that is dispersed within or coated upon the absorbent material. The medicament delivery component is formed of a second absorbent material and is located adjacent to and in contact with the buffer component.

BRIEF DESCRIPTION OF THE DRAWINGS

FIG. 1 is a sectional view of a pH buffered electrode of the present invention.

FIG. 2 is a sectional view of another pH buffered electrode of the present invention.

FIG. 3 is a sectional view of another pH buffered electrode of the present invention.

FIG. 4 is a schematic view of an apparatus for manufacturing the pH buffered electrode of the present invention.

FIG. 5 is a schematic view of another apparatus for manufacturing the pH buffered electrode of the present invention.

FIG. 6 is a schematic view of another apparatus for manufacturing the pH buffered electrode of the present invention.

FIG. 7 is a schematic view of another apparatus for manufacturing the pH buffered electrode of the present invention.

DETAILED DESCRIPTION OF THE PREFERRED EMBODIMENTS

Figure 8:
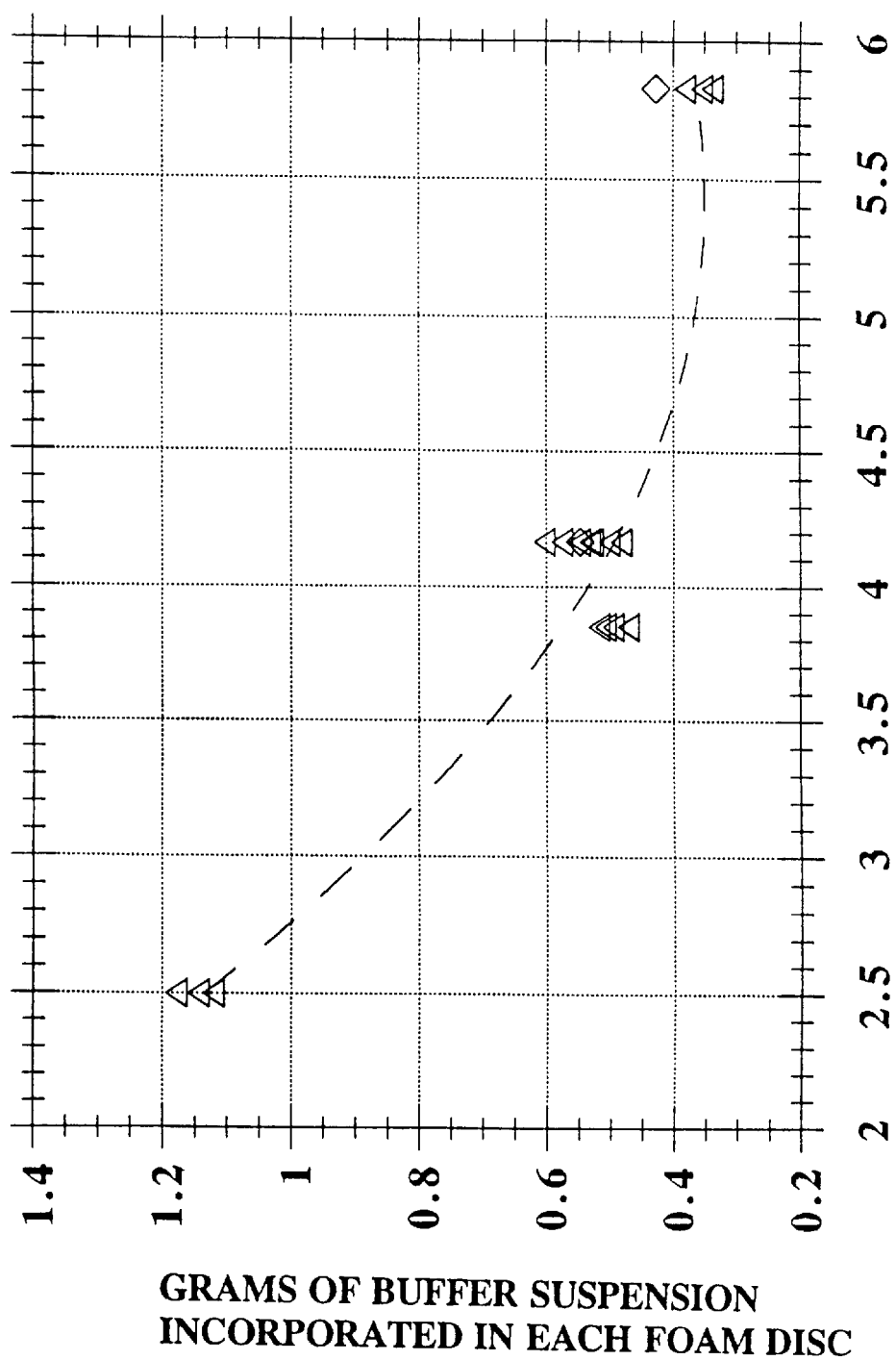
FIG. 8 is a graphical representation of the amount of buffer suspension incorporated in a buffer component of the present invention versus the weight ratio of glycerine to buffering resin in the buffer suspension.

An iontophoresis electrode of the present invention for delivering medicament ions to a body is generally depicted at 10 in FIG. 1. The electrode 10 includes a medicament delivery component 12 and a buffer component 14. The buffer component 14 is located adjacent to and in direct contact with the medicament delivery component 12. pH buffering agent is preferably dispersed uniformly throughout the buffer component 14. However, a buffer coating that includes the pH buffering agent may alternatively be applied to an outer surface of the component 14. The electrode 10 further includes a conductive component 16 that is located adjacent to and in contact with the buffer component 14. The buffer component 14 is thus located between the medicament delivery component 12 and the conductive component 16.

The electrode 10 additionally includes a conductive tab or terminal 18, such as a conductive snap connector, that is attached in electrical communication to the conductive component 16. The terminal 18 couples the electrode 10 to a source of electrical power (not shown), such as a source of direct current. The electrode 10 also incorporates an adhesive covering 20 that serves as a structural support component of the electrode 10 and is also useful for securing the electrode 10 to the skin (not shown).

The medicament delivery component 12 and the buffer component 14 are each made of absorbent material that is capable of quickly absorbing an electrolytic solution and maintaining the electrolytic solution as a confluent liquid phase within the absorbent material. The absorbent material of the components 12, 14 should be capable of being fully wetted by the electrolytic solution. The electrolytic solution includes conductive ions and a solvent that is capable of maintaining the conductive ions in solution. Some examples of the solvent include (1) water and (2) a mixture of water and an organic liquid such as an alcohol, depending upon the solubility of the conductive ions. The electrolytic solution may either include medicament ions and complimentary ions of the medicament ions or may be free of medicament ions and the complimentary ions.

The absorbent material of the buffer component 14 preferably incorporates pH buffering agent that is distributed or dispersed in substantially uniform fashion throughout the absorbent material. The pH buffering agent may be an ion exchange substance, such as ion-exchange resin, that is capable of buffering water electrolysis products produced during operation of the electrode 10 to maintain the pH of the electrolytic solution within a range of about 4 to about 8 standard pH units. Alternatively, the absorbent material of the buffer component 14 may include the buffer coating to incorporate the pH buffering agent as part of the buffer component 14. No matter how the buffer component 14 incorporates the pH buffering agent, the pH buffering agent should be immobilized to prevent, or predominantly prevent, the pH buffering agent from interfering with medicament ions that are located in the medicament delivery component 12.

A major benefit of the electrode 10 is the opportunity that the structure of the electrode 10 affords for separating the pH buffering agent from the medicament delivery component 12. This separation permits simultaneous medicament ion delivery to the body by the medicament delivery component and buffering of water electrolysis products by the pH buffering agent, while avoiding any deleterious impact by the pH buffering agent on medicament ion delivery by the component 12.

Electrolytic solution that contains medicament ions and complimentary ions of the medicament ions may be held in both the medicament delivery component 12 and the buffer component 14. In the experience of the inventors, the presence of medicament ions and complimentary ions in the buffer component 14 does not degrade the rate of medicament ion delivery to the body by the component 12. Medicament ions present in the medicament delivery component 12 are delivered to the body at the same rate, regardless of medicament ions being present or absent in the component 14. Therefore, there is no need for the electrode 10 to include any sort of barrier, such as a semi-permeable membrane or an ion exchange membrane, to prevent medicament ion and complimentary ion entry into the buffer member 14 from the medicament delivery component 12. This absence of any such barrier to medicament ion movement into the buffer component 14 from the medicament ion delivery component 12 simplifies both the structure and the manufacture of the electrode 10.

Though the component 12 and the component 14 are located adjacent to each other and are in direct contact with each other, there should be a distinct interface 21 or boundary between the absorbent material of the component 12 and the absorbent material of the component 14 to insure adequate separation of the pH buffering agent from the medicament delivery component 12. The interface 21 should exist throughout the life of the electrode 10 to insure lifetime optimum performance of the electrode 10. The interface 21 is preferably smooth in nature. The absorbent material of the component 12 and the absorbent material of the component 14 should not merge with each other to any degree at the interface 21 between the components 12, 14, but should instead be distinct from each other. The smooth nature of the boundary 21 helps maintain the components 12, 14 as distinct, separate components that cooperate with each other through the direct contact.

It is believed that medicament ion delivery by the component 12 will tend to decrease as the pH buffering agent increasingly interferes with medicament ions that are present in the component 12. Thus, the pH buffering agent should not be incorporated into the component 12, since it is believed that pH buffering agent that is incorporated in the component 12 would at least substantially interfere with medicament ion movement within the component 12 and with medicament ion delivery by the component 12 to the body. Furthermore, the distinct interface 21 between the component 12 and the component 14 should remain during the life of the electrode 10 to minimize interference of the pH buffering agent that is located in the buffer component 14 with medicament ions that are present in, and delivered to the body by, the medicament delivery component 12.

It is believed that pH buffering agent interference with medicament ion movement and delivery results from electro-migration and diffusion phenomena that arise during iontophoresis. These electro-migration and diffusion phenomena are believed to arise whenever pH buffering agent is located between the body and medicament ions to be delivered to the body. This explains why the pH buffering agent should not be included as part of the component 12, but should instead be located outside of the component 12 so that the component 12 is located between the body and the pH buffering agent. At least some of the electro-migration and diffusion phenomena are also believed to exist whenever medicament ions and pH buffering agent are located adjacent to each other and at about the same distance from the body. This is why the distinct interface 21, which is preferably smooth, should exist between the component 12 and the component 14.

Though medicament ions will typically be present in the buffer component 14, in addition to the medicament delivery component 12, it is believed that predominantly all of the medicament ions that are delivered to the body are delivered by the medicament delivery component 12. That is why the component 12 is designated as the medicament delivery component 12. It is believed that less than about 10 weight percent, and possibly less than about 5 weight percent, of the medicament ions that are delivered to the body are delivered by the buffer component 14. This discrepancy between medicament ion delivery by the component 12 versus medicament ion delivery by the component 14 is believed due to the interference of the pH buffering agent of the component 14 with medicament ions that are located in the buffer component 14.

The electrode 10 exhibits greatly improved medicament ion delivery flux, as compared to existing iontophoresis electrodes, despite interference of pH buffering agent with medicament ions that are located in the buffer component 14. The inventive placement of the medicament delivery component 12 between the pH buffering agent and the body effectively isolates the pH buffering agent from medicament ions that are located in and are delivered by the component 12. Thus, the delivery flux of medicament ions that originate in the medicament delivery component 12 is unfettered by the pH buffering agent and is many times greater than the delivery flux of medicament ions that originate in the buffer component 14. Due to isolation of the pH buffering agent away from the component 12 and the presence of the distinct interface 21 during the life of the electrode 10, improved medicament delivery flux is therefore attained by the electrode 10, while retaining the highly desirable buffering capabilities of the pH buffering agent.

The size and resultant medicament ion capacity of the medicament delivery component 12 should compensate for the relatively low medicament ion efficiency of the buffer component 14 for delivering medicament ions to the component 12 from the component 14. This compensation is needed because the medicament ion delivery efficiency and rate of the buffer component 14 is substantially lower than the medicament ion delivery efficiency and rate of the component 12, regardless of whether or not the components 12 and 14 are of similar size and medicament ion holding capacity.

Any substance that is to be iontophoretically delivered to the body exists as medicament ions. The electrolytic solution that is included in the medicament delivery component 12 and the buffer component 14 may include one or more different types of medicament ions. The term "medicament ion" is intended to have the broadest possible interpretation to encompass any therapeutically active ionic substance that is deliverable to a living body to produce a desired beneficial effect.

The electrode 10 may be used to deliver medicament ions through any biological surface of any living organism. The term "living organism" includes, but is not limited to, living bodies of human beings and animals. The term "biological surface", as used herein, is defined to include, without limitation, skin, mucosal membranes, nails, blood vessel walls, and all other biological surfaces of any living organism. It will be appreciated that transportation of medicament ions through the biological surface of a living organism may take place in the presence of an electrical field, such as that produced in an iontophoresis system that includes a pair of electrodes, as well as, a source of electrical current.

All references to "body" in the specification, drawings, and claims of this document are to be understood as referring to any living organism that is capable of being treated by iontophoresis. All references to "skin" in the specification, drawings, and claims of this document are to be understood as referring to any biological surface that is capable of transmitting medicament ions delivered to the biological surface by iontophoresis.

The medicament ions that are present in any electrolytic solution which is contained in the medicament delivery component 12 and the buffer component 14 may be derived from any suitable therapeutically active ionic substance. The ionic substance may be any suitable salt, acid, or base that dissociates into medicament ions and complimentary ions of the medicament ions in the electrolytic solution. Medications, drugs, and other therapeutic chemicals are some general examples of suitable ionic substances.

Some examples of the types of therapeutically active ionic substances that may evolve medicament ions in any electrolytic solution of the medicament delivery component 12 and the buffer component 14 include, but are not limited to, a variety of ACE inhibitors, analgesics, anorexics, antiarthritics, antiasthmatic agents, antibiotics, antibodies, antidiabetic agents, antidiarrheals, antidepressants, antihistamines, anti-inflammatory agents, anti-migraine preparations, anti-motion sickness preparations, anti-nauseants, antineoplastics, antiparkinsonism drugs, antipruritics, antipsychotics, antipyretics, antispasmatics, antiviral agents, antiocholinergics, antiarrythmics, antihypertensives, anesthetics, beta-agonists, cardiovascular preparations, central nervous system stimulants, cough and cold preparations, decongestants, diagnostics, diuretics, enzymes, hormones, hypnotics, immunosuppressives, muscle relaxants, parasympatholytics, parasympathomimetrics, prostaglandins, proteins, peptides, psychostimulants, sedatives, steroids, sympathomimetrics, tranquilizers, vasodilators, vitamins, and xanthine derivatives.

Some examples of particular ionic substances that may evolve medicament ions in any electrolytic solution of the components 12, 14 include, but are not limited to, morphine sulfate, dexamethasone sodium phosphate, hydrocortisone derivatives, lidocaine hydrochloride, morphine hydrochloride, penicillin, minoxidil tartrate, nitroglycerine, acetic acid, fluoride, and magnesium chloride.

Medicament ions formed on dissociation of ionic substances are desirable ions that are intended for delivery into the body via the biological surface. Complimentary ions formed on dissociation of ionic substances are ions that are not intended for delivery into the body. Aside from complimentary ions, other ions that are not intended for delivery into the body are subsequently referred to as adverse ions.

Though electrolytic solution included in some iontophoresis system electrodes, or electrode components, may not include medicament ions, the electrolytic solution included in these iontophoresis system electrodes, or electrode components, should nevertheless include suitable conductive ions. The conductive ions are needed to support current flow through the iontophoresis system. The conductive ions should be selected so that any conductive ions that are delivered into the body during iontophoresis do not cause deleterious effects within the body. The solvent of the electrolytic solution that is included in any electrode of the iontophoresis system may be any solvent, such as water, that suitably solubilizes medicament ions or conductive ions that are included in the electrolytic solution. The solvent of the electrolytic solution should be selected to avoid any harmful effects to the body.

An iontophoresis system (not shown) typically includes two electrodes (not shown) that are in electrical contact with the skin of the body. Either or both of the electrodes of the iontophoresis system may have the structure of the electrode 10. One of the electrodes of the iontophoresis system may be characterized as an "active" electrode of the system and the other electrode may be characterized as a "return" electrode of the system. One of the electrodes of the iontophoresis system also serves as a positively charged anode and the other electrode is a negatively charged cathode. When one of the electrodes delivers medicament ions into the body, the electrode delivering the medicament ions is the active electrode and the other electrode, the return electrode, completes the electrical circuit through the body between the active electrode and the return electrode.

When the anode of the iontophoresis system has the structure of the electrode 10, electrolytic solution is included in both the component 12 and the component 14 to support current flow from the terminal 18 through the component 16, the component 14, and the component 12, and into the body. The electrode 10 that serves as the anode may be either the active electrode for delivering medicament ions into the body or may be the return electrode. When the cathode of the iontophoresis system has the structure of the electrode 10, electrolytic solution is included in both the component 12 and the component 14 to support current flow from the body, through the component 12, the component 14, and the component 16, and into the terminal 18. The electrode 10 that serves as the cathode may be either the active electrode for delivering medicament ions into the body or may be the return electrode.

Also, as explained below, the anode and the cathode that have the structure of the electrode 10 may each serve as both active and return electrodes when medicament ions are delivered from both the anode and the cathode. Those skilled in the art will readily recognize that in any electrode 10 serving only as the return electrode, and not serving at any time during the treatment session as the active electrode, the component 12 is provided only for purposes of helping to complete the electrical circuit through the body, or for purposes of performing reverse iontophoresis (removing ions from the body), and not for purposes of delivering medicament ions to the body.

The component 12 and the component 14 may generally consist of any absorbent material, or mixture of absorbent materials, that is capable of absorbing and holding the electrolytic solution, including solutions that include medicament ions and solutions that do not include medicament ions. The particular absorbent material(s) used to form the component 12 may generally be the same as, or different from, the absorbent material(s) that are used to form the component 14. However, the buffer component 14 will always be different from the medicament delivery component 12, since the absorbent material of the buffer component 14 will be coated with the buffer coating or will otherwise incorporate pH buffering agent, whereas pH buffering agent will never be coated on or incorporated into the absorbent material of the component 12.

The absorbent material(s) of the components 12, 14 should be capable of being fully wetted by the electrolytic solution and should be capable of holding the electrolytic solution as a confluent liquid phase that is uniformly distributed throughout the absorbent material(s). The absorbent material should also be capable of quickly absorbing the electrolytic solution. Since the bulk of the medicament ion delivery from the electrode 10 involves medicament ions that originate in the component 12, the component 12 should be sized to contain at least enough medicament ions, at the selected medicament ion concentration in the electrolytic solution, for one session of patient treatment. In one embodiment of the electrode 10, the component 12 is sized to contain about 5.5 ml of the electrolytic solution of medicament ions.

The electrolytic solution may be introduced into the electrode 10 by any conventional technique, such as by injecting electrolytic solution into the component 12 or the component 14 with a hypodermic needle. Since the components 12 and 14 are in contact with each other and are each made of absorbent material that is capable of absorbing the electrolytic solution, the electrolytic solution will be absorbed into both the component 12 and the component 14, no matter which of the components 12, 14 the electrolytic solution is injected into. The components 12, 14 may hold electrolytic solution that either does or does not contain medicament ions both prior to and during delivery of medicament ions into the body.

The medicament delivery component 12 and the buffer component 14 may each be multi-layered. However, the medicament delivery component 12 is preferably formed as a single, monolithic layer, and the buffer component 14 is preferably formed as a single, monolithic layer. Formation of the components 12, 14 as single monolithic layers simplifies the structure and manufacture of the electrode 10 and the components 12, 14, while maintaining performance benefits of the electrode 10, such as enhanced buffering uniformity.

The layer or layers of the medicament delivery component 12 and the buffer component 14 may generally be made of any absorbent material, or mixture of absorbent materials, that has suitable absorbent characteristics and is capable of supporting the electrolytic solution as a confluent liquid phase, so long as the distinct interface 21 is maintained between the component 12 and the component 14. When the medicament delivery component 12 is multi-layered, different absorbent materials may be used to form different layers of the component 12. Likewise, when the buffer component 14 is multi-layered, different absorbent materials may be used to form different layers of the component 14. Additionally, the component 12 and the component 14 may be formed of different absorbent materials.

The absorbent material of the medicament delivery component 12 and the buffer component 14 may generally be based on any synthetic or natural resinous material, such as a gum, polyurethane, or polyvinyl alcohol; any natural or synthetic fibrous material, such as polyester, rayon, wool, cotton, or cellulose; any colloidal material, such as that used to form gels, or any mixture of these, so long as the distinct interface 21 is maintained between the component 12 and the component 14. The resinous material may generally be any resinous polymer or copolymer or a mixture of resinous polymers or copolymers. The absorbent material that is used to make the components 12, 14 may generally have any solid or semi-solid form, such as that of foam, woven fabric, or gel. No matter what physical form the absorbent material takes, each form of the absorbent material should be capable of quickly absorbing the electrolytic solution and maintaining the electrolytic solution as a confluent liquid phase within the absorbent material.

As used herein, a solid or semi-solid "foam" is a colloid that includes (1) a solid or-semisolid continuous phase that forms a three dimensional network and, prior to incorporation of electrolytic solution, (2) a dispersed gaseous phase throughout the three dimensional network of the continuous phase. The continuous phase of the foam may be formed using either synthetic polymeric substances, such as polyurethane, or naturally occurring polymeric substances, such as natural rubber. As used herein, a "gel" is defined as a lyophilic colloid that has coagulated to form either a rigid or a jelly-like solid. The colloid of the gel includes a continuous phase that forms a three dimensional network and a disperse phase that forms a loosely-held network of linked molecules throughout the three dimensional network of the continuous phase. Gelatin is one example of a gel. As used herein, a "gum" is defined as any of a variety of natural occurring substances obtained from plants, or synthetic equivalents of these naturally occurring substances, that are insoluble in organic solvents and form gelatinous or sticky solid or semi-solid solutions with water. Colloidal polysaccharide substances are examples of gums.

The absorbent material of the components 12, 14, preferably takes the form of open cell solid foam that supports enhanced movement of any medicament ions included in the electrolytic solution. Open cell solid foam is more easily incorporated into automated manufacturing processes for making the electrode 10 than other materials. Additionally, the interconnection of pores and pore size range and distribution of open cell solid foams support enhanced, movement of medicament ions included in the electrolytic solution. The open cell solid foam is preferably open cell polyurethane foam.

The polyurethane foam used to form the medicament delivery component 12 preferably has an average pore density ranging from about 5 to about 200 pores per linear inch (ppi) of polyurethane foam surface and an average pore diameter ranging from approximately 150 micrometers to approximately 1,000 micrometers. Polyurethane foams with these pore density and diameter characteristics are available as the RYNEL® series of polyurethane foams, such as AMREL™ 6 polyurethane foam, that may be obtained from Rynel, Ltd., Inc. of Boothbay, Me. Polyvinyl alcohol foam with these pore density and diameter characteristics is available as KANEBO® polyvinyl alcohol foam that may be obtained from Shima American Corporation of Elmhurst, Ill.

The polyurethane foam used to form the buffer component 14 preferably has an average pore density of about 70 to about 80 pores per linear inch (ppi) of polyurethane foam surface and an average pore diameter ranging from about 200 micrometers to about 240 micrometers. Polyurethane foam with these pore density and diameter characteristics may be obtained as PREMIUM polyurethane foam from Foamex of Eddystone, Pa. or as FILTERCREST® polyurethane foam from Crest Foam Industries of Moonachie, N.J.

Though the absorbent material of the components 12, 14 preferably takes the form of monolithic layers, the absorbent material may alternatively consist of loose material, such as resinous particles or granules. When the absorbent material of the component 12 is loose material, the medicament delivery component 12 should include suitable containment layers (not shown) for containing the absorbent material within the medicament delivery component 12. When the absorbent material of the component 14 is loose material, the buffer component 14 should include suitable containment layers (not shown) for containing the absorbent material within the buffer component 14.

The absorbent material(s) that are used to form the medicament delivery component 12 and the buffer component 14 should be highly absorbent, should have a relatively large specific absorbency, and should absorb the electrolytic solution at a relatively high rate. High absorbency is needed so that the surface area and weight of the components 12, 14, and the dimensions and weight of the electrode 10 can be minimized without sacrificing the quantity of any medicament ions that are delivered by the electrode 10. The absorbent material(s) need to have a relatively high rate of absorption so that the electrolytic solution may be quickly placed in the medicament delivery component 12 and the buffer component 14. The relatively high rate of absorption also minimizes or eliminates losses of electrolytic solution and any medicament ions from the electrode 10 during incorporation of the electrolytic solution into the components 12, 14.

The absorbent material(s) of the components 12, 14 should be capable of absorbing at least about 500 ml of electrolytic solution per square meter of absorbent surface within about 5 seconds or less. Preferably, the absorbent material(s) should be capable of absorbing at least about 1,000 ml of electrolytic solution per square meter of absorbent material surface within about 5 seconds or less. More preferably, the absorbent material should be capable of absorbing at least about 2,000 ml of electrolytic solution per square meter of absorbent material surface within about 5 seconds or less. Still more preferably, the absorbent material should be capable of absorbing at least about 3,500 to about 4,000 ml of electrolytic solution per square meter of absorbent material surface within about 5 seconds or less.

For purposes of determining absorbency, the surface area of the absorbent material is determined after the absorbent material has been formed into the component 12 layer(s) and the component 14 layer(s). Each layer of the component 12 and each layer of the component 14 will have major surfaces and minor surfaces. A thickness A of each layer of the component 12 and a thickness B of each layer of the component 14 will typically be orders of magnitude less than the length, the width, the diameter, or other major dimension of the component 12 or component 14 layers. The minor surfaces of the layers are defined as those surfaces that encompass the thickness A or B of the layers, and the major surfaces are defined as those surfaces that do not encompass the thickness A or B of the layers.

The absorbency of the absorbent material(s) may be determined by applying the electrolytic solution to any major surface of any absorbent material layer of the component 12 and to any major surface of any absorbent material layer of the component 14. The surface area of any layer of absorbent material, for purposes of evaluating absorbency, is the surface area of the major surface of the layer to which the electrolytic solution is applied.

Though the component 12 may include multiple layers of the absorbent material, each of the layers of the component 12 preferably has essentially the same major surface dimensions so that each layer is essentially coextensive with the other layers of the component 12. Though the layers of the component 12 do not necessarily need to have the same thickness, the layers of the component 12 preferably do have substantially the same thickness to reduce manufacturing complexity. Similarly, though the component 14 may include multiple layers of the absorbent material, each of the layers of the component 14 preferably has essentially the same major surface dimensions so that each layer is essentially coextensive with the other layers of the component 14. Though the layers of the component 14 do not necessarily need to have the same thickness, the layers of the component 14 preferably do have substantially the same thickness to reduce manufacturing complexity.

The absorbent material(s) of the components 12, 14 should also have a relatively high specific absorbency of at least about 0.5 ml of electrolytic solution per gram of absorbent material. Preferably, the specific absorbency of the absorbent material(s) should be at least about 1.0 ml of electrolytic solution per gram of absorbent material. More preferably, the specific absorbency of the absorbent material(s) should be at least about 3.0 ml of electrolytic solution per gram of absorbent material. Still more preferably, the specific absorbency of the absorbent material(s) should be at least about 5.0 ml of electrolytic solution per gram of absorbent material.

The absorbent material preferably is capable of quickly absorbing the electrolytic solution at a rate of about 3 ml of electrolytic solution per gram of absorbent material in less than about 3 minutes. More preferably, about 3 ml of electrolytic solution should be absorbed into 1 g of absorbent material in less than about 1 minute. Still more preferably, about 3 ml of electrolytic solution should be absorbed into 1 g of the absorbent material in less than about 10 seconds. This ability to quickly absorb the electrolytic solution is necessary to minimize, and preferably prevent, loss of electrolytic solution during charging of the components 12, 14 with the electrolytic solution and to minimize the time needed to charge the components 12, 14 with the electrolytic solution.

Examples of resinous materials that may be used to prepare the absorbent material of the components 12, 14 comprise various polymers and copolymers, such as those that are capable of being formed as solid or semi-solid foams, including polyurethanes; polyvinylpyrrolidones; polyvinyl alcohols; polyethylene oxides, such as POLYOX® polymers that are manufactured by Union Carbide Corporation; polyacrylic acids, such as CARBOPOL® polymers that are manufactured by B. F. Goodrich of Akron, Ohio; polyethylene glycols; polyacrylamides; cellulose derivatives, such as hydroxyethyl cellulose, hydroxypropylmethylcellulose,low-substitutedhydroxypropylcellulose,and cross-linked Na-carboxymethylcellulose, such as AC-DI-SOL™ polymers that are available from FMC Corporation of Philadelphia, Pa.; polyurethane-polyvinylpyrrolidone copolymers, such as Hydromer® copolymers that are available from Hydromer Corp. of Summerville, N.J.; and the like, along with blends thereof.

Some resinous materials, absent modification, do not have the absorbent characteristics specified above or the ability to maintain the electrolyte solution as a confluent liquid phase. Therefore, these resinous materials that lack the needed absorbent characteristics or confluent liquid phase maintenance ability must be treated with an absorption aid, such as a hydrophilic agent or a surfactant, to have the needed absorbent characteristics and the ability to maintain the electrolyte solution as a confluent liquid phase. For purposes of this disclosure, the absorption aid is defined as a chemical substance or solution that facilitates movement of the electrolytic solution and any included buffer suspension within voids of the absorbent material, such as within pores of foam that serves as the absorbent material. For purposes of this disclosure, the hydrophilic agent is defined as a chemical substance or solution that is capable of bonding with water molecules of the electrolytic solution to facilitate movement of the electrolytic solution and any included buffer suspension within the voids of the absorbent material by hydrophilizing the void structure of the absorbent material. For purposes of this disclosure, the surfactant is defined as a surface active chemical substance or solution that facilitates movement of the electrolytic solution and any included buffer suspension within voids of the absorbent material by reducing the surface tension of internal surfaces that define the voids within the absorbent material.

The absorption aid is preferably non-ionic so that the absorption aid does not interfere with medicament ion delivery. Some examples of materials that may serve as the hydrophilic agent include glycerine; organic or aqueous solutions of polyethylene glycol, polyethylene oxide, polyvinyl alcohol, peptide-based gelatins, such as carrageenan, and plant-based gums, such as karaya gum; as well as, mixtures of these. For example, the hydrophilic agent may be any of the solutions listed in Table 1:

TABLE 1

| Substance | Hydrophilic Agent (Grams of Substance To Grams of Water) |
|---|---|
| Karaya Gum (dry powder) | 1:about 25 to about 35 |
| Polyvinyl Alcohol (MW ranges from about 30,000 to about 70,000 Daltons) | 1:about 2.5 to about 3.5 |
| Polyethylene Glycol (MW is about 3,350 Daltons) | about 4 to about 6:1 |
| Polyethylene Oxide MW is about 1,000,000 Daltons) | 1:about 3 to about 5 |
| Carrageenan (natural gelatin) | 1:about 35 to about 45 |

Some examples of materials that may serve as the surfactant include primary alcohol ethoxylates, such as NEODOL 91-6 that is available from Shell Chemical Co.; secondary alcohol ethoxylates, such as TERGITOL 15-S-17 that is available from Union Carbide Corp; DABCO® series surfactants, such as DABCO® DC193 and DABCO® DC5043 surfactants that are available from Air Products and Chemicals, Inc. of Allentown, Pa.; polyoxypropylene-polyoxyethylene block copolymer-type surfactants, such as the PLURONIC® L62 and F88 PRILL surfactants that are available from BASF Corporation of Mt. Olive, N.J., as well as, mixtures of these, organic or aqueous solutions of these, and mixtures of these and any hydrophilic agent.

As those skilled in the art will readily recognize, particular absorption aids may need to be added at different times to modify different resinous materials. For example, many surfactants should be added during preparation of resinous polymers to accomplish beneficial cross-linking between the surfactant and the polymer and incorporate the surfactant into the polymer structure. As another example, some surfactants are best added to some resinous materials after the resinous material is formed, but before or during transformation of the resinous material into foam. For still other resinous materials, some absorption aids are best added after the resinous material has been formed into foam. Glycerine; organic or aqueous solutions of polyethylene glycol, polyethylene oxide, polyvinyl alcohol, peptide-based gelatins, such as carrageenan, and plant-based gums, such as karaya gum; and mixtures of these are examples of absorption aids that may be added after open cell polyurethane foam is formed. Furthermore, for some resinous materials, some absorption aids may be optionally incorporated into the resinous material at any time before, during, or after formation of the foam from the resinous material.

Some examples of resinous materials that may require treatment with the absorption aid to be used as the absorbent material of the components 12, 14 include various polymers and copolymers, including those that are capable of being formed as solid or semi-solid foams, such as polyethylene; polypropylene; polyisoprenes; polyalkenes; natural and synthetic rubbers; polyvinylacetate copolymers; ethylene vinyl acetate copolymers; polyamides, such as nylons; polyurethanes; polyvinylchloride; acrylic or methacrylic resins, such as polymers of esters of acrylic or methacrylic acids with alcohols, such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, either alone or copolymerized with ethylenically unsaturated monomers, such as acrylic acid, methacrylic acid, acrylamide, methacrylamide, N-alkoxymethyl acrylamides, N-alkoxymethyl methacrylamides, N-tert-butylacrylamide, and itaconic acid; N-branched alkyl maleamic acid, wherein the alkyl group has 10–24 carbon atoms; glycol diacrylates; and blends thereof. Of course, the need to treat a certain material with absorption aid will often depend on the characteristics of the particular form of the material, such as the average pore density (pores per linear inch of material surface) of foams and the average pore diameter of the foams. Furthermore, the need to treat a particular material with absorption aid would be moot if the manufacturer or supplier of the material already incorporated absorption aid into the material prior to delivery of the material.

Examples of fibrous materials that may be used as the absorbent material of the components 12, 14 include woven fabrics, such as fleece or felt made of polyester, rayon, cotton, wool. Examples of gums that may be used as the absorbent material of the components 12, 14 include natural gums, such as chitosan, guar gum, and locust bean gum. Examples of gels usable as the absorbent material include those based on various polysaccharides, such as pectin and starch, and those based on polyhydroxyethylmethacrylate. Again, some of these fibrous materials, gums, and gels may require treatment with absorption aid to be used as the absorbent material of the components 12, 14.

Though the buffer component 14 may be formed of woven fabric, gum, or gel, the buffer component 14 is preferably formed of an open cell foam, such as open cell polyurethane foam or polyvinyl alcohol foam. Polyurethane and polyvinyl alcohol foams are preferred over woven materials because the structure and pore arrangement of polyurethane foam and polyvinyl alcohol foams typically permit more uniform dispersal of the pH buffering agent, than does the structure and void arrangement of woven materials. Less uniform dispersal of the pH buffering agent in the absorbent material may allow localized pH effects, such as areas of pH above 8 or below 4, to form within the electrode 10. Polyurethane foam and polyvinyl alcohol foam are preferred over gums and gels because polyurethane and polyvinyl alcohol foams are typically capable of absorbing a much larger amount of electrolytic fluid in a much shorter period of time than gums and gels. Additionally, polyurethane foam and polyvinyl alcohol foam typically more readily maintain the distinct interface 21, as compared to gums and gels.

One type of open cell polyurethane foam that is used to form the component 12 and/or the component 14 may be based upon one or more foamable polyurethane prepolymers that are derived from toluene diisocyanate and that are marketed as part of the Hypol® group of products by W. R Grace & Company of Woburn, Mass. Some examples of suitable Hypol® polyurethane prepolymers include Hypol® FHP 2000, Hypol® FHP 2002, and Hypol® FHP 3000 prepolymers. Open cell polyurethane foam that is based upon Hypol® polyurethane prepolymer(s) typically exhibits the high absorbency and the relatively large specific absorbency that the absorbent material needs to have. Surfactant should typically be incorporated during the polymerization of the Hypol® polyurethane prepolymer(s) to insure that the resulting absorbent material absorbs the electrolytic solution at a relatively high rate.

The buffer component 14 that is formed of absorbent material takes the form of a support matrix that accepts, holds, and immobilizes the pH buffering agent. The support matrix of the buffer component 14 also accepts and holds a sufficient amount of electrolytic solution to support current flow between the conductive terminal 18 and the skin or between the skin and the conductive terminal 18. The pH buffering agent may be coated onto a surface of the buffer component 14 as the buffer coating (not shown) that faces, and is in contact with, the conductive component 16. Preferably, however, the pH buffering agent is heterogeneously dispersed throughout the buffer component 14, rather than being applied to the buffer component 14 as the buffer coating.

The pH buffering agent of the buffer component 14 neutralizes hydrogen ions or hydroxide ions that are generated by electrolysis of water when current is applied to the iontophoresis system that includes the electrode 10. Hydrogen ions and hydroxide ions are examples of adverse ions that are not intended for delivery into the body. If the anode of the iontophoresis system is structured like the electrode 10, the pH buffering agent may include basic elements that neutralize hydrogen ions generated at the anode. If the cathode of the iontophoresis system is structured like the electrode 10, the pH buffering agent may include acidic elements that neutralize hydroxide ions generated at the cathode.

One significant benefit of heterogeneously dispersing the pH buffering agent throughout the buffer component 14 is the ability to closely and accurately control the dosage of the pH buffering agent that is included in the electrode 10. For example, the method of the present invention permits a predetermined amount of pH buffering agent to be measured and fully incorporated into the absorbent material of the buffer component 14.

The technique for attaching the pH buffering agent as the buffer coating on the buffer component 14 entails applying an aqueous or organic suspension or slurry of the pH buffering agent onto a surface of the absorbent material. The buffer component 14 is then placed in a warm oven to remove moisture from the buffer coating of pH buffering agent or is allowed to air dry. Techniques such as these are labor intensive and are difficult to control. These techniques do not permit close control of the quantity of pH buffering agent that is associated with the buffer component 14.

For example, variables controlling how much buffering agent actually sticks to the absorbent material, such as the adhesive characteristics of the buffer coating, may change with time. Also, pH buffering agent that adheres less strongly to the absorbent material may be easily abraded or otherwise separated from the buffer component 14, especially during electrode component manufacture and assembly. Thus, to make electrodes that adequately maintain a safe pH range proximate the skin, it is typically necessary to apply as much as five times more pH buffering agent to form the buffer coating of the buffer component 14 than is chemically necessary for the actual neutralization of hydrogen ions or hydroxide ions or hydroxide ions that are formed after about forty minutes of iontophoresis.

One technique for heterogeneously dispersing the pH buffering agent within the buffer component 14 entails forming a buffer suspension by mixing the pH buffering agent with any carrier that is capable of being quickly absorbed into the absorbent material. Then, the buffer suspension is applied to the absorbent material to disperse the pH buffering agent within the absorbent material of the buffer component 14. This technique works best when the absorbent material is a resinous material that is in the form of a solid or semi-solid foam, though the technique may also be used when the absorbent material is fibrous material, such as woven fabric. This technique is believed to be unsuitable when the absorbent material is a resinous material in the form of a gum or a gel because of structural characteristics of gums and gels that would tend to inhibit dispersal of the pH buffering agent in the absorbent material using this carrier-based technique.

The buffer suspension of the pH buffering agent and the carrier is applied to the buffer component 14 to permit absorption of the carrier into the buffer component 14 and dispersal of the pH buffering agent within the component 14. The physical characteristics of the carrier, such as the viscosity and the surface tension of the carrier, should be adequate to permit the carrier to uniformly disperse the pH buffering agent throughout the buffer component 14. For example, the surface tension of the carrier preferably ranges from about 50 dyne/cm to about 70 dyne/cm at 20° C. and the viscosity of the carrier preferably ranges from about 1,300 cP to about 1,700 cP at 20° C. Some examples of materials that may suitably serve as the carrier include glycerine; organic or aqueous solutions of polyethylene glycol, polyethylene oxide, polyvinyl alcohol, peptide-based gelatins, such as carrageenan, and plant-based gums, such as karaya gum; and mixtures of these.

Alternatively, the carrier may consist of a mixture of water and one or more dispersants that is capable of uniformly dispersing the pH buffering agent in the water. Examples of suitable dispersants include polycarboxylic acids, such as polymethacrylates, including polymethacrylates available as Tamol® dispersants, Acusol® dispersants, and Acumer® dispersants from Rohm and Haas Co. of Philadelphia, Pa. Some particular examples of suitable Tamol® dispersants include Tamol® 850 dispersant and Tamol® 960 dispersant, and some particular examples of suitable Acusol® dispersants include Acusol® 445 dispersant and Acusol® 445N dispersant. When the dispersant is used, the dispersant and water are mixed to form the carrier. The amount of dispersant that is mixed with water is preferably selected so that the surface tension of the carrier ranges from about 50 dyne/cm to about 70 dyne/cm at 20° C. and the viscosity of the carrier preferably ranges from about 1,300 cp to about 1,700 cP at 20° C. The pH buffering agent, such as ion exchange resin, is subsequently mixed with the carrier to form the buffer suspension. The buffer suspension is then applied to the buffer component 14 to permit absorption of the carrier into the buffer component 14 and dispersal of the pH buffering agent within the component 14.

The pH buffering agent that is blended with the carrier may be in the form of granules or particles, such as ion exchange resin particles. The particle size of the pH buffering agent should be sufficiently large to immobilize or otherwise prevent any significant movement of the pH buffering agent within the absorbent material. However, the size of the particles should also be small enough to permit most of the particles to remain in suspension in the carrier for at least about an hour, without any agitation or stirring of the buffer suspension. The pH buffering agent particles should also be sufficiently small to prevent the absorbent material of the buffer component from filtering out more than a de minimis amount of buffering agent particles, or otherwise interfering with substantially uniform dispersal of buffering agent particles within the buffer component 14.

For example, when the material of the buffer component 14 has pore sizes ranging from about 200 micrometers to about 240 micrometers, the size of the buffering agent particles should be less than 240 micrometers and should preferably be less than about 200 micrometers, such as within a range from about 25 micrometers to about 150 micrometers. If the particles are large enough to interfere with substantially uniform dispersal of the particles within the buffering component 14, the particles should be ground to a size that will not interfere with substantially uniform dispersal of the particles within the buffering component 14.

There are several additional techniques for heterogeneously incorporating the pH buffering agent in the absorbent material of the buffer component 14. Each of these techniques causes the pH buffering agent to become physically entrapped within the absorbent material. When using these techniques, the molecular weight and particle size of any pH buffering agent that is used should be sufficiently large to immobilize or otherwise prevent any significant movement of the pH buffering agent within the absorbent material. Preferably, the molecular weight of the pH buffering agent ranges from about 5,000 to about 10,000 daltons to effectively immobilize the buffer in the buffer component 14.

As one alternative, the buffer component 14 may be formed by heterogeneously incorporating the pH buffering agent in one or more precursors of the absorbent material, prior to reacting the precursors. This technique works particularly well when the absorbent material is based on resinous material, such as resinous polymer or copolymer or a mixture of resinous polymer and/or copolymer. For example, the pH buffering agent may be mixed with one or more prepolymer components of resinous material, prior to polymerizing the prepolymer components to form the resinous material.

As another alternative for heterogeneously dispersing pH buffering agent in the absorbent material, the buffer component 14 may be formed as a hydrogel by casting a suitable mixture of the pH buffering agent, powdered gel particles, and water to form gel layer(s). The gel that is used in forming the buffer component 14 in this manner may be based on various polysaccharides, such as pectin and starch, and may be based on polyhydroxyethylmethacrylate.

In yet another alternative, the buffer component 14 may be formed by heterogeneously mixing the pH buffering agent in the absorbent material, prior to forming the absorbent material into the layer(s) of the buffer component 14. This technique may be used to form a composite mixture of the absorbent material and the pH buffering agent. For example, the buffer component 14 may be formed by mixing a gum with the pH buffering agent to uniformly disperse the pH buffering agent in the gum. Alternatively, the pH buffering agent, powdered gum particles, and water may be mixed to form the mixture of gum and pH buffering agent. The mixture of gum and pH buffering agent is then shaped, such as by casting, to form gum layer(s). The gum that is used in forming the buffer component 14 in this manner may be based on colloidal polysaccharide substances, such as natural gums, including chitosan, guar gum, and locust bean gum.

In another alternative, the buffer component 14 may be formed by heterogeneously incorporating the pH buffering agent in resinous material, such as resinous polymer or copolymer, prior to transforming the resinous material into the absorbent material. For example, the pH buffering agent may be melt blended with the resinous material after polymerization of prepolymer components of the resinous material and before the resinous material is transformed into the absorbent material, such as solid or semi-solid foam. When the absorbent material is in the form of foam, the absorbent product of this process is heterogenous pH buffering foam. When the absorbent material is heterogeneous pH buffering foam, the molecular weight of the pH buffering agent should be at least about 5000 daltons to help immobilize the pH buffering agent in the heterogenous pH buffering foam.

Heterogenous pH buffering foam includes at least two distinct phases. For any electrode 10 that includes the heterogeneous pH buffering foam, each of the phases should be insoluble in the solvent portion of any electrolytic solution included in the electrode to help immobilize physical movement of any component of the heterogeneous pH buffering foam within the electrode. The phases may each be solid or semi-solid in nature. Alternatively, some phase(s) may be solid in nature, and other phase(s) may be semi-solid in nature. One or more pH buffering agents make up one or more of the phases, and polymer foam or copolymer foam makes up the other phase(s).

The buffer component 14 may incorporate any pH buffering agent in any form. For example, the pH buffering agent may be any ion-exchange material, such as ion-exchange resin that is organic in chemical structure. Additionally, the pH buffering agent may be anionic or cationic ion-exchange material. Furthermore, the buffer component 14 may incorporate both anionic and cationic ion-exchange materials or amphoteric ion-exchange material. This permits interchangeable use of the electrode 10 as the anode, or the cathode of the iontophoresis system or, alternatively, as the anode and the cathode of the iontophoresis system.

The pH buffering agent, such as the ion-exchange material, should be capable of maintaining the pH of the electrolytic solution within the electrode 10 in a range of from about 4 to about 8 standard pH units to avoid irritating or burning the biological surface, such as the skin of the body. For example, the pH buffering agent should be capable of holding about 0.1 milliequivalents of acid or about 0.1 milliequivalents of base during an iontophoresis period of about 40 minutes or more while maintaining the about 4 to about 8 pH range of the electrolytic solution. Preferably, the pH buffering agent is capable of holding about 0.1 milliequivalents of acid and about 0.1 milliequivalents of base during an iontophoresis period of about 40 minutes or more while maintaining the about 4 to about 8 pH range of the electrolytic solution.

The pH buffering agent should also have a relatively high buffering capacity to aid in minimizing the size and weight of the buffer component 14 while maintaining the about 4 to about 8 pH range of the electrolytic solution during iontophoresis periods on the order of about 40 minutes or more. At a minimum, the buffering capacity of the pH buffering agent should be at least about 0.5 milliequivalents of acid or base per gram of pH buffering agent. Preferably, the buffering capacity of the pH buffering agent should be at least about 1.0 milliequivalents of acid or base per gram of pH buffering agent. More preferably, the buffering capacity of the pH buffering agent should be at least about 1.5 milliequivalents of acid or base per gram of pH buffering agent. Still more preferably, the buffering capacity of the pH buffering agent should be at least about 1.5 milliequivalents of acid per gram of pH buffering agent and at least about 1.5 milliequivalents of base per gram of pH buffering agent.

Examples of ion-exchange resins that are suitable for use as the pH buffering agent include various anion and cation exchange resins, in either gel or macroreticular form, such as the Amberlite® series of resins and the Duolite® series of resins available from Rohm & Haas Corporation and the Dowex® series of resins available from Dow Corporation of Midland, Mich. Examples of suitable Amberlite® resins include Amberlite® IRP-64, Amberlite® IRP-68, Amberlite® IRP-88, Amberlite® CG-50 and Amberlyst® A21 resins. Examples of suitable Duolite® resins include Duolite® C-433, Duolite® A-368, and Duolite® A-392S resins. Examples of suitable Dowex® resins include Dowex® WGR, Dowex® WGR-Z, and Dowex® MWA-1 resins. To aid in attaining the about 4 to about 8 pH range in the electrode 10, the ion-exchange resin should preferably be either weakly basic or acidic, be of fine particle size, and be pharmaceutical-grade gel-type resin.

One version of the ion exchange resin may be an ion-exchange copolymer that is formed by reacting a first prepolymer and a second prepolymer. The first and second prepolymers may be polymerized to form the ion-exchange copolymer using any suitable conventional copolymerization technique. The first prepolymer may consist of a single monomeric precursor or may consist of a mixture of different monomeric precursors. Examples of monomeric precursors suitable for use as the first prepolymer include alkanes, alkenes, and substituted benzenes, such as divinyl benzene.

The second prepolymer may generally be any single monomeric ion-exchange precursor or a mixture of different monomeric ion-exchange precursors. Monomeric ion-exchange precursors may be formed by attaching one or more ion-exchange functional groups to any monomeric precursors using any conventional chemical bonding technique, such as substitution or grafting. At least one of the monomeric precursors that acts as the first prepolymer and at least one of the monomeric precursors that is used in forming the monomeric ion-exchange precursor should be different from each other.

Examples of monomeric precursors suitable for use in making the monomeric ion-exchange precursor include substituted benzenes, such as divinyl benzene. Other examples of monomeric precursors suitable for use in making the monomeric ion-exchange precursor include a variety of urethanes, which may include a variety of different functional groups, such as (1) diol groups and diisocyanate groups and (2) triol groups and tri-isocyanate groups. Examples of ion-exchange functional groups that are suitable for attachment to the monomeric precursor(s) include carboxyl groups, amino groups, —$SO_3H$ groups, —$OPO_3H_2$ groups. Thus, some examples of the monomeric ion-exchange precursor, i.e. the second prepolymer, are acrylic acid and methacrylic acid.

One suitable ion-exchange copolymer is prepared by copolymerizing divinyl benzene, which serves as the first prepolymer, and methacrylic acid, which serves as the second prepolymer. One suitable copolymer of methacrylic acid and divinyl benzene is represented by structural formula I below:

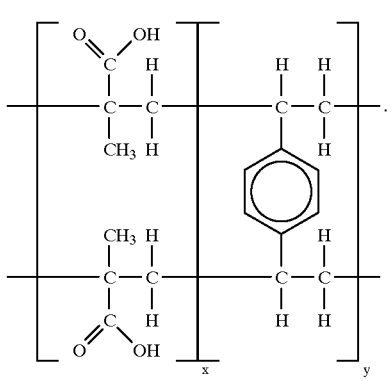

One example of the methacrylic acid/divinyl benzene copolymer with the structure of formula I is Amberlite® IRP-64, which is available from Rohm & Haas Co. of Philadelphia, Pa. Amberlite® IRP-64 has an x/y ratio of 12. Thus, an average monomer unit of the Amberlite® IRP-64 copolymer has 24 methacrylic acid groups per divinyl benzene group. Additionally, the Amberlite® IRP-64 copolymer is about 4.5% by weight divinyl benzene and about 95.5% by weight methacrylic acid. The Amberlite® IRP-64 copolymer may be dispersed in the absorbent material of the buffer component 14, or applied as part of the buffer coating of the buffer component 14, when the cathode of the iontophoresis system has the structure of the electrode 10.

When the anode of the iontophoresis system has the structure of the electrode 10, a metal salt of the ion-exchange copolymer may be dispersed in the buffer component 14 or may be applied as part of the buffer coating of the buffer component 14. The ion-exchange copolymer may be treated with a mineral acid, such as potassium chloride, to obtain the metal salt of the ion-exchange copolymer. Treatment of the copolymer of graphic formula I with potassium chloride yields the compound represented by graphic formula II, which is one example of a suitable metal salt of the ion-exchange copolymer:

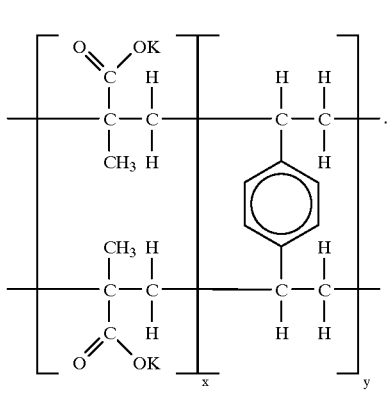

One example of the copolymer metal salt with the structure of formula II is Amberlite® IRP-88, which is available from Rohm & Haas Co. Amberlite® IRP-88 has an x/y ratio of 12. Thus, an average monomer unit of the Amberlite® IRP-88 copolymer has 24 metal salt groups of methacrylic acid per divinyl benzene group. The Amberlite® IRP-88 copolymer may be dispersed in the support matrix of the buffer component 14, or applied as part of the buffer coating of the buffer component 14, when the anode of the iontophoresis system has the structure of the electrode 10.

Continuing with FIG. 1, the conductive component 16 of the electrode 10 conducts current that is applied to the terminal 18 and distributes the current across an upper surface 22 of the buffer component 14. The upper surface 22 faces the conductive component 16. The conductive component 16 should uniformly distribute current across the upper surface 22. Preferably, the current density proximate the interface of the electrode 10 and the skin does not exceed about 0.5 milliamperes per square centimeter of skin surface. Current densities proximate the skin of higher than about 0.5 milliamperes per square centimeter of skin surface increase the likelihood of patient discomfort and irritation of the skin.

The conductive component 16 may be formed of any suitable conductive material. Preferably, the conductive component 16 is highly conductive and has a maximum resistivity of about 10 ohms-cm to enhance the efficiency of the electrode 10. The conductive component 16 should also be flexible so the electrode 10 can closely conform to the shape of the skin. The conductive component 16 should be impermeable to fluids, such as electrolytic solution contained in the electrode 10, to prevent degradation of the electro- chemical characteristics of the electrode 10. Examples of suitable materials for the conductive component 16 include a thin sheet or film of carbon, carbon- loaded silicon rubber, metal foil, electronically-conductive cloth, and electronically-conductive adhesive.

The adhesive covering 20 is an adhesive tape that serves as a structural support component that helps to hold the components 12, 14, 16 together and is also useful for securing the electrode 10 to the skin (not shown). The adhesive covering 20 additionally prevents seepage of electrolytic solution along the skin away from the electrode 10. The adhesive covering 20 is affixed to an upper surface 24 of the conductive component 16 and is preferably also affixed to an upper surface 26 of the medicament delivery component 12. The upper surfaces 24, 26 each face away from the skin and toward the adhesive covering 20. The medicament delivery component 12 is preferably somewhat wider than the components 14, 16 to permit adhesive contact between the covering 20 and the upper surface 26.

The adhesive covering 20 should be highly flexible so that the adhesive covering 20 readily conforms to the skin. The adhesive covering 20 may be formed on any suitable material, such as a thin layer of polyvinyl chloride foam or polyethylene foam that is coated with medical-grade pressure-sensitive adhesive. It is to be understood that other suitable flexible materials that are coated with adhesive may be used to form the adhesive covering 20.

The electrode 10 may also include a release layer 28 that is located adjacent to, and in contact with, the medicament delivery component 12. Portions of the adhesive covering 20 that are not in contact with the components 12, 14, and 16 are releasably attached to the release layer 28 to prevent the electrode 10 from becoming undesireably stuck to other objects prior to use. At the time of use, the release layer 28 is peeled from the electrode 10 to permit placement of the component 12 adjacent to the skin and to permit adhesive attachment of the adhesive covering 20 to the skin.

Though not depicted, the electrode 10 may alternatively include a wicking layer (not shown) between the component 12 and the release layer 28. When the wicking layer is included, the component 12 is preferably coextensive with the components 14 and 16. The wicking layer is folded at the peripheral edge of the component 12 to conform to the peripheral edge of at least the component 12 and is fixedly attached to the adhesive surface of the adhesive covering 20. With this arrangement, the wicking layer and the adhesive covering 20 cooperate to hold the components 12, 14, 16 together within the electrode 10. When the electrode 10 is placed against the skin, after removal of the release layer 28, the wicking layer is in contact with the skin and separates the component 12 from the skin. It has been found that the wicking layer negligibly, if at all, affects the medicament ion delivery characteristics of the electrode 10.

Examples of suitable materials for the wicking layer include non-woven blends of polyester and cellulose, such as Durx® 670 or Durx® 770, which are available from Berkshire Corporation of Great Barrington, Mass. Other examples of suitable materials for the wicking layer include blends of cellulose and polyethylene terephthalate, such as Unilayer® 1+2 or Unispun® 200, which are available from Midwest Filtration Company of Fairfield, Ohio. Still further examples of suitable materials for the wicking layer include various non-woven and interlining fabrics available from Hollingsworth & Vose Company of Floyd, Va.

Throughout the drawings, like elements are referred to using like reference characters.

The electrode 10 may be modified to form an electrode 110, as in FIG. 2, by omitting the conductive component 16. The electrode 110 also has a buffer component 114 that is substituted in place of the buffer component 14. The buffer component 114 has the same compositional and structural features as the buffer component 14, with one exception. Specifically, conductive filler (not shown) is incorporated and immobilized in the buffer component 114 to make the buffer component 114 conductive. All aspects of the buffer component 114, other than incorporation of the conductive filler, are the same as those of the buffer component 14. For example, the absorbent materials that is used to form the buffer component 114 are the same as the absorbent materials prescribed for use in forming the buffer component 14. As another example, the absorbent material of the buffer component 114 should have the same absorbent characteristics as the buffer component 14.

In the electrode 110, the conductive terminal 18 is attached to the buffer component 114 to direct current flow into the buffer component 114. The buffer component 114 and the medicament delivery component 12 each conduct current that is applied to the terminal 18. The current flowing through the medicament delivery component 12 and the buffer component 114 provides motive force that drives medicament ions into the body. Also, in the electrode 110, the adhesive covering 20 is affixed to the buffer component 114, the medicament delivery component 12, and the release layer 28, rather than to the conductive component 16, the medicament delivery component 12, and the release layer 28, as in the electrode 10.

The conductive filler may be any conductive form of carbon black; powdered graphite; carbon fibers; a metal powder, such as zinc powder, silver powder, and silver/silver chloride powder; or any other known electronically conductive filler material. The conductive filler may be dispersed throughout the buffer component 114, such as by uniformly mixing the conductive filler in the structural matrix of the buffer component 114 using any known mechanical means. Additionally, the particles of the conductive filler should have a shape and size that is adequate to immobilize the conductive filler within the buffer component 114.

Alternatively, the conductive filler may be incorporated in the buffer component 114 of the electrode 110 to create an electric potential between the upper surface 116 and a lower surface 118 of the buffer component 114. The upper surface 116 faces toward the adhesive covering 20, and the lower surface 118 faces away from the adhesive covering 20. The particles of conductive filler should have a shape and size that is adequate to immobilize the conductive filler within the buffer component 114. If the anode of the iontophoresis system is structured like the electrode 110, the electric potential should decrease between the surface 116 and the surface 118. If the cathode of the iontophoresis system is structured like the electrode 110, the electric potential should increase between the surface 116 and the surface 118.

In this alternative form, the conductive filler may be distributed on a graduated basis within the buffer component 114 or may be concentrated proximate the upper surface 116, as appropriate, to generate the change in potential needed for the anode and the cathode to function in the iontophoresis system. However, the conductive filler should not be concentrated proximate the lower surface 118 of the buffer component 114, since such concentration proximate the lower surface 118 would inhibit the ability of the pH buffering agent to neutralize water electrolysis products prior to diffusion of water electrolysis products across the lower surface 118 and into the medicament delivery component 12.

Current entering the buffer component 114 should be uniformly distributed across the upper surface 116 of the buffer component 114. Preferably, the current density proximate the interface of the medicament delivery component 12 and the skin does not exceed about 0.5 milliamperes per square centimeter of skin surface. Current densities proximate the skin surface of higher than about 0.5 milliamperes per square centimeter of skin surface increase the likelihood of patient discomfort and irritation of the skin.

Though not depicted, the electrode 110 may alternatively include the wicking layer (not shown) that was previously described with reference to the electrode 10. In the electrode 110, the wicking layer separates the component 12 and the release layer 28. In the electrode 110 that includes the wicking layer, the component 12 is preferably coextensive with the component 114. The wicking layer is folded at the peripheral edge of the component 12 to conform to the peripheral edge of at least the component 12 and is fixedly attached to the adhesive surface of the adhesive covering 20. With this arrangement, the wicking layer and the adhesive covering 20 cooperate to hold the components 12, 114, together within the electrode 110.

The electrode 10 may be modified to form an electrode 210, as in FIG. 3, by making a few minor adjustments. The electrode 210 includes the medicament delivery component 12 and the buffer component 14. The buffer component 14 is located adjacent to and in direct contact with the medicament delivery component 12. pH buffering agent is preferably dispersed uniformly throughout the buffer component 14. However, the buffer coating (not shown) that includes the pH buffering agent, as discussed in connection with the electrode 10, may alternatively be applied to an outer surface of the component 14. The electrode 210 further includes the conductive component 16 that is located adjacent to and in contact with the buffer component 14. In the electrode 210, the buffer component 14 is thus located between and in contact with the medicament delivery component 12 and the conductive component 16.

Though the component 12 and the component 14 are located adjacent to each other and are in direct contact with each other, the distinct interface 21 or boundary between the absorbent material of the component 12 and the absorbent material of the component 14 should exist in the electrode 210. The interface 21 is preferably smooth in nature. The absorbent material of the component 12 and the absorbent material of the component 14 should not merge with each other to any degree at the interface 21 between the components 12, 14.

The electrode 210 additionally includes the conductive tab or terminal 18, such as the conductive snap connector, that is attached in electrical communication to the conductive component 16. The electrode 210 also incorporates the adhesive covering 20 that is useful for securing the electrode 210 to the skin (not shown). The adhesive covering 20 is affixed to the upper surface 24 of the conductive component 16 in the electrode 210. The electrode 210 may also include the release layer 28 to prevent the adhesive covering 20 from becoming undesireably attached to a surface, such as a packaging surface, during storage of the electrode 210 prior to placement of the electrode 210 against the skin.

In the electrode 210, the components 12, 14, 16 are substantially coextensive with each other. Preferably, the components 12, 14 fully overlap each other and the components 14, 16 fully overlap each other. To avoid any need for adhesive activity between the components 12, 14, and between the components 14, 16, a wicking layer 212 is provided in the electrode 210 to secure the components 12, 14, 16 together and with respect to the adhesive covering 20. The wicking layer 212 rests against a major surface 214 of the component 12 that faces away from the component 14 and is secured to an adhesive surface 216 of the adhesive covering 20. With this arrangement, the wicking layer 212 and the adhesive covering 20 cooperate to hold the components 12, 14, 16 together within the electrode 210. The wicking layer 212 may be made of any of the materials mentioned with respect to the wicking layer in connection with the electrode 10. Despite the presence of the wicking layer 212, it is to be understood that it is acceptable for the components 12, 14 to adhere to each other and for the components 14, 16 to adhere to each other.

The release layer 28 rests against the wicking layer 212 opposite the component 12 and is affixed to exposed portions of the adhesive surface 216 where the wicking layer 212 is not affixed and does not extend over the adhesive surface 216. The release layer 28 is removed from the electrode 210 when it is desired to place the electrode 210 against the skin. When the electrode 210 is placed against the skin, after removal of the release layer 28, the wicking layer is in contact with the skin and separates the component 12 from the skin. It has been found that the wicking layer 212 negligibly, if at all, affects the medicament ion delivery characteristics of the electrode 210.

Though not depicted in FIG. 3, it is also to be understood that the buffer component 114 may be substituted in place of the buffer component 14 and the conductive component 16 in the electrode 210. When the buffer component 114 is substituted in place of the buffer component 14 and the conductive component 16 in the electrode 210, the conductive tab or terminal 18, such as the conductive snap connector, is attached in electrical communication to the buffer component 114 and the adhesive covering 20 is affixed to an upper surface of the buffer component 114 that faces away from the component 12.

All subsequent statements about the electrode 10 apply equally to the electrodes 110 and 210, unless otherwise indicated. Also, all subsequent statements about the buffer component 14 apply equally to the buffer component 114, unless otherwise indicated.

Though prior comments about the iontophoresis system mentioned delivery of medicament ions from one or the other of the electrodes that is structured like the electrode 10, both iontophoresis system electrodes may be used to deliver medicament ions. When each electrode of the iontophoresis system delivers medicament ions to the body, those skilled in the art will recognize that each electrode of the iontophoresis system acts as the active electrode for the respective medicament ions delivered from the respective electrode of the iontophoresis system. Similarly, each electrode of the iontophoresis system acts as the return electrode for the respective electrode of the iontophoresis system that is delivering medicament ions to the body.

One necessary step in making the electrode 10 is to produce the medicament delivery component 12 that is made of the absorbent material. Examples of the absorbent material that may used to make the medicament delivery component 12 include any of the resinous materials listed above, including resinous polymers and copolymers and mixtures of resinous polymers and/or resinous copolymers that are in the form of solid or semi-solid foams, such as solid open-cell polyurethane foam or semi-solid polyurethane- polyvinylpyrrolidone copolymer foam; woven fabrics, such as polyester, cotton, rayon, and woolen fleece or matting; gums, including natural gums, such as chitosan, guar gum, and locust bean gum; and gels, including those based on various polysaccharides, such as pectin and starch, and those based on polyhydroxyethylmethacrylate.

The absorbent material that is used to form the medicament delivery component 12 layer(s) may be obtained using any conventional technique for preparing the absorbent material. As explained above, some absorbent materials that are used to form the component 12 layer(s) must incorporate an absorption aid to have the absorbent characteristics required by the component 12. For these absorbent materials, the absorption aid may be incorporated into the absorbent material before, during, or after preparation of the absorbent material, as appropriate for the particular absorbent material and the particular absorption aid. Absorption aid may be incorporated into the absorbent material prior to or during formation of the absorbent material using any conventional technique that is appropriate for the particular absorption aid and the particular absorbent material. Details about application of absorption aid, in the form of the hydrophilic agent, to absorbent material after formation of the absorbent material are provided below.

After the absorbent material is prepared, the absorbent material is subjected to a suitable shaping process, such as extrusion, injection molding, compression molding, injection compression molding, or transfer molding, as appropriate for the particular absorbent material, to form the layer(s) of the medicament delivery component 12. The absorbent material layer(s) of the component 12 are subsequently cured, as necessary and appropriate for the particular absorbent material.

For absorbent materials that require absorption aid incorporation to have the absorbance characteristics needed by the component 12, absorption aid, such as the hydrophilic agent, may sometimes be incorporated after the particular absorbent material is produced, as those skilled in the art will recognize. The method of treating absorbent material of the medicament delivery component 12 with the hydrophilic agent involves several steps. First, the hydrophilic agent is applied to the absorbent material of the medicament delivery component 12 until the absorbent material is saturated with the hydrophilic agent. Some suitable techniques for applying the hydrophilic agent to the absorbent material include spraying the absorbent material with the hydrophilic agent or soaking the absorbent material in the hydrophilic agent.

After saturating the absorbent material of the medicament delivery component 12 with the hydrophilic agent, any excess of the hydrophilic agent is removed from the absorbent material by physical means. Examples of the physical means used to remove excess amounts of hydrophilic agent from the absorbent material include squeezing, pressing, and wringing. The hydrophilic agent is preferably selected to prevent the hydrophilic agent from flowing or oozing out of the absorbent material after the physical means remove any excess of the hydrophilic agent from the absorbent material. Finally, the absorbent material that includes the hydrophilic agent is warmed in an oven at a temperature of approximately 100° C. or less to remove moisture from the layer(s) of the medicament delivery component 12. The absorbent is dried in the oven until the weight of the component 12 remains steady.

Another necessary step in making the electrode 10 is to prepare the buffer component 14. In preparing the buffer component 14, the pH buffering agent may be heterogeneously dispersed within the absorbent material of the buffer component 14. Alternatively, the pH buffering agent may be applied as part of the buffer coating to the absorbent material of the buffer component 14.

One suitable absorbent material for use in forming the buffer component 14 is reticulated, fine pore, polyurethane foam with about 70 to about 80 pores per linear inch (ppi) of absorbent material surface and an average pore diameter ranging from about 200 to about 240 micrometers. A 2.5 mm thick disk that is made of this type of polyurethane foam weighs about 0.09 grams when the disk has a diameter of about 4.1 cm and a surface area of about 13.2 $cm^2$.

As mentioned, the pH buffering agent of the buffer component 14 is preferably capable of holding about 0.1 milliequivalents of acid and about 0.1 milliequivalents of base during an iontophoresis period of about 40 minutes or more while maintaining the about 4 to about 8 pH range of the electrolytic solution. Patients can generally tolerate current densities of less than about 0.5 $mA/cm^2$ during iontophoresis that occurs for periods of about 40 minutes. At a current density of 4 mA, the skin contact surface area of the electrode 10 therefore should be greater than about 8 $cm^2$, such as about 10 $cm^2$, 13 $cm^2$, or 22 $cm^2$.

A 50/50 mixture, by weight, of Amberlite® IRP-64 copolymer and Amberlite® IRP-88 copolymer generally has about 1.67 meq of each acid and each base per gram of the Amberlite® copolymer mixture. Therefore, when the pH buffering agent is a 50/50 mixture, by weight, of the Amberlite® IRP-64 and IRP-88 copolymers, the buffer component 14 should contain at least about 0.06 grams of the Amberlite® copolymer mixture to be capable of holding about 0.1 milliequivalents of acid and about 0.1 milliequivalents of base while maintaining the about 4 to about 8 pH range of the electrolytic solution. Therefore, when the buffer component 14 is made of a 2.5 mm thick disk of the reticulated polyurethane foam that has a diameter of about 4.1 cm and a surface area of about 13.2 $cm^2$, the ratio of the weight of the Amberlite® copolymer mixture relative to the weight of reticulated polyurethane foam of the 4.1 cm diameter disk may be as low as about 1.1 grams of the Amberlite® copolymer mixture per gram of the reticulated polyurethane foam.

The buffer component 14 may alternatively contain about 0.18 grams of the Amberlite® copolymer mixture to give the buffer component a safety factor of about 3 that permits the buffer component 14 to hold about 0.3 milliequivalents of acid and about 0.3 milliequivalents of base while maintaining the about 4 to about 8 pH range of the electrolytic solution. Preferably, the buffer component 14 contains about 0.3 grams of the Amberlite® copolymer mixture to give the buffer component a safety factor of about 5 that permits the buffer component 14 to hold about 0.5 milliequivalents of acid and about 0.5 milliequivalents of base while maintaining the about 4 to about 8 pH range of the electrolytic solution. Therefore, when the buffer component 14 is made of a 2.5 mm thick disk of the reticulated polyurethane foam that has a diameter of about 4.1 cm and a surface area of about 13.2 $cm^2$, the ratio of the weight of the Amberlite® copolymer mixture relative to the weight of the reticulated polyurethane foam of the 4.1 cm diameter disk is preferably about 3.3 grams of the Amberlite® copolymer mixture per gram of reticulated polyurethane foam.

When the dimensions of the reticulated polyurethane foam disk of the component 14 are changed, the weight of the foam disk will typically change. Those skilled in the art will therefore understand that the ratio of the weight of the 50/50 mixture of Amberlite® IRP-64 and IRP-88 copolymers to the weight of the reticulated polyurethane foam will need to be modified, when the dimensions of the reticulated polyurethane foam disk of the component 14 are modified, in proportion to the change in weight of the foam disk, to permit the buffer component 14 to hold the desired number of milliequivalents of acid and the desired number of milliequivalents of base while maintaining the about 4 to about 8 pH range of the electrolytic solution.

When the pH buffering agent is applied to the absorbent material as the buffer coating, the absorbent material is first prepared and formed into the layer(s) of the buffer coating 14. Examples of the absorbent material that may be coated with the buffer coating include any of the resinous materials listed above, including resinous polymers and copolymers and mixtures of resinous polymers and/or resinous copolymers that are in the form of solid or semi-solid foams; woven fabrics, such as polyester, rayon, cotton, and woolen fleece or matting; gums, including natural gums, such as chitosan, guar gum, and locust bean gum; and gels, including those based on various polysaccharides, such as pectin and starch, and those based on polyhydroxyethylmethacrylate.

The absorbent material that is used to form the buffer component 14 layer(s) may be obtained using any conventional technique for preparing the absorbent material. As explained above, some absorbent materials that are used to form the component 14 layer(s) will need to incorporate an absorption aid to have the absorbent characteristics required by the component 14. For these absorbent materials, the absorption aid may be incorporated into the absorbent material before, during, or after preparation of the absorbent material, as appropriate for the particular absorption aid and the particular absorbent material. Absorption aid may be incorporated into the absorbent material prior to or during formation of the absorbent material using any conventional technique that is appropriate for the particular absorption aid and the particular absorbent material.

Details about application of absorption aid, such as absorption aid in the form of the hydrophilic agent, to absorbent material after formation of the absorbent material are provided above in connection with the component 12. When absorption aid is applied after preparation of the absorbent material, the absorption aid application process and the process of forming the absorbent material into the buffer component 14 should be completed before the buffer coating of pH buffering agent is applied to the absorbent material. Otherwise, the absorption aid application and shaping process would be expected to cause removal of at least some of the buffer coating from the buffer component 14.

If it is desired, the buffer component 114 may be substituted in place of the buffer component 14 and the conductive component 16. The buffer component 114 has the same compositional and structural features as the buffer component 14, except that conductive filler (not shown) is incorporated and immobilized in the buffer component 114 to make the buffer component 114 conductive. The conductive filler is preferably incorporated into the absorbent material prior to shaping of the absorbent material into the layer(s) of the buffer component 114.

After the absorbent material is prepared, but prior to application of the buffer coating, the absorbent material is subjected to a suitable shaping process, such as extrusion, injection molding, compression molding, injection compression molding, or transfer molding, as appropriate for the particular absorbent material, to form the layer(s) of the buffer component 14. The absorbent material layer(s) of the component 14 are subsequently cured, as necessary and appropriate for the particular absorbent material.

After the absorbent material is formed into the layer(s) of the buffer component 14 and, if the buffer component 14 includes multiple layers of the absorbent material, the absorbent material layers are laminated together. Then, if the buffer component 14 includes multiple layers of the absorbent material, the buffer coating is applied to one exposed major surface of one of the outermost layers of absorbent material. Alternatively, if the buffer component includes only one layer of absorbent material, the buffer coating is applied to one of the major surfaces of the absorbent material layer. After applying the buffer coating, the buffer component 14 is positioned between the medicament delivery component 12 and the conductive component 16, with the buffer coating facing and in contact with the conductive component 16. When the buffer component takes the form of the buffer component 114, the buffer component 114 is positioned between the medicament delivery component 12 and the adhesive covering 20, with the buffer coating facing and in contact with the adhesive covering 20.

Application of the buffer coating to the absorbent layer of the buffer component 14 involves several different steps. First, the pH buffering agent, such as ion-exchange resin, is mixed with de-ionized water. The ratio of ion-exchange resin to water in the buffer coating, prior to application of the buffer coating to the absorbent material, should be in the range of about 150 to about 400 grams of ion exchange resin per liter of water and is preferably about 300 grams of ion-exchange resin per liter of water. Prior to application of the buffer coating to the absorbent material, the buffer coating that incorporates ion exchange resin should have the consistency of a slurry so that the coating may be applied to the absorbent material of the component 14 using a flow technique, such as a waterfall-type technique.

After the pH buffering agent and the water are mixed, the absorbent material of the component 14 may be placed on an open wire conveyor and passed under a flowing stream of the aqueous slurry of pH buffering agent so that the aqueous slurry accumulates as the buffer coating on one side of the absorbent material to the desired thickness. Where the density of ion exchange resin in the aqueous slurry is about 0.2 grams of ion exchange resin per milliliter of slurry, the bulk density of the ion exchange resin is about 0.6 grams per milliliter of ion exchange resin, and the desired amount of ion-exchange resin to be applied to the absorbent material as part of the buffer coating is about 0.35 grams of ion-exchange resin, the thickness of the buffer coating that is applied to the surface of the absorbent material, as measured after the buffer coating is dried, will need to be about 0.4 mm to about 0.8 mm when the area of the surface to be coated is about 10 $cm^2$, about 0.3 mm to about 0.6 mm when the area of the surface to be coated is about 13 $cm^2$, and about 0.2 mm to about 0.3 mm when the area of the surface to be coated is about 27 $cm^2$. The buffer component 14 is placed in an oven at a temperature of about 100° C. or less, after the buffer coating is applied, to dry the buffer coating by evaporating water from the buffer coating. Alternatively, the buffer component 14 may be dried in atmospheric air, rather than in the oven, though more drying time will be required. The buffer coating is allowed to dry until the weight of the buffer component 14 remains steady.

As an alternative to use of the buffer coating, the pH buffering agent may be heterogeneously dispersed in the absorbent material of the buffer component 14 in a number of different ways. For example, the absorbent material of the buffer component 14 may be treated with the buffer suspension, after formation of the absorbent material into the layer(s) of the buffer component 14, to heterogeneously disperse the pH buffering agent within the absorbent material.

When the pH buffering agent is incorporated into the absorbent material using the buffer suspension, there is typically no need to separately incorporate absorption aid into the absorbent material, when the carrier also functions as absorption aid. However, when the carrier is or includes water and does not include any of the materials that may serve as the hydrophilic agent (such as glycerine, and solutions of polyethylene glycol or polyethylene oxide, etc.), the absorbent material should incorporate or be treated with any absorption aid that is needed to make the absorbent material have the necessary absorption characteristics described above, before applying the buffer suspension to the absorbent material. Otherwise, the buffer suspension will not be absorbed at a sufficient rate or to a sufficient extent in the absorbent material.

The method of incorporating the pH buffering agent in the absorbent material of the buffer component 14 using the buffer suspension involves a number of steps. First, the carrier and the pH buffering agent are mixed together in a container to form the buffer suspension. As one example, when the carrier is glycerine and the pH buffering agent is ion-exchange resin, such as the 50/50 weight ratio mixture of Amberlite® IRP-64 and IRP-88 copolymers, the weight ratio of the ion-exchange resin to the glycerine in the buffer suspension should be about 2.5 grams of glycerine per gram of ion-exchange resin to attain the preferred ratio of 3.3 grams of the Amberlite® copolymer mixture per gram of reticulated open cell polyurethane foam when the buffer component 14 is made of a 2.5 mm thick disk of the polyurethane foam with a diameter of about 4.1 cm. These same results may be obtained by alternatively applying the buffer suspension to a 2.5 mm thick sheet of the polyurethane foam that is subsequently cut to form the 4.1 cm diameter polyurethane foam disks. Details about additional example compositions of the buffer suspension are provided in Table 2. In Table 2, the pH buffering agent is the 50/50 weight ratio mixture of Amberlite® IRP-64 copolymer and IRP-88 copolymer mentioned above.

TABLE 2

| Substance | Ratio of Weight of Substance (Grams) to Weight of pH Buffering Agent (Grams) In Buffer Suspension | Ratio of Combined Weight of Substance and Water (Grams) to Weight of pH Buffering Agent (Grams) In Buffer Suspension |
| --- | --- | --- |
| Karaya Gum (dry powder) | about 1:5 | about 6:1 |
| Polyvinyl Alcohol (MW ranges from about 30,000 to about 70,000 Daltons) | about 2:1 | about 8:1 |
| Polyethylene Glycol (MW is about 3,350 Daltons) | about 20:1 | about 24:1 |
| Polyethylene Oxide (MW is about 1,000,000 Daltons) | about 1:1 | about 5:1 |
| Carrageenan (natural gelatin) | about 1:6 | about 7:1 |

After the buffer suspension is formed, the buffer suspension is then applied to the absorbent material of the buffer component 14 until the absorbent material is saturated with the buffer suspension. Some suitable techniques for applying the buffer suspension to the absorbent material include spraying the absorbent material with the buffer suspension or soaking the absorbent material in the buffer suspension. When a layer of the absorbent material has a thickness of about 2.5 mm, the absorbent material typically needs to be soaked in the buffer suspension from about 1 minute to about 5 minutes to ensure that the buffer suspension saturates the absorbent material.

The carrier is preferably selected so that, without additional stirring or agitation beyond that supplied on initial mixing, the pH buffering agent remains substantially uniformly dispersed in the carrier and does not settle out in the carrier after being mixed with the carrier. This significantly minimizes or eliminates the need for mixing during the application process and thereby simplifies the process of applying the buffer suspension to the absorbent material. Selection of the carrier to maintain uniform dispersion of the pH buffering agent in the carrier after mixing is also believed to help attain uniform, or substantially uniform, dispersion of the pH buffering agent in the absorbent material upon application of the buffer suspension to the absorbent material. Some examples of materials that may suitably serve as the carrier include glycerine; organic or aqueous solutions of polyethylene glycol, polyethylene oxide, polyvinyl alcohol, peptide-based gelatins, such as carrageenan, and vegetable-based gums, such as karaya gum; and mixtures of these.

Alternatively, the carrier of the buffer suspension may consist of the previously mentioned mixture of dispersant and water. Examples of suitable dispersants include polycarboxylic acids, such as polymethacrylates, including polymethacrylates available as Tamol® dispersants, Acusol® dispersants, and Acumer® dispersants from Rohm and Haas Co. Some particular examples of suitable Tamol® dispersants include Tamol® 850 dispersant and Tamol® 960 dispersant, and some particular examples of suitable Acusol® dispersants include Acusol® 445 dispersant and Acusol® 445N dispersant.

After saturating the absorbent material of the buffer component 14 with the buffer suspension, any excess of the buffer suspension is removed from the absorbent material by physical means. Examples of the physical means used to remove excess amounts of the buffer suspension from the absorbent material include squeezing, pressing, and wringing. The carrier is preferably selected to prevent the carrier from flowing or oozing out of the absorbent material after the physical means remove any excess of the buffer suspension from the absorbent material. Finally, the absorbent material that includes the dispersed pH buffering agent is warmed in an oven at a temperature of about 100° C. or less, or in unheated air, to remove water from the layer(s) of the buffer component 14. The component 14 is allowed to dry until the weight of the component 14 remains steady.

Another technique for heterogeneously incorporating the pH buffering agent in the absorbent material entails preparation of heterogeneous pH buffering material, such as heterogeneous pH buffering foam or heterogeneous pH buffering gel. For absorbent material that is based on a resinous material, this technique generally entails (i) dispensing and mixing the ingredients (i.e. pH buffering agent, such as ion exchange resin, and prepolymer(s) of the resinous material), (ii) blowing the mixture to form heterogenous pH buffering foam, including incorporating a blowing agent that is capable of promoting a blowing reaction, such as a creaming reaction, rising reaction, or a full rise reaction, and (iii) setting the foam, such as via a gelation reaction. Some representative examples of prepolymers of the resinous material for use in forming the heterogeneous pH buffering foam include polyvinylpyrrolidone prepolymer; polyvinyl alcohol prepolymer; polyethylene oxide prepolymer, polyacrylic acid prepolymer, polyethylene glycol prepolymer; and polyacrylamide prepolymer.

During preparation of the heterogeneous pH buffering foam, the rate of the blowing reaction and the rate of the gelation reaction are determined by catalyst that catalyzes the reaction. Examples of the catalyst include tertiary amines, which promote blowing reactions, and organometallics, which promote gelation reactions. Tertiary amines may also help enhance blowing reaction rate, and organometallics may also help enhance gelation reaction rate. Additional blowing beyond that attributable solely to the blowing reaction may be obtained by incorporating an auxiliary blowing agent, such as methylene chloride or a suitable chlorofluorocarbon, such as CFC-11. The use of a silicone-based surfactant will help selectively control cell size and uniformity in the foam by reducing surface tension of the foam ingredients. The silicone-based surfactant may also enhance solubilization of the foam ingredients.

Another example of a suitable procedure for preparing heterogeneous pH buffering foam entails mixing any selected pH buffering agent, such as ion-exchange material, with water to form an aqueous suspension. Preferably, the pH buffering agent is finely powdered to enhance distribution of the pH buffering agent in the heterogeneous pH buffering foam and to enhance the surface area that is available for ion-exchange. The aqueous suspension is combined with prepolymer component(s) of the foam with rapid stirring to form a foam mixture. Examples of the prepolymer component(s) useable in forming the heterogeneous pH buffering foam include foamable polyurethane prepolymers that are derived from toluene diisocyanate and are marketed as part of the Hypol® group of products by W. R Grace & Company of Woburn, Mass. Some examples of suitable Hypol® polyurethane prepolymers include Hypol® FHP 2000, Hypol® FHP 2002, and Hypol® FHP 3000 prepolymers.

After the aqueous suspension is combined with the prepolymer component(s), the foam mixture is further agitated until expansion due to foaming subsides. The foam mixture is then subjected to a shaping process, such as extrusion, injection molding, compression molding, injection compression molding, or transfer molding, to form the layer(s) of the buffer component 14 and is subsequently cured. After formation, the polymer or copolymer foam and the ion-exchange resin that is dispersed within the foam form distinct phases of the heterogeneous pH buffering foam.

In heterogeneous pH buffering foam, the pH buffering agent, such as ion-exchange resin, is physically entrapped within the foam structure of the absorbent material. The heterogenous pH buffering foam should have an open cell structure that is capable of maintaining the electrolytic solution as a confluent liquid throughout the buffer component 14. The heterogenous pH buffering foam should also support enhanced movement of any hydrogen or hydronium ions within the foam and thereby permit free contact between the pH buffering agent and hydrogen or hydronium ions.

In another alternative, the pH buffering agent may be heterogeneously dispersed in resinous or colloidal material prior to formation of the buffer component 14 layer(s). For example, resinous material and pH buffering agent may be uniformly combined in a suitable mixing container. Next, the mixture of the resinous material and pH buffering agent are melt-blended at a temperature that supports uniform dispersion of the pH buffering agent within the resinous material without deleteriously affecting either the resinous material or the pH buffering agent. After melt-blending is complete, the blended mixture of resinous material and pH buffering agent is cooled to solidify the mixture. The mixture is then subjected to a shaping process, such as extrusion, injection molding, compression molding, injection compression molding, or transfer molding to form the layer(s) of the buffer component 14. The layer(s) of the buffer component 14 are subsequently cured.

Heterogeneous pH buffering hydrogel provides another alternative for heterogeneously dispersing pH buffering agent in the absorbent material of the buffer component 14. Heterogeneous pH buffering gel may be formed by casting a mixture of the pH buffering agent, powdered gel particles, and water to form gel layer(s) of the buffer component 14. Some representative examples of the colloidal material that may be used to form the gel of the heterogeneous pH buffering gel include various polysaccharides, such as pectin and starch, and polyhydroxyethylmethacrylate.

The pH buffering reactions occurring in the anode and the cathode of the iontophoresis system, when pH buffering agent that is dispersed in the buffer component 14 takes the form of ion-exchange material, may be generally characterized as ion-exchange reactions. As noted, hydrogen ions ($H^+$) are evolved at the positive electrode (anode) and hydroxide ions ($OH^-$) are evolved at the negative electrode (cathode) by electrolysis of water. Ion-exchange reactions occurring at the anode neutralize hydrogen ions ($H^+$) contained in the electrolytic solution and ion-exchange reactions occurring at the cathode neutralize hydroxide ions ($OH^-$) contained in the electrolytic solution.

As an example, the ion-exchange reaction that occurs in the anode that has the structure of the electrode 10, when the buffer component 14 includes the ion-exchange copolymer of Formula II as the pH buffering agent may be characterized according to reaction (1) as follows:

$$—COOK + H^+ \rightarrow —COOH + K^+, \tag{1}$$

where —COOK represents one example of a suitable ion-exchange functionality of the ion-exchange copolymer and where —COOH represents the carboxyl group. Additionally, $H^+$ represents hydrogen ion generated by electrolysis of water at the anode, and $K^+$ represents potassium ion that is released from the ion-exchange functionality by the ion-exchange reaction that neutralizes hydrogen ion ($H^+$). Potassium ion ($K^+$) is an example of the adverse ion that is not intended for delivery into the human or animal body. Of course, it is be understood that the ion-exchange functionality incorporated in the electrode 10 may be other than the —COOK functionality and that the ion released from the ion-exchange functionality during the ion-exchange reaction in the anode may be other than $K^+$.

Where the ion-exchange reaction occurs in accordance with reaction (1), it has been found that potassium ions ($K^+$) that are released by the ion-exchange reaction into the electrolytic solution are about five times less mobile than are hydrogen ions ($H^+$). The decreased mobility of potassium ions supplements the enhanced delivery of medicament that is observed by intentionally delivering most of the medicament ions using the medicament delivery component 12 and by placing the pH buffering agent away from the component 12. Specifically, the undesirable competitive effect between the potassium ion and medicament ions to be delivered to the body is significantly reduced, as compared to the competitive effect between hydrogen ion ($H^+$) and the medicament ions to be delivered to the body. Therefore, the efficiency of medicament ion delivery to the body is considerably improved when the —COOK functionality is incorporated in the buffer component 14 via the ion-exchange copolymer. Furthermore, neutralization of the hydrogen ion ($H^+$) makes it possible to maintain the pH at between about 4 and about 8 in the electrolytic solution of the anode that is structured like the electrode 10.

Though the ion-exchange functionality employed at the anode may be other than —COOK and though the adverse ion that is released from the ion-exchange functionality may be other potassium ion ($K^+$), the ion-exchange functionality that is selected should release an ion that is at least two times less mobile in the electrolytic solution than hydrogen ion. Preferably, the ionic functionality is selected so that the ion released from the ion-exchange functionality has the same mobility or less mobility in the electrolytic solution than potassium ion.

The ion-exchange reaction that occurs in the cathode that is structured like the electrode 10, when the buffer component 14 includes the ion-exchange copolymer of Formula I as the pH buffering agent, actually consists of two separate reaction sequences that may be characterized as reaction (2) and reaction (3) as follows:

$$—COOH + M^+ \rightarrow —COOM + H^+ \qquad (2)$$

$$H^+ + OH^- \rightarrow H_2O, \qquad (3)$$

In reaction (2), —COOH represents the ion-exchange functionality of the ion-exchange copolymer included in the buffer component 14 of the electrode 10 that serves as the cathode, and $M^+$ represents metal ion released from the ionic substance in the medicament delivery component 12 by dissociation of the ionic substance in the electrolytic solution. The metal ion ($M^+$) depicted in reaction (2) that evolves on dissociation of the ionic substance is an example of the complimentary ion that is not intended for delivery into the body. The metal ion released upon dissociation of dexamethasone disodium phosphate, one example of the ionic substance placed in the components 12, 14, is sodium ion ($Na^+$), which is an example of $M^+$ in equation (2).

Also, in reaction (2) and reaction (3), $H^+$ represents the hydrogen ion released by the ionic functionality during reaction (2) and $OH^-$ represents the hydroxide ion generated by electrolysis of water at the cathode. Of course, it is to be understood that the ion-exchange functionality incorporated in the ion-exchange copolymer of the buffer component 14 in the cathode may be other than —COOH and that the complimentary ion released upon dissociation of the ionic substance in the medicament delivery component 12 may be other than metal ion ($M^+$).

The net result of reaction (2) and reaction (3) is that hydrogen ion ($H^+$) released from the ionic functionality in the buffer component 14 of the cathode reacts with the hydroxide ion ($OH^-$) generated by electrolysis of water at the cathode to produce water ($H_2O$). Since the metal ion ($M^+$) that is dissociated from the ionic species exchanges with the hydrogen ion $H^+$ in reaction (2), the net effect of reaction (2) and reaction (3) is that no adverse or complimentary ion depicted in reaction (2) or reaction (3) remains in the electrolytic solution to compete for delivery to the body with medicament ions 14.

An automated system for manufacturing the electrode 10 of the present invention is schematically depicted at 300 in FIG. 4. The system 300 includes conveyers 310a, 310b, 310c, 310d, and 310e. Various components of the electrode 10 are individually prepared on individual ones of the conveyers 310a–310e. The conveyer 310a is also utilized for stacking and assembling the various components of the electrode 10. Specifically, at station A, the release layer 28 is positioned on the conveyer 310a. At station B, the medicament delivery component 12 is positioned on the release layer 28. At station C, the buffer component 14 is positioned on the medicament delivery component 12. At station D, the conductive component 16 is positioned on the buffer component 14. Finally, at station E, the adhesive covering 20 is positioned over the release layer 28, and components 12, 14, and 16. Plan views of the electrode 10 components, as present at the stations A–E, are provided beneath the conveyor 310a at the respective stations A–E.

Though not depicted in FIG. 4, it is to be understood that the various components of the system 300 may be controlled by computers or other linking equipment to sequence the system 300 components for smooth, automated operations. The components 12, 14, and 16, as well as, the adhesive covering 20 and the release layer 28, that are formed using the system 300 may be any planar shape, such as circular, elliptical, and rectangular. However, the components 12, 14, 16, the adhesive covering 20, and the release layer 28 are preferably rectangular, such as square, in shape when formed by the system 300 to minimize waste of the materials used to form the components 12, 14, 16, the adhesive covering 20, and the release layer 28.

The conveyers 310a–310e each include respective belts 311a–311e. Additionally, cutting mechanisms 312a–312e are individually associated with respective belts 311a–311e of conveyers 310a–310e. The cutting mechanisms 312a–312e may be any mechanism or mechanisms that are capable of cutting web material. For example, the cutting mechanisms 312a–312e may be die cutters. As another example, the cutting mechanisms 312a–312e may be optical cutting mechanisms, such as lasers. When the cutting mechanisms 312a–312e are die cutters, backing plates 313a–313e may be associated with respective cutting mechanisms 312a–312e so that the belts 311a–311e are disposed between the cutting mechanisms 312a–312e and respective backing plates 313a–313e. The backing plates 313a–313e provide a support surface for the cutting mechanisms 312a–312e during cutting operations.

The system 300 includes a roll 314 of the material that is used to form the release layer 28. A web 316 of the material on the roll 314 is dispensed so that the web 316 travels between the cutting mechanism 312a and the belt 311a of the conveyer 310a. The cutting mechanism 312a then cuts a portion of the web 316 to make the release layer 28 of the electrode 10. After the cutting mechanism forms the release layer 28, the remaining portion of the web 316 is lifted away from the conveyer 311a, and the release layer 28 remains on the belt 311a, as at station A.

The system 300 also includes a roll 318 of the absorbent material that forms the medicament delivery component 12. A web 320 of the material on the roll 318 is dispensed so that the web 320 travels between the cutting mechanism 312b and the belt 311b of the conveyer 310b. The cutting mechanism 312b then cuts a portion of the web 320 to make the medicament delivery component 12. The remaining portion of the web 320 is then lifted away from the belt 311b, and the cut web portion, in the form of the medicament delivery component 12, is deposited on the belt 311b. The conveyer 310b then deposits the medicament delivery component 12 on the release layer 28 at station B of the conveyer 310a.

The system 300 also includes a roll 322 of the absorbent material that is used to form the buffer component 14. A web 324 of the roll 322 absorbent material is dispensed so that the web 324 travels between the cutting mechanism 312c and the belt 311c. The cutting mechanism 312c cuts a portion of the web 324 to make the buffer component 14. The remaining portion of the web 324 is then lifted away from the belt 311a, and the cut web portion, in the form of the buffer component 14, is deposited onto the belt 311c. The conveyer 310c subsequently deposits the web portion 14 onto the medicament delivery component 12 at station C on the conveyer 310a.

The system 300 additionally includes a roll 326 of the material that is used to form the conductive component 16. A web 328 of the roll 326 material is dispensed so that the web 328 travels between the cutting mechanism 312d and the belt 311d. The cutting mechanism 312d cuts a portion of the web 328 to make the conductive component 16. The cutting mechanism 312d additionally cuts an aperture 329 in the conductive component 16 for receiving the conductive terminal 18. The remaining portion of the web 328 is then lifted away, and the cut portion of the web 328, in the form of the conductive component 16, is dropped onto the belt 311d. The conveyer 310d then deposits the conductive component 16 onto the buffer component 14 at station D on the conveyer 310a.

The system 300 further includes a roll 330 of the material that is used to form the adhesive covering 20 of the electrode 10. A web 332 of the roll 330 material is dispensed so that the web 332 travels between the cutting mechanism 312e and the belt 311e. The cutting mechanism 312e then cuts a portion of the web 332 to form the adhesive covering 20. The cutting mechanism 312e also cuts an aperture 333 in the adhesive covering 24 for receiving the conductive terminal 18. Thereafter, the remaining portion of the web 332 is lifted away from the belt 311e, and the cut portion of the web 332, in the form of the adhesive covering 20, drops to the belt 311e. The conveyer 310e then deposits the adhesive covering onto the conductive component 16 at station E on the conveyer 310a.

Though not depicted in FIG. 4, it is to be understood that the conveyer 310d may also include a structure (not shown) for positioning the conductive terminal 18 within the aperture 329 of the conductive component 16 after the cutting mechanism 312d cuts the aperture 329. Additionally, though not depicted in FIG. 4, it is to be understood that the system 300 may be configured to insert the conductive terminal 18 that is associated with the conductive component 16 within the aperture 333 that is cut in the adhesive covering 20. Additionally, though not depicted in FIG. 4, the system 300 preferably further includes a pressing station (not shown) for adhesively securing the adhesive covering 20 to the conductive component 16, to portions of the medicament delivery component 12 that face the adhesive covering 20 and which are not covered by the buffer portion 14, and to portions of the release layer 28 that face the adhesive covering 20 and which are not covered by the medicament delivery component 12.

An alternative system for making the electrode 10 is depicted at 400 in FIG. 5. The system 400 includes all of the features and details possessed by the system 300 of FIG. 4. Furthermore, the system 400 of FIG. 5 contains additional equipment for making the medicament delivery component 12 and the buffer component 14.

Specifically, the system 400 includes an apparatus 410 for saturating the portion of the web 320 that is to be cut by the mechanism 312b with absorption aid, such as the hydrophilic agent. The apparatus 410 may take the form of a sprayer 412 that sprays the hydrophilic agent on the web 320. Though not depicted in FIG. 5, the apparatus 410 may include a pair of sprayers 412 located on opposing sides of the web 320. Alternatively, the apparatus 410 may take the form of any other suitable equipment for saturating the web 320 with the hydrophilic agent, including, but not limited to, an apparatus (not shown) that permits the web 320 to be dipped in a pool (not shown) of the hydrophilic agent. The system 400 also includes a mechanism 414, such as a pair of rollers 416 located on opposing sides of the web 320, for squeezing excess hydrophilic agent out of the portion of the web 320 that is saturated with the hydrophilic agent by the apparatus 410.

The system 400 also includes an apparatus 418 for saturating the portion of the web 324 that is to be cut by the mechanism 312c with the buffer suspension of the pH buffering agent and the carrier. The apparatus 418 may take the form of a sprayer 420 that sprays the buffer suspension on the web 324. Though not depicted in FIG. 5, the apparatus 418 may include a pair of sprayers 420 located on opposing sides of the web 324. Alternatively, the apparatus 418 may take the form of any other suitable equipment for saturating the portion of the web 324 that is to be cut with the buffer suspension, including, but not limited to, an apparatus (not shown) that permits the web 324 to be dipped in a pool (not shown) of the buffer suspension. The system 400 also includes a mechanism 422, such as a pair of rollers 424 located on opposing sides of the web 324, for squeezing excess buffer suspension out of the portion of the web 324 that is saturated with the buffer suspension by the apparatus 418.

Though FIG. 5 depicts the system 400 as including the apparatus 410 and associated rollers 416, along with the apparatus 418 and associated rollers 424, it is to be understood that the system 400 may exclude the apparatus 410 and associated rollers 416 and/or the apparatus 418 and associated rollers 424. The system 400 may exclude the apparatus 410 and the associated rollers 416 when the absorbent material on the roll 318 has the absorbent characteristics required for the component 12 that are provided above. The system 400 may exclude the apparatus 418 and associated rollers 424 when the absorbent material on the roll 322 includes heterogeneously dispersed pH buffering agent or the buffer coating and therefore does not require application of the buffer suspension that is dispensed by the apparatus 418.

Returning to FIG. 4, though not depicted, it is to be understood that the system 300 may include the apparatus 418 for saturating the portion of the web 324 that is to be cut by the mechanism 312c with the buffer suspension of the pH buffering agent and the carrier, along with the associated rollers 424. The system 300 would include the apparatus 418 and associated rollers 424 when the absorbent material on the roll 322 does not already incorporate pH buffering agent and therefore requires application of the buffer suspension that is dispensed by the apparatus 418.

When the apparatus 418 is employed in the system 300, the apparatus 418 may alternatively include a pair of sprayers 420 located on opposing sides of the web 324. Alternatively, the apparatus 418 that may be used in the system 300 may take the form of any other suitable equipment for saturating the portion of the web 324 that is to be cut with the buffer suspension, including, but not limited to, an apparatus (not shown) that permits the web 324 to be dipped in a pool (not shown) of the buffer suspension.

Continuing with FIG. 5, though not depicted, it is to be understood that an apparatus (not shown) similar to the apparatus 410 may be associated with the web 324 for saturating the portion of the web 324 that is to be cut by the mechanism 312c with hydrophilic agent. The apparatus for saturating the portion of the web 324 may take the form of the sprayer 412 that sprays the hydrophilic agent on the web 324. The apparatus for saturating the portion of the web 324 with hydrophilic agent, along with the associated equipment for squeezing excess hydrophilic agent out of the web 324, should be positioned upstream of the equipment 418 for saturating the web 324 with the buffer suspension so that the hydrophilic agent has been applied and excess hydrophilic agent has been removed prior to application of the buffer suspension.

Though not depicted in FIG. 5, the apparatus associated with the web 324 for saturating the web 324 with hydrophilic agent, similar to the apparatus 410 associated with the web 320, may include a pair of sprayers 412 that are located on opposing sides of the web 324. Alternatively, the apparatus associated with the web 324 may take the form of any other equipment that is capable of saturating the portion of the web 324 to be cut with hydrophilic agent, including, but not limited to, an apparatus (not shown) that permits the web 324 to be dipped in a pool (not shown) of the hydrophilic agent.

The system 300 of FIG. 4 for making the electrode 10 may be modified to form a system that is depicted in FIG. 6 at 500 for making the electrode 110. The system 500 is similar to the system 300 of FIG. 4, with some exceptions. First, the system 500 of FIG. 6 does not include the conveyer 310d, the cutting mechanism 312d, the backing plate 313d, or the roll 326 that are used to make the conductive component 16. Furthermore, in the system 500, the conveyer 310c, the cutting mechanism 312c, the backing plate 313c, and the roll 322 are used to make the buffer component 114, rather than the buffer component 14 depicted in FIG. 4. To make the buffer component 114 in the system 500 of FIG. 6, the roll 322 absorbent material incorporates the conductive filler that is effective to make the buffer component 114 conductive. Other than the conductive filler, the material included on the roll 322 in the system 500 has the same composition as the material on the roll 322 that is included in the system 300.

The portion of the web 324 that is cut by the cutting mechanism 312c in the system 500 takes the form of the buffer component 114. After the buffer component 114 is cut from the web 324, the conveyer 310c deposits the buffer component 114 on the medicament delivery component 12 at station C on the conveyer 310a. Thereafter, the conveyer 310e deposits the adhesive covering 20 that is cut from the web 332 on the buffer component 114 at station E on conveyer 310a.

Though not depicted in FIG. 6, the conveyer 310e of the system 500 may also include a structure (not shown) for positioning the conductive terminal 18 within the aperture 333 that is cut in the adhesive covering 20. Also, though not depicted, the system 500 preferably further includes a pressing station (not shown) for adhesively securing the adhesive covering 20 to the buffer component 114, to portions of the medicament delivery component 12 facing the adhesive covering 20 that are not covered by the buffer portion 114, and to portions of the release layer 28 facing the adhesive covering 20 that are not covered by the medicament delivery component 12.

Though not depicted in FIG. 6, it is to be understood that the system 500 may include the apparatus 418 for saturating the portion of the web 324 that is to be cut by the mechanism 312c with the buffer suspension of the pH buffering agent and the carrier, along with the associated rollers 424. When the apparatus 418 is employed in the system 500, the apparatus 418 may include a pair of sprayers 420 located on opposing sides of the web 324. Alternatively, the apparatus 418 that may be used in the system 500 may take the form of any other suitable equipment for saturating the portion of the web 324 that is to be cut with the buffer suspension, including, but not limited to, an apparatus (not shown) that permits the web 324 to be dipped in a pool (not shown) of the buffer suspension.

Another system for making the electrode 10 is depicted at 600 in FIG. 7. The system 600 includes all of the features and details possessed by the system 500 of FIG. 6. Furthermore, the system 600 of FIG. 7 may include additional equipment for making the medicament delivery component 12 and the buffer component 114 out of absorbent material. Specifically, the system 600 may include the apparatus 410, that was described in the context of the system 400, for saturating the portion of the web 320 that is to be cut by the mechanism 312c with the hydrophilic agent. The system 600 may include the mechanism 414 that was described in the context of the system 400 for squeezing excess hydrophilic agent out of the portion of the web 320 that is saturated with the hydrophilic agent by the apparatus 410. All details prescribed for the apparatus 410 and the mechanism 414 in the context of the system 400 also apply to the apparatus 410 and the mechanism 414 that may be included in the system 600.

The system 600 may also include the apparatus 418 that was described in the context of the system 400 for saturating the portion of the web 324 that is to be cut by the mechanism 312c with the buffer suspension of the pH buffering agent and the carrier. The system 600 may also include the mechanism 422 described in the context of the system 400 for squeezing excess buffer suspension out of the portion of the web 324 that is saturated with the buffer suspension by the apparatus 418. All details prescribed for the apparatus 418 and the mechanism 422 in the context of the system 400 also apply to the apparatus 418 and the mechanism 422 that may be included in the system 600.

Though the system 600 may include the apparatus 410 and associated rollers 416, along with the apparatus 418 and associated rollers 424, it is to be understood that the system 600 may also exclude the apparatus 410 and associated rollers 416 and/or the apparatus 418 and associated rollers 424. The system 600 may exclude the apparatus 410 and the associated rollers 416 when the absorbent material on the roll 318 has the absorbent characteristics required for the component 12 that are provided above. The system 600 may exclude the apparatus 418 and associated rollers 424 when the absorbent material on the roll 322 includes heterogeneously dispersed pH buffering agent or the buffer coating and therefore does not require application of the buffer suspension that is dispensed by the apparatus 418.

Though not depicted in FIG. 7, it is to be understood that the system 600 may include an apparatus (not shown) similar to the apparatus 410 for saturating the portion of the web 324 that is to be cut by the mechanism 312c with hydrophilic agent. The apparatus for saturating the portion of the web 324 may take the form of the sprayer 412 that sprays the hydrophilic agent on the web 320. The apparatus for saturating the portion of the web 324 with hydrophilic agent, along with the associated equipment for squeezing excess hydrophilic agent out of the web 324 should be positioned upstream of the equipment 318 for saturating the web 324 with the buffer suspension so that the hydrophilic agent has been applied and excess hydrophilic agent has been removed prior to application of the buffer suspension.

Though not depicted in FIG. 7, it is to be understood that the apparatus associated with the web 324 for saturating the web 324 with hydrophilic agent, similar to the apparatus 410 associated with the web 320, may include a pair of sprayers 412 that are located on opposing sides of the web 324. Alternatively, the apparatus associated with the web 324 may take the form of any other equipment that is capable of saturating the portion of the web 324 to be cut with hydrophilic agent, including, but not limited to, an apparatus (not shown) that permits the web 324 to be dipped in a pool (not shown) of the hydrophilic agent.

Though not depicted in FIGS. 4–7, it is to be understood that the systems 600 may be modified to make the electrode 210 of FIG. 3 by including an additional conveyor (not shown) and conveyor belt (not shown) prior to the conveyor 310b with an associated roll and web of the wicking layer 212. This additional conveyor, conveyor belt, roll, and web would be positioned above the equipment at station A for forming the release layer 28 so that the wicking layer 212 is deposited on the release layer 28 at the station B. The equipment depicted at station B for forming the medicament delivery component 12 would be shifted so that the medicament delivery component is deposited onto the wicking layer 212, instead of the release layer 28. The remaining equipment depicted in or described with respect to FIGS. 4–7 for producing the remaining components (buffer component 14 and conductive component 16 or buffer component 114) and elements (adhesive covering 20 and conductive terminal 18) would be shifted to remain downstream of the equipment for forming the medicament delivery component 12 in the same relation to the equipment for forming the medicament delivery component 12 that is depicted in FIGS. 4–7.

In practice, use of the iontophoresis system that includes the cathode and/or the anode, either or both of which are structured like the electrode 10, is efficient and convenient. Where the active electrode of the iontophoresis system is structured like the electrode 10, the electrolytic solution containing the medicament ions may be injected into the component 12 or the component 14 of the electrode 10 after formation of the electrode 10 using any conventional technique, such as with a hypodermic syringe. Medicament ions that will be delivered to the body are typically included in the electrolytic solution by dissociating the ionic substance of interest in the appropriate solvent before the electrolytic solution is injected into the component 12 or 14.

For electrodes that will not be used to iontophoretically deliver medicament ions, electrolytic solution that includes conductive ions other than medicament ions may be injected into the component 12 or the component 14 of the electrode 10 after formation of the electrode 10 using any conventional technique, such as with the hypodermic syringe. Furthermore, as already explained, different medicament ions may be placed in the different electrolytic solutions that are placed in the medicament delivery components 12 of the cathode and the anode, for simultaneous iontophoretic delivery from both the cathode and the anode.

Next, both of the electrodes of the iontophoresis system are attached to the surface of the body, such as the skin of the patient. For any electrode of the iontophoresis system that is structured like the electrode 10, the component 12 faces, and is placed in contact with, the skin after the release layer 28 is removed. Additionally, the terminal 18 faces away from the skin, and the adhesive cover 20 is attached to the skin, after the release layer 28 is removed, to secure the electrode 10 to the body. If the return electrode of the iontophoresis system is structured like the electrode 10, the terminal 18 of the electrode 10 is connected to the source of electrical power to support current flow through the body. If the active electrode of the iontophoresis system is structured like the electrode 10, the terminal 18 of the electrode 10 is connected to the source of electrical power to initiate delivery of medicament ions into the body.

It should also be understood that the anode and the cathode may be connected to the source of electrical power such that the iontophoresis system that includes the anode structured like the electrode 10 and/or the cathode structured like the electrode 10 is capable of providing suitable current flow to the body to stimulate a muscle of the body. In this application, the medicament delivery component 12 may include electrolytic solution that includes medicament ions, if delivery of medicament ions will coincide with muscle stimulation. Alternatively, the medicament delivery component 12 may include electrolytic solution that is free of medicament ions and that includes conductive ions, if delivery of medicament ions will not coincide with muscle stimulation. In the case of muscle stimulation alone, the current source would supply an appropriate current form, such as alternating current.

The present invention is more particularly described in the following Examples which are intended as illustrations only since numerous modifications and variations within the scope of the general formulation will be apparent to those skilled in the art.

EXAMPLE 1

Example 1 demonstrates the process of incorporating the pH buffering agent into the absorbent material of the buffer component 14 using the buffer suspension of pH buffering agent dispersed in the carrier. In this Example, the pH buffering agent was a mixture of about 50% by weight Amberlite® IRP-64 copolymer and about 50% by weight Amberlite® IRP-88 copolymer. The carrier of the buffer suspension in this Example was glycerine. The absorbent material of the buffer component 14 in this Example was Foamex PREMIUM reticulated, fine pore, polyurethane foam that is available from Foamex, Inc. of Eddystone, Pa.

The Foamex PREMIUM polyurethane foam used in this Example had an average pore density of about 70 to about 80 pores per linear inch (ppi) of polyurethane foam surface and an average pore diameter ranging from about 200 micrometers to about 240 micrometers. The Foamex PREMIUM polyurethane foam was shaped like a disk. The foam disk was 2.5 mm thick and had a diameter of about 4.1 cm. The surface area of the foam disk was about 13.2 cm² and the foam disk weighed about 0.09 grams.

The goal of Example 1 was to incorporate about 3.3 grams of Amberlite® copolymer mixture per gram of Foamex PREMIUM polyurethane foam in the individual foam disks. Since each foam disk of this Example weighed about 0.09 grams prior to treatment with the buffer suspension, it was desired to incorporate about 0.3 grams of the Amberlite® copolymer mixture into each foam disk. 0.3 grams of the Amberlite® copolymer mixture permits the buffer component 14 to hold about 0.5 milliequivalents of acid and about 0.5 milliequivalents of base during a 40 minute period of iontophoretic medicament ion delivery, while maintaining a pH in the range of about 4 to about 8 in the electrolytic solution of the electrode 10. 0.5 milliequivalents of acid is about five times the amount of H⁺ ions that would be expected to be formed by electrolysis of water at the electrode 10 serving as the anode during 40 minutes of iontophoresis at an applied current of 4 mA, and 0.5 milliequivalents of base is about five times the amount of OH⁻ ions that would be expected to be formed by electrolysis of water at the electrode 10 serving as the cathode during 40 minutes of iontophoresis at an applied current of 4 mA.

In this Example, three different weight ratios of glycerine to resin (Amberlite® copolymer mixture) were used in the forming the buffer suspension. In one buffer suspension, the weight ratio of glycerine to resin was about 2.5 grams of glycerine per gram of Amberlite® copolymer mixture. In another of the buffer suspensions, the glycerine to resin ratio was about 4 grams of glycerine per gram of Amberlite® copolymer mixture. In the third buffer suspension, the glycerine resin ratio was about 5.8 grams of glycerine per gram of Amberlite® copolymer mixture.

In this Example, 132 of the foam disks were saturated with the buffer suspension having the glycerine to resin weight ratio of about 2.5, at least 20 of the foam disks were saturated with the buffer suspension having the glycerine to resin weight ratio of about 4, and at least 20 of the foam disks were saturated with the buffer suspension having the glycerine to resin weight ratio of about 5.8. The mean weight of each foam disk was determined to be 0.092 grams±0.003 grams prior to being saturated with the buffer suspension.

The foam disks were impregnated with the pH buffering agent by dipping each foam disk in the buffer suspension for a period of about 2 minutes to ensure saturation of the foam disks with the buffer suspension. The foam disks were then removed from the buffer suspension and were individually wrung out between two rollers that were separated from each other by about 2 mm to remove excess buffer suspension from the foam disks.

The foam disks were each individually weighed after removal of excess buffer suspension using the rollers. Based on the difference between the weight of the individual foam disks before application of the buffer suspension and the weight of the respective foam disks after saturation with and removal of excess buffer suspension, the weight of buffer suspension added to each foam disk following the dipping and wringing process was calculated. The weight of buffer suspension added to the foam disks versus the weight ratio of glycerine to resin in the buffer suspension is graphically presented in FIG. 8. From the plot of FIG. 8, it was determined that the weight of buffer suspension incorporated in each foam disk is a polynomial function of the glycerine to resin weight ratio in the buffer suspension.

Figure 9:
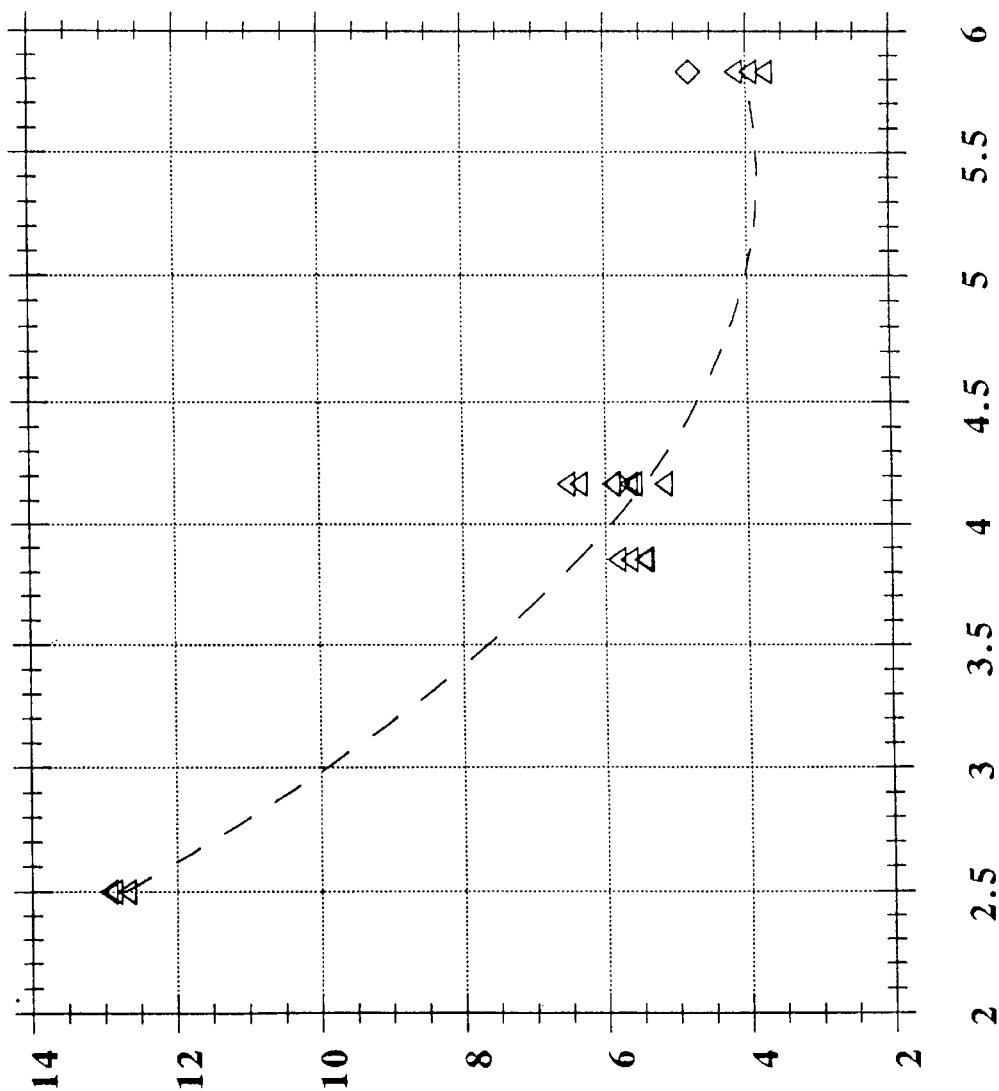
FIG. 9 is a graphical representation of the amount of buffer suspension incorporated in a buffer component of the present invention, per gram of foam in the buffer component, versus the weight ratio of glycerine to buffering resin in the buffer suspension.

For each foam disk, the weight of buffer suspension incorporated per gram of foam in the foam disk was then calculated. The results of these calculations are presented graphically in FIG. 9 as a function of the weight ratio of glycerine to resin in the buffer suspension. The data that are plotted in FIG. 9 demonstrate that the individual foam disks are capable of incorporating the buffer suspension in an amount that is equal to about 13 times the dry weight of the individual foam disks.

The amount of Amberlite® copolymer mixture that remained in each foam disk after the foam disk was wrung out was then calculated based on the glycerine to resin weight ratios of the different buffer suspensions. In this calculation, it was assumed that the process of absorbing the buffer suspension into the foam disks along with the process of removing excess buffering suspension from the foam disks using the rollers did not effect the glycerine to resin weight ratio of the buffer suspension that was incorporated in the foam disks. This assumption is based on the belief that any filtering effect of the disk foam upon particles of Amberlite® copolymer is negligible. This belief is thought to be reasonable considering that the average pore size of the Foamex PREMIUM foam is about 200 micrometers to about 240 micrometers, while the particles of the Amberlite® copolymers range in size from about 25 micrometers to about 150 micrometers. This assumption is also based on the belief that the glycerine to resin weight ratio in the buffer suspension was the same throughout the dipping operation. This belief is thought to be reasonable considering that no settling of Amberlite® copolymer from the glycerine was observed in the containers that held the various buffer suspensions.

Figure 10:
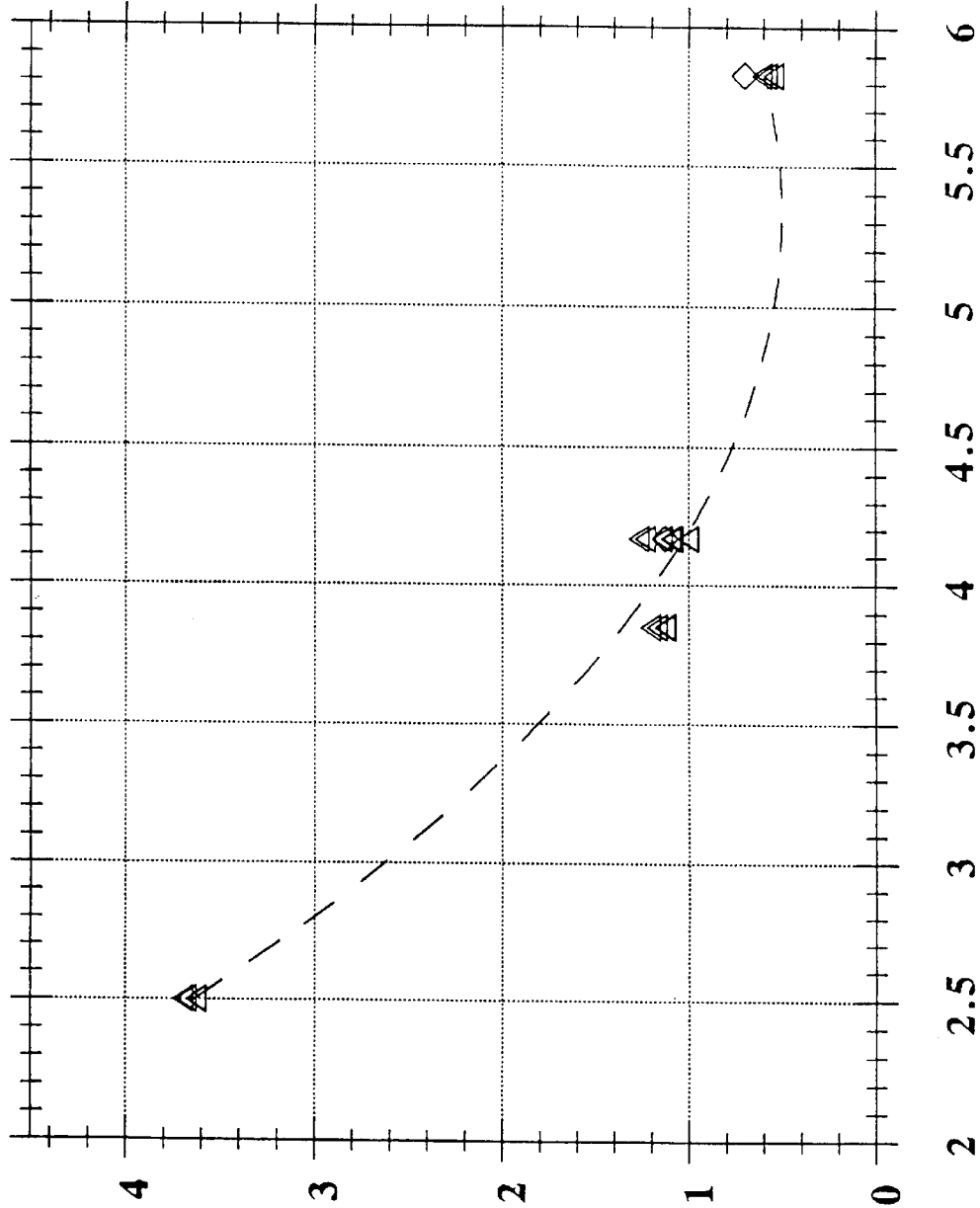
FIG. 10 is a graphical representation of the amount of buffering resin incorporated in a buffer component of the present invention, per gram of foam in the buffer component, versus the weight ratio of glycerine to buffering resin in the buffer suspension.

The calculated weight of Amberlite® copolymer incorporated per gram of Foamex PREMIUM foam in the foam disk, versus the weight ratio of glycerine to resin in the buffer suspension, is graphically presented in FIG. 10. FIG. 10 demonstrates that the buffer suspension with the glycerine to weight ratio of about 2.5 is needed to attain the desired ratio of 3.3 grams of Amberlite® copolymer mixture per gram of Foamex PREMIUM foam in the foam disk of the component 14 when the component 14 is made of a 2.5 mm thick disk of open cell polyurethane foam that has a diameter of about 4.1 cm. The buffer suspension with the glycerine to resin weight ratio of about 4 was only capable of forming the foam disks with a ratio of about 1.2 grams of Amberlite® copolymer mixture per gram of foam, whereas the buffer suspension with the glycerine to resin weight ratio of about 5.6 was only capable of attaining a ratio of about 0.6 grams of Amberlite® copolymer mixture per gram of foam in the foam disk.

The data obtained by impregnating the 132 different foam disks with the buffer suspension having the glycerine to resin weight ratio of about 2.5 confirms the conclusions reached based on the data of FIG. 10. Statistical data obtained from the 132 different foam disks impregnated with the buffer suspension having the glycerine to weight ratio of about 2.5 are presented in Table 3:

TABLE 3

| Statistical Data | Grams of Buffer Suspension Per Gram of Foam in Foam Disk | Grams of Amberlite ® Copolymer Mixture Per Gram of Foam in Foam Disk |
| --- | --- | --- |
| Mean | 11.45 | 3.28 |
| Std. Dev. | 0.70 | 0.20 |
| Minimum | 9.90 | 2.83 |
| Maximum | 12.94 | 3.70 |

TEST EQUIPMENT AND METHODS USED IN EXAMPLES 2–5 AND COMPARATIVE EXAMPLES 1–6

Examples 2–5 and Comparative Examples 1–6 simulate in vivo iontophoresis treatment using iontophoresis electrodes made of different materials and structured differently. Examples 2–3 and Comparative Examples 1–4 simulate iontophoretic delivery of dexamethasone phosphate. Example 4 and Comparative Example 5 simulate iontophoretic delivery of protonated lidocaine, and Example 5 and Comparative Example 6 simulate iontophoretic delivery of minoxidil base.

Figure 11:
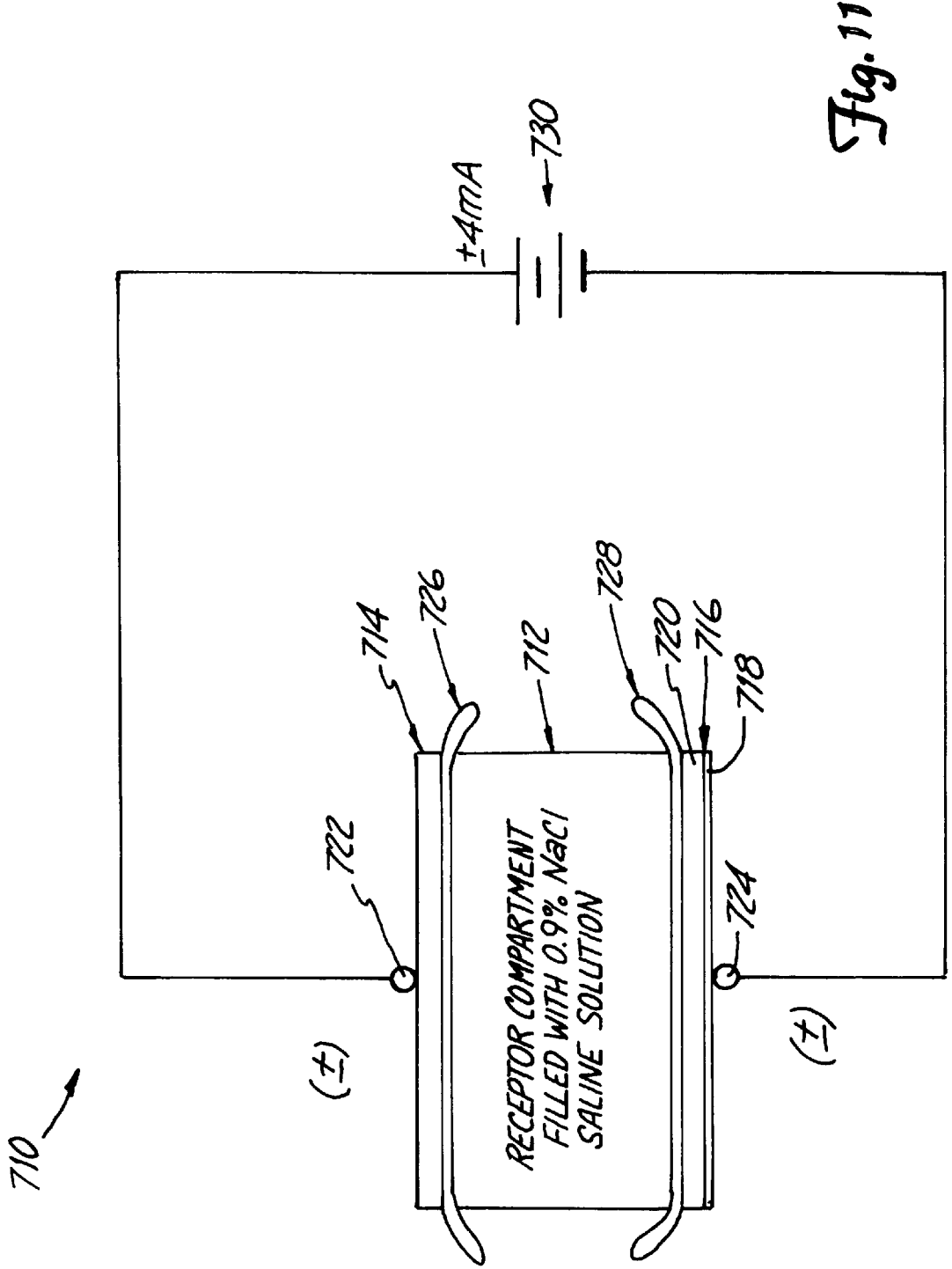
FIG. 11 is a schematic view of an apparatus for simulating iontophoresis using various pH buffered electrodes.

The test equipment used to simulate in vivo iontophoresis treatment in Examples 2–5 and Comparative Examples 1–6 is depicted at 700 in FIG. 11. The equipment 700 included a three-compartment diffusion cell 710 that provided conditions closely simulating those present during actual in vivo iontophoresis treatment. The cell 710 included a receptor compartment 712 that was filled with saline solution. The saline solution was a solution of water that included 0.9 weight % sodium chloride.

The cell 710 also included a donor compartment 714 and a return compartment 716. In Examples 2–5 and Comparative Examples 1–6, the donor compartment 714 was the electrode under consideration in the particular Example or Comparative Example. The receptor component 716 included a carbon film 718 that was attached in electrical communication to a conductive karaya gum pad 720. The donor compartment 714 included a conductive terminal 722, such as a conductive snap connector of the electrode under consideration in the particular Example or Comparative Example, and the return compartment 716 included a conductive terminal 724 that was attached in electrical communication to the carbon film 718 and the conductive karaya pad 720.

The cell 710 also included a hairless mouse skin 726 that was positioned between and in contact with the receptor compartment 712 and the donor compartment 714. The cell 710 further included a hairless mouse skin 728 that was positioned between and in contact with the receptor compartment 712 and the conductive karaya pad 720 of the return compartment 716. The hairless mouse skins were obtained from Charles River Laboratory of Wilmington, Mass. The hairless mouse skins 726, 728 each included a fresh whole thickness of mouse skin with both epidermal and dermal layers. New hairless mouse skins were used as the skins 726, 728 for each replicate of each Example and Comparative Example. In the cell 710, the skins 726, 728 were stretched taught and secured in place by teflon holders (not shown) with the dermal sides of the mouse skins positioned against the receptor compartment 712.

The cell 710 was sized to ensure that the effective skin 726 surface area available for medicament ion transport from the compartment 714 to the compartment 712 matched the size and shape of the effective delivery area of the electrode being tested in the particular Example or Comparative Example. The effective delivery area of the particular electrode being tested was defined as the area of the receptor compartment 714 surface that was in contact with the mouse skin 726. All in vivo simulations were conducted at room temperature with continuous stirring of the solution in the receptacle compartment 712. In each of the Examples and Comparative Examples, the number of experimental replicates was at least 10.

During each simulation, the iontophoresis electrode under consideration was filled to capacity with medicament ion solution prior to the start of the simulation. The conductive terminal 722 of the donor compartment 714 and the conductive terminal 724 of the receptor compartment 724 were each attached to a galvanostatic power supply 730. The galvanostatic power supply 730 was a Model 273A potentiostat/galvanostat that is available from EG&G Princeton Applied Research of Princeton, N.J. Depending upon the ionic state of the medicament ion employed in the donor compartment 714, a constant current of either +4 mA or −4 mA current was applied to the donor compartment 714 for a period of 40 minutes in each of the replicates of Examples 2–5 and Comparative Examples 1–6.

Voltage drop across the hairless mouse skins 726, 728 could not be accurately measured at reasonable cost. Therefore, the voltage drop across the cell 710 between the conductive connectors 722 and 724 was monitored instead. The measured voltage drop across the cell 710 during Examples 2–5 and Comparative Examples 1–6 generally ranged between about 7 and 15 volts. Significant variations were noticed even among replicate experimental runs. These variations are believed to be due to the biological nature of the hairless mouse skin and due to differences in skin resistance from mouse to mouse.

The dexamethasone sodium phosphate used in Examples 2–3 and Comparative Examples 1–4 and the lidocaine hydrochloride used in Example 4 and Comparative Example 5 were obtained from Paddock Laboratory of Minneapolis, Minn. The minoxidil base used in Example 5 and Comparative Example 6 was obtained from Drs. Pedro Huerta, Lloyd Allen, and Vilas Prahbu of the University of Oklahoma College of Pharmacy in Oklahoma City, Okla. The medicament ion solutions used in the various electrodes in Examples 2–5 and Comparative Examples 1–6 were prepared using either high pressure liquid chromatograph-grade water obtained from Burdick & Jackson of Muskegon, Mich. or deionized water having a resistance greater than 18 MΩ that was obtained from a Barnstead E-PURE system. The Barnstead E-PURE system is available from the Bamstead Company of Boston, Mass.

The amount of medicament ions transferred into the receptor compartment 712 during the various Examples and Comparative Examples was determined at approximately 5 minute intervals during the 40 minute iontophoresis period using High Pressure Liquid Chromatography (HPLC). Medicament ion concentrations in the receptor compartment 712 solution were determined using 100 µL samples. To maintain a constant volume of the receptor compartment 712 solution, each withdrawn aliquot volume was replaced with an equal volume of 0.9 weight percent saline solution.

The concentration of the particular medicament ion under consideration in the various simulations of the particular Examples and Comparative Examples was determined from the receptor compartment 712 solution sample using HPLC. The High Pressure Liquid Chromatography system employed a Waters 501 HPLC pump and a Waters 440 absorbance detector that are available from Waters Corp. of Milford, Mass. Peak height data was collected using Millennium 2010 software that is available from Waters Corp.

The HPLC analysis of dexamethasone phosphate in the sample of receptor compartment 712 solution was conducted with a Waters µBondapak $C_{18}$ (3.9 mm×300 mm) exclusion column obtained from Waters Corp. of Milford, Mass. The mobile phase of the HPLC system during dexamethasone phosphate determinations was a solution of 60 weight % methanol and 40 weight % water that contained 20 mM potassium phosphate monobasic and had a pH of about 4.2. Ultraviolet light with a wavelength of 254 nanometers was used for detection. The flow rate of the receptor compartment 712 solution sample in the HPLC system was set at 2.0 ml/minute so that the retention time of dexamethasone phosphate in the HPLC system was about 3.5 minutes.

The HPLC analysis of protonated lidocaine in the sample of receptor compartment 712 solution was conducted with a Waters µNovapak $C_{18}$ (3.9 MM×150 MM) exclusion column obtained from Waters Corporation. The mobile phase of the HPLC system was a solution with a pH of about 3 that contained 53.6 weight % acetonitrile, 43.8 weight % water, 1.9 weight % triethylamine, and 0.7 weight % phosphoric acid. Ultraviolet light with a wavelength of 254 nm was used to detect the protonated lidocaine. The flow rate of the receptor compartment 712 solution sample in the HPLC system was set at 1.0 ml/min so that the retention time of protonated lidocaine in the HPLC system was about 2.7 minutes.

The HPLC analysis of minoxidil base in the sample of receptor compartment 712 solution was conducted with a Waters µBondapak $C_{18}$ (3.9 mm×300 mm) exclusion column obtained from Waters Corporation. The mobile phase of the HPLC system was a solution of 60 weight % methanol and 40 weight % water that contained 20 mM potassium phosphate monobasic and had a pH of about 4.2. Ultraviolet light with a wavelength of 254 nanometers was used to detect the minoxidil base. The flowrate of the receptor compartment 712 solution sample in the HPLC system was set at 2.5 ml/min so that the retention time of minoxidil base in the HPLC system was about 3.0 minutes.

DATA ANALYSIS TECHNIQUES USED IN EXAMPLES 2–5 AND COMPARATIVE EXAMPLES 1–6

The transport behavior for medicament ions moving from the donor compartment 714 into the receptor compartment 712 for each of the different Examples and Comparative Examples was assessed by plotting the cumulative amount (µg) of medicament ion delivered into the receptor compartment 12 as a function of the applied charge (mA—min). The cumulative mount of medicament ion delivered per unit of effective delivery area of the donor compartment 714 was also plotted as a function of time to perform further detailed analysis of the transport behavior data.

The steady state flux of medicament ions into the receptor compartment 712 was calculated by determining the slope of the linear portion of the plot of cumulative amount of delivered medicament ion per unit of effective delivery area versus time, by linear regression analysis. Thus, the steady state flux calculation took into account the lag time, which is the time required for the medicament ions to penetrate the mouse skin at the beginning of the iontophoresis simulation. The lag time corresponds to the time during which the steady state flux into the receptor compartment 712 is 0. The lag time was determined by first extrapolating the linear portion of the plot to the time axis and then measuring the period between time 0 and the point where the extrapolated line intercepted the time axis.

DESCRIPTION OF DONOR ELECTRODES USED IN EXAMPLES 2–5 AND COMPARATIVE EXAMPLES 1–6

The iontophoresis electrode used in Examples 2, 4, and 5 was the electrode 210 that is depicted in FIG. 3. In the electrode 210 used in Examples 2, 4, and 5, the conductive component 16 was a thin carbon film, and the medicament delivery component 12 was a disk of AMREL™ 6 polyurethane foam that is available from the Kenn-Med Division of Rynel, Ltd., Inc of Boothbay, Me. The AMREL™ 6 polyurethane foam disk was about 3 mm thick and had a diameter of about 4.1 cm. The AMREL™ 6 polyurethane foam used in these Examples as the component 12 had an average pore density ranging from about 50 to about 200 pores per linear inch (ppi) of the polyurethane foam surface and an average pore diameter ranging from approximately 150 micrometers to approximately 350 micrometers. The contact area between the wicking layer 212, which is equivalent to the receptor compartment 714 surface in Examples 2, 4, and 5, and the mouse skin 726 was about 22 $cm^2$, based on the about 5.3 cm diameter of the wicking layer 212. Thus, the effective delivery area of the electrode 210 for medicament ion delivery was about 22 $cm^2$.

The buffering component 14 of the electrode 210 used in Examples 2, 4, and 5 was a disk of Foamex PREMIUM polyurethane foam that incorporated the pH buffering agent. The foam disk was about 2.5 mm thick and had a diameter of about 4.1 cm. The Foamex PREMIUM foam used in these Examples had an average pore density of about 70 to about 80 pores per linear inch (ppi) of the polyurethane foam surface and an average pore diameter ranging from approximately 200 micrometers to approximately 240 micrometers.

The foam disk of the buffering component 14 included pH buffering agent that was incorporated into the foam of the disk using the buffer suspension of pH buffering agent dispersed in the carrier. In Examples 2, 4, and 5, the foam disk of the buffer component 14 had a weight of about 0.9 grams, prior to incorporation of the buffer suspension into the disk. About 0.3 grams of the pH buffering agent was incorporated into the foam disk of the buffer component 14 in accordance with the detailed procedure set forth in Example 1. The pH buffering agent of Examples 2, 4, and 5 was a mixture that contained about 50 weight % Amberlite® IRP-64 copolymer and about 50 weight % Amberlite® IRP-88 copolymer. The carrier of the buffer suspension in Examples 2, 4, and 5 was glycerine. The weight ratio of glycerine to resin in the buffer suspension was about 2.5 grams of glycerine per gram of the Amberlite® copolymer mixture.

The iontophoresis electrode 210 used in Example 3 was similar to the electrode 210 used in Examples 2, 4, and 5, with the exception of the buffer component 14. In the electrode 210 of Example 3, the buffer component 14 was a disk of polyester fleece that was coated with pH buffering agent. The fleece disk had the same dimensions as the foam disk that was used in the buffer component 14 of Examples 2, 4, and 5. The pH buffering agent included about 50 weight % Amberlite® IRP-64 and about 50 weight % Amberlite® IRP-88. The coating of the pH buffering agent included 0.35±0.05 grams of the Amberlite® copolymer mixture.

The coating of the Amberlite® copolymer mixture was placed as a substantially uniform thickness onto one side of the polyester fleece disk so that the Amberlite® copolymer mixture was sandwiched between the conductive component 16 and the polyester fleece disk. The coating was prepared by mixing about 150 grams of the Amberlite® copolymer mixture with about one liter of deionized water to make an aqueous slurry of the Amberlite® copolymer mixture. The polyester fleece disk was placed on an open wire conveyor and passed under a flowing stream of the aqueous slurry of Amberlite® copolymers so that the aqueous slurry accumulated as the buffer coating on one side of the disk to a thickness of about 0.03 cm. The buffer-coated polyester fleece disk was then placed in an oven at a temperature of about 100° C. to evaporate the water contained in the coating. The buffer-coated polyester fleece disk was allowed to dry in the oven until the weight of the buffer-coated polyester fleece disk remained steady.

The iontophoresis electrode used in Comparative Example 1 included each of the elements of the electrode 210 used in Examples 2, 4, and 5. However, in the electrode 210 of Comparative Example 1, the positions of the component 12 and the component 14 were switched so that the component 12 was located between the conductive element 16 and the component 14. The purpose of switching the components 12 and 14 in Comparative Example 1 was to demonstrate that positioning of the pH buffering agent with respect to the medicament delivery component 12 is critical to attaining the surprising benefits of the present invention.

The iontophoresis electrode used in Comparative Example 2 was similar to the electrode used in Example 3, with a couple of significant exceptions. First, the electrode of Comparative Example 2 did not include the component 12. Instead, the component 12 was deleted so that the component 14 was directly located between and in direct contact with the conductive component 16 and the wicking layer 212. Second, the polyurethane foam disk of the component 14 used in Comparative Example 2 was made of the Rynel AMREL™ 6 polyurethane foam that was used to form the medicament delivery component 12 in Examples 2, 4, and 5, rather than polyester fleece that was used to form the buffer component 14 in Example 3.

In Comparative Example 2, pH buffering agent was coated onto the foam disk of the buffer component 14 using the same procedure described in Example 3, with the exception that the buffer coating was a solution of pH buffering agent and glycerine, rather than the solution of pH buffering agent and water. The pH buffering agent that was coated onto the foam disk of the component 14 in Comparative Example 2 consisted of the same ratio of Amberlite® copolymers and the same weight of Amberlite® copolymer mixture as the electrode 210 used in Example 3. The Amberlite® copolymer mixture and the glycerine were mixed in a ratio of approximately 1 gram of Amberlite® copolymer mixture to 2.5 grams of glycerin. Other than for substitution of glycerine in place of water, the pH buffering agent that was coated onto the foam disk of the component 14 in Comparative Example 2 was applied to the foam disk in accordance with the details and procedure described in Example 3.

The iontophoresis electrode used in Comparative Example 3 was similar to the iontophoresis electrode 210 used in Examples 2, 4, and 5, except that the component 12 was deleted from the electrode used in Comparative Example 3. The wicking layer 212 held the component 14 in place between the wicking layer 212 and the conductive component 16 in Comparative Example 3. The polyurethane foam disk of the component 14 used in this Example was made of the Foamex PREMIUM polyurethane foam that was used to form the buffer component 14 in Examples 2, 4, and 5. The pore density and average pore diameter of the Foamex PREMIUM polyurethane foam used in Comparative Example 3 was the same as that of the Foamex PREMIUM polyurethane foam used in Examples 2, 4, and 5. The foam disk of the component 14 in Comparative Example 3 had the same dimensions as the component 14 foam disk in Examples 2, 4, and 5.

The component 14 of the electrode used in Comparative Example 3 incorporated the same ratio of Amberlite® copolymers and the same weight of Amberlite® copolymer mixture as the electrode 210 used in Examples 2, 4, and 5. The pH buffering agent was incorporated into the foam disk of the component 14 in accordance with the details and procedure described in Examples 1, 2, 4, and 5.

The iontophoresis electrode used in Comparative Examples 4, 5, and 6 included the conductive component 16, conductive terminal 18, and adhesive covering 20, as arranged in the electrode 210. The electrode of Comparative Examples 4, 5, and 6 also included the buffer component 14 of the electrode 210, though the disk of absorbent material of the component 14 in these Comparative Examples was made of the polyester fleece that was used to form the buffer component 14 in Example 3, rather than the Foamex PREMIUM polyurethane foam that was used to form the buffer component 14 in Examples 2, 4, and 5. The dimensions of the polyester disk that was used in forming the component 14 were the same in Comparative Examples 4, 5, and 6 as in Example 3. The wicking layer 212 held the component 14 in place between the wicking layer 212 and the conductive component 16. The component 12 was not included in the electrode of Comparative Examples 4, 5, and 6.

Another difference in Comparative Examples 4, 5, and 6 was that the pH buffering agent was applied as a coating to the surface of the component 14 polyester disk that faced the conductive component 16. The pH buffering agent included about 50 weight % Amberlite® IRP-64 and about 50 weight % Amberlite® IRP-88. The coating of the pH buffering agent included 0.35±0.05 grams of the Amberlite® copolymer mixture. The coating of the Amberlite® copolymer mixture was placed as a substantially uniform thickness onto one side of the polyester disk so that the Amberlite® copolymer mixture was sandwiched between the conductive component 16 and the polyester disk.

The coating was prepared by mixing about 150 grams of the Amberlite® copolymer mixture with about one liter of deionized water to make an aqueous slurry of the Amberlite® copolymer mixture. The polyester disk was placed on an open wire conveyor and passed under a flowing stream of the aqueous slurry of Amberlite® copolymers so that the aqueous slurry accumulated on one side of the disk to a thickness of about 0.03 cm. The buffer-coated disk was then placed in an oven at a temperature of about 100° C. to evaporate the water contained in the coating. The buffer-coated disk was allowed to dry in the oven until the weight of the disk remained steady.

EXAMPLES 2–3 AND COMPARATIVE EXAMPLES 1–4

In these Examples and Comparative Examples, a solution with a pH of about 5 to about 7 of 0.4 weight % dexamethasone sodium phosphate in deionized water was prepared. The dexamethasone sodium phosphate solution contained a mixture of mono and di-valent anions that were formed by dissociation of dexamethasone sodium phosphate within a solution pH range of about 5 to about 7. The dexamethasone sodium phosphate solution was injected into the component 12, where the electrode of the particular Example or Comparative Example included the component 12, or into the component 14 where the electrode of the particular Example or Comparative Example did not include the component 12. Where the Example or Comparative Example included both the component 12 and the component 14, it is believed that the dexamethasone sodium phosphate solution was absorbed substantially uniformly into both the component 12 and the component 14. The amount of the dexamethasone sodium phosphate solution that was injected into the various electrodes of Examples 2–3 and Comparative Examples 1–4 varied between 2 cc and 4 cc, as seen in Table 4 below.

The electrode of the particular Example or Comparative Example was positioned in the cell 710 with the wicking layer 212 disposed against the mouse skin 726. The system 710 was then permitted to operate for a period of 40 minutes with a current of 4 amps in the negative polarity mode applied to the conductor 722. Since the effective delivery area of each electrode used in Examples 2–3 and Comparative Examples 1–4, proximate the mouse skin 726, was about 22 cm$^2$, the current density for each replicate of each of these Examples and Comparative Examples was about 0.18 mA/cm$^2$, as indicated in Table 4. At least 10 experimental replicates were conducted for each Example and Comparative Example, as can be seen in Table 4.

Figure 12:
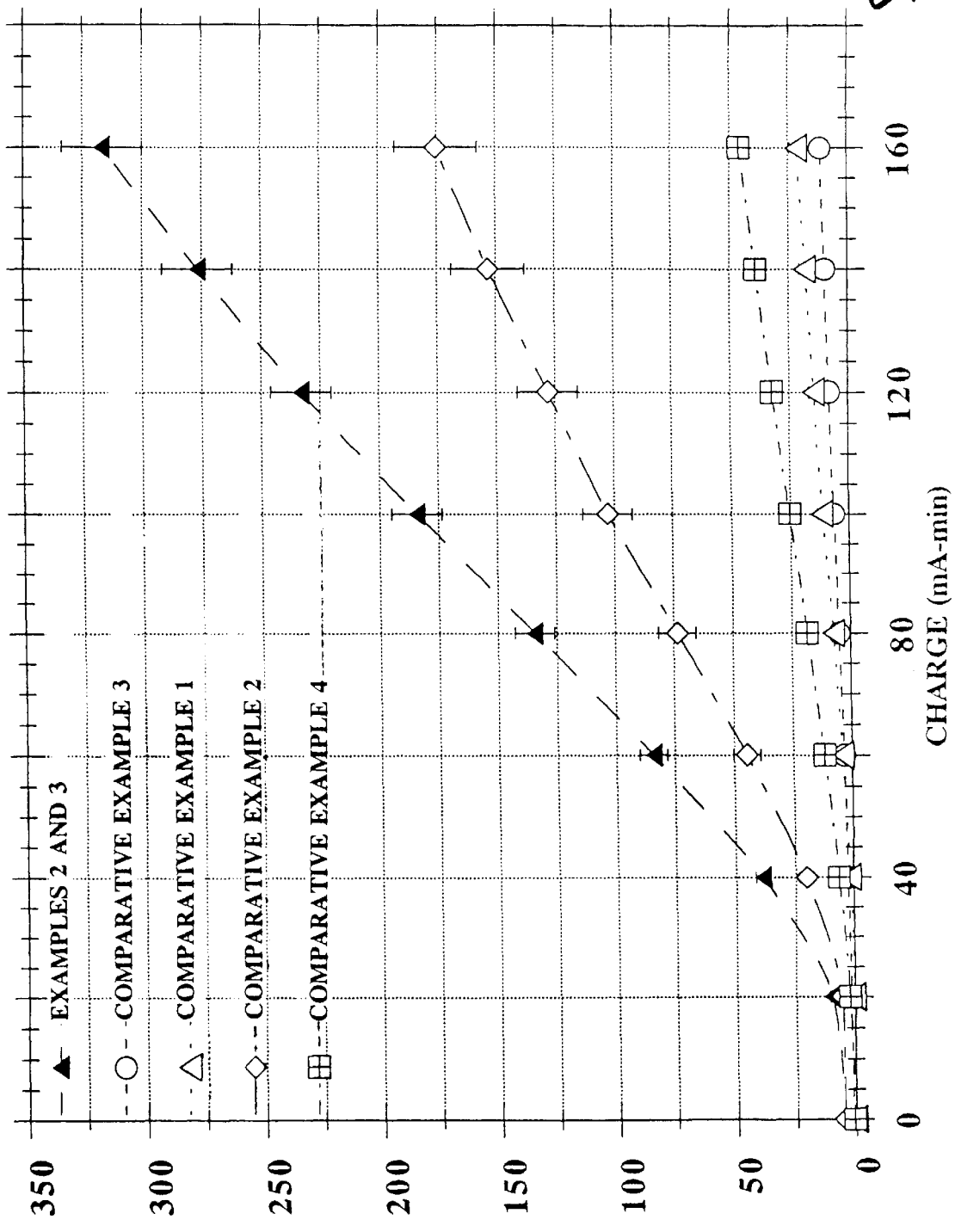
FIG. 12 is a graphical representation of the cumulative amount of dexamethasone phosphate delivered by various pH buffered electrodes versus the charge applied to the electrodes.

In FIG. 12, the cumulative amount of dexamethasone phosphate collected in the receptor compartment 712, as determined by HPLC, is plotted against the applied charge for Examples 2–3 and Comparative Examples 1–4. The mean amount of dexamethasone phosphate that accumulated in the receptor compartment 712 after a period of 40 minutes is numerically presented in Table 4 and is graphically visible in FIG. 12 for Examples 2–3 and Comparative Examples 1–4.

receptor compartment 712 was found to be about 10 minutes for each of the electrodes of Examples 2–3 and Comparative Examples 1–4.

The steady state fluxes of dexamethasone phosphate from the donor compartment 714 into the receptor compartment 712 for Examples 2–3 and Comparative Examples 1–4 are presented in Table 4. These results show that the electrodes of Examples 2 and 3 each exhibited an identical steady state flux of 25.7 $\mu$g/cm$^2$-hr for dexamethasone phosphate. These identical values for steady state flux demonstrate that the buffer component 14 of the inventive electrode performs in the same superior way, regardless of whether the pH buffering agent is applied to the absorbent material of the buffer component as part of the buffer coating, or is alternatively incorporated into the absorbent material of the buffer component 14 as part of the buffer suspension. On the other hand, the steady state flux of dexamethasone phosphate from the electrode of Comparative Example 1 was only 1.8 $\mu$g/cm$^2$-hr. This low steady state flux of Comparative

TABLE 4

| Aqueous Medicament Solution | Example 2 4 cc of 0.4% wt. Dexamethasone Sodium Phosphate | Example 3 4 cc of 0.4% wt. Dexamethasone Sodium Phosphate | Comparative Example 1 4 cc of 0.4% wt. Dexamethasone Sodium Phosphate | Comparative Example 2 3 cc of 0.4% wt. Dexamethasone Sodium Phosphate | Comparative Example 3 2 cc of 0.4% wt. Dexamethasone Sodium Phosphate | Comparative Example 4 3 cc of 0.4% wt. Dexamethasone Sodium Phosphate |
|---|---|---|---|---|---|---|
| Time of operation, min | 40 | 40 | 40 | 40 | 40 | 40 |
| Current (I), mA | 4 | 4 | 4 | 4 | 4 | 4 |
| Polarity | Negative | Negative | Negative | Negative | Negative | Negative |
| Effective Delivery Area (A), cm$^2$ | 22 | 22 | 22 | 22 | 22 | 22 |
| Current Density (i), mA/cm$^2$ | 0.18 | 0.18 | 0.18 | 0.18 | 0.18 | 0.18 |
| Mean amount of Medicament Delivered After 40 minutes, $\mu$g ± sd | 316.8 ± 108.0 | 294.0 ± 114.0 | 21.3 ± 11.4 | 175.3 ± 65.4 | 11.5 ± 5.8 | 46 ± 16.9 |
| Medicament Delivery Rate, $\mu$g/mA · min | 2.36 | 2.35 | 0.17 | 1.32 | 0.08 | 0.33 |
| Steady State Medicament Flux, $\mu$g/cm$^2$/hour | 25.7 | 25.7 | 1.8 | 14.4 | 0.84 | 3.6 |
| Number of Experimental Replicates | 40 | 10 | 15 | 15 | 30 | 40 |

The results in Table 4 and FIG. 12 demonstrate that the electrode 210 of the present invention, whether incorporating pH buffering agent within the component 14 or as the buffer coating of the component 14, delivered about 15 times more dexamethasone phosphate than the electrode of Comparative Example 1, where the positions of the components 12 and 14 were reversed. These results also demonstrate that the inventive electrode 210 delivered about 6 times more dexamethasone phosphate than the single fleece layer electrode of Comparative Example 4. These results demonstrate that the electrode of Comparative Example 3, which utilizes the same component 14 as the Example 2 electrode, but excludes the component 12 of the Example 2 electrode, exhibited the poorest delivery performance. This design of Comparative Example 3 delivered about 30 times less dexamethasone phosphate than the electrode 210 of Examples 2 and 3.

Figure 13:
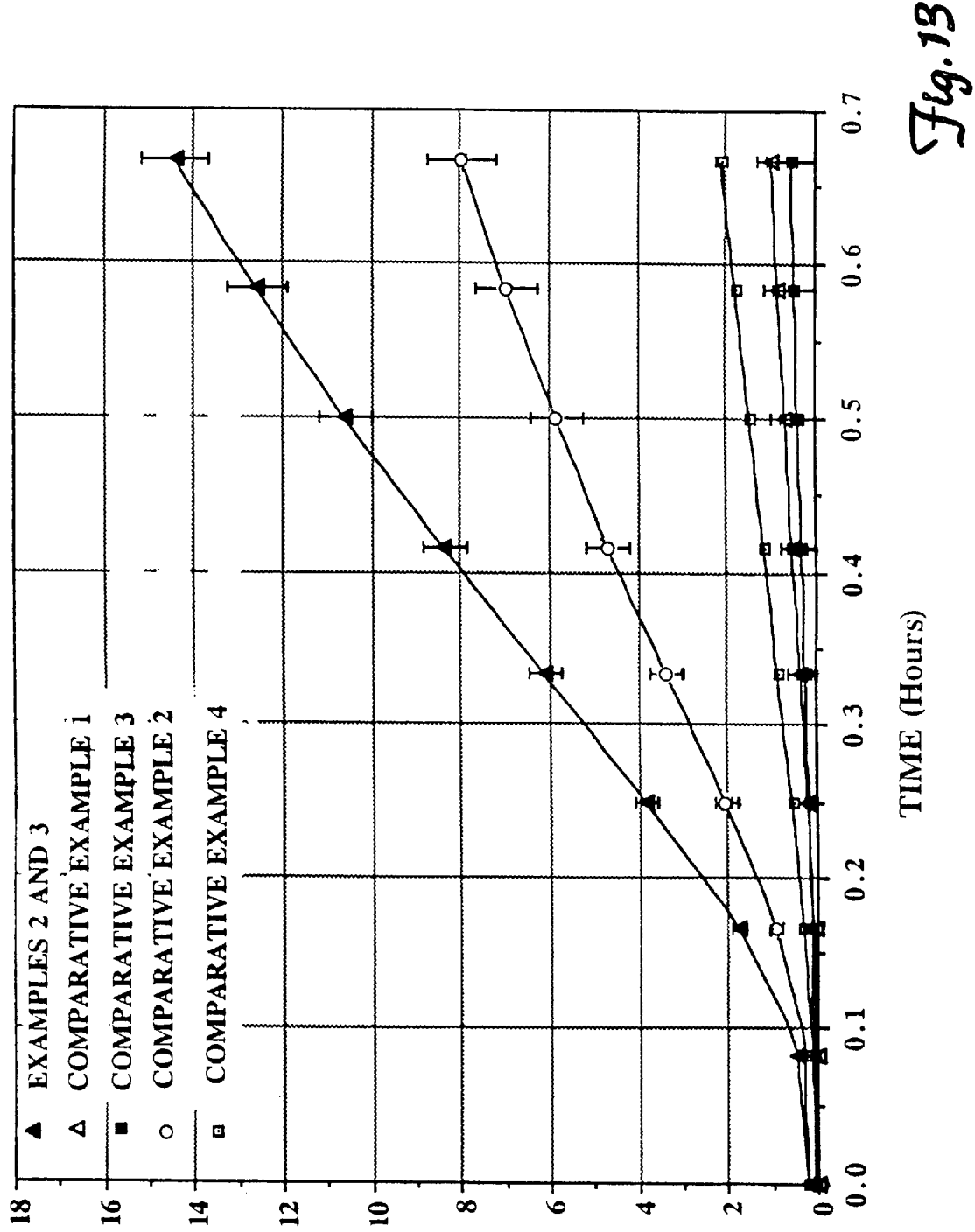
FIG. 13 is a graphical representation of the cumulative amount of dexamethasone phosphate delivered by various pH buffered electrodes, per unit effective delivery area of the electrodes, versus time of electrode operation.

The cumulative amount of dexamethasone phosphate delivered to the receptor compartment 712, per unit of effective delivery area for the electrodes of the particular Examples and Comparative Examples, are plotted in FIG. 13 as a function of time. The steady state flux of dexamethasone phosphate from the donor compartment 714 into the receptor compartment 712 was calculated as set forth above based on the slope of the linear portion of each plot of FIG. 13. The lag time for dexamethasone phosphate delivery into the Example 1, as compared to the high steady state fluxes of Examples 2 and 3, further demonstrates how positioning of the pH buffering agent with respect to the medicament delivery component 12 in accordance with the present invention is critical to attaining the surprising benefits of the present invention.

EXAMPLE 4 AND COMPARATIVE EXAMPLE 5

In this Example and Comparative Example, a solution with a pH of from about 4.0 to 5.5 of 4.0 weight % lidocaine hydrochloride in deionized water was prepared. The lidocaine hydrochloride solution contained a mixture of chloride ions and protonated lidocaine ions that were formed by dissociation of lidocaine hydrochloride in the solution. The lidocaine hydrochloride solution was injected into the component 12 in Example 4 and into the component 14 in Comparative Example 5. It is believed that the lidocaine hydrochloride solution was absorbed substantially uniformly into both the component 12 and the component 14 in Example 4. The amount of the lidocaine hydrochloride solution that was injected into the electrode of Example 4 was 4 cc, and the amount of the lidocaine hydrochloride solution that was injected into the electrode of Comparative Example 5 was 3 cc, as seen in Table 5 below.

The electrodes of the Example and Comparative Example were positioned in the cell 710 with the wicking layer 212 disposed against the mouse skin 726. The system 710 was then permitted to operate for a period of 40 minutes with a current of 4 amps in the positive polarity mode applied to the conductor 722. Since the effective delivery area of the electrodes used in Example 4 and Comparative Example 5, proximate the mouse skin 726, was about 22 cm$^2$, the current density for each replicate of each Example and Comparative Example was about 0.18 mA/cm$^2$, as indicated in Table 5. At least 15 experimental replicates were conducted for each Example and Comparative Example, as shown in Table 5.

TABLE 5

| Aqueous Medicament Solution | Comparative Example 5<br>3 cc of 4.0% wt.<br>Lidocaine<br>Hydrochloride | Example 4<br>4 cc of 4.0% wt.<br>Lidocaine<br>Hydrochloride |
|---|---|---|
| Time of Operation, min | 40 | 40 |
| Current (I), mA | 4 | 4 |
| Polarity | Positive | Positive |
| Effective Delivery Area (A), cm$^2$ | 22 | 22 |
| Current Density (i), mA/cm$^2$ | 0.18 | 0.18 |
| Mean amount of Medicament Delivered After 40 minutes, μg ± sd | 500.8 ± 139.1 | 1028.0 ± 202.4 |
| Medicament Delivery Rate, μg/mA.min | 3.7 | 7.2 |
| Steady State Medicament Flux, μg/cm$^2$/hour | 40.4 | 79.0 |
| Number of Experimental Replicates | 15 | 25 |

Figure 14:
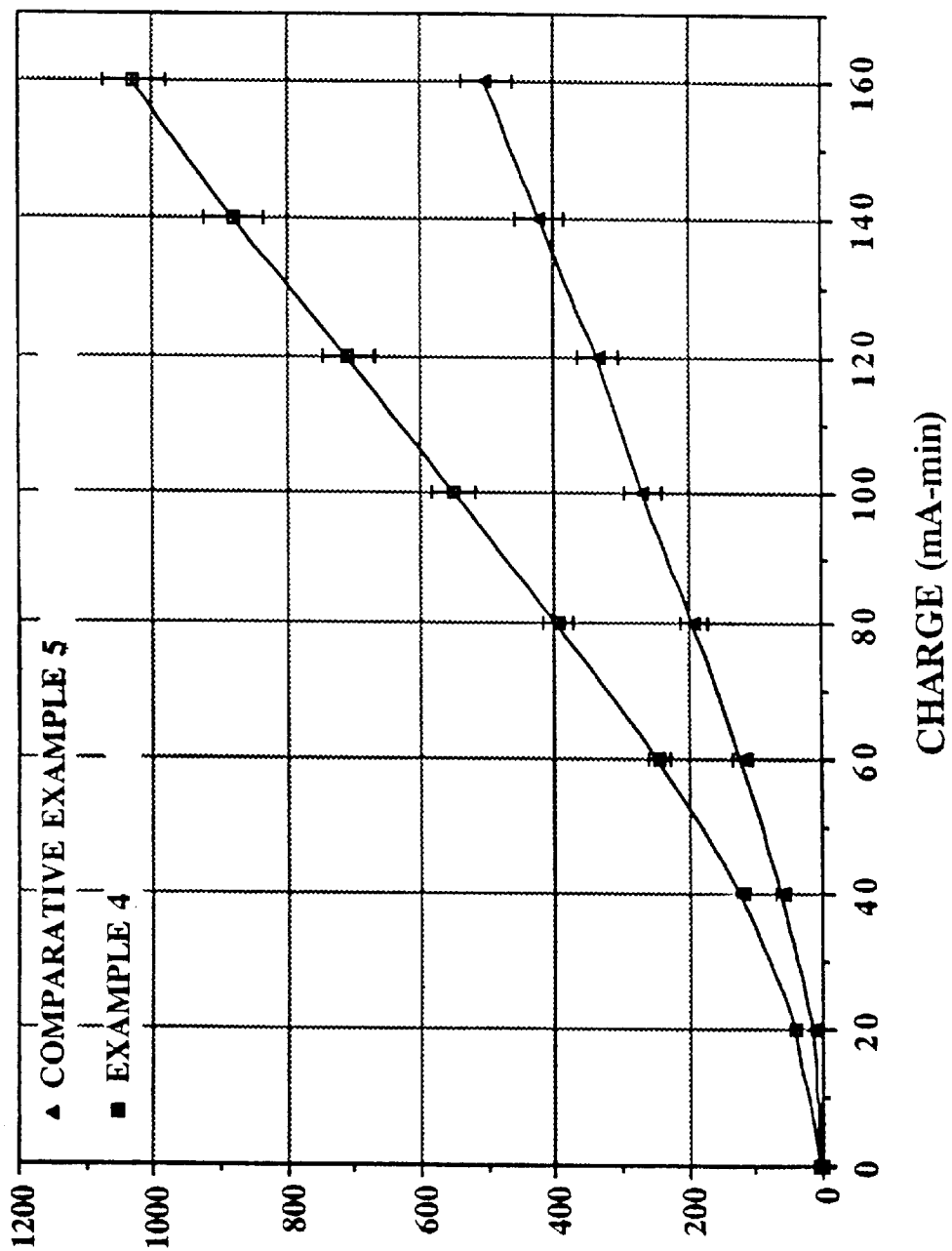
FIG. 14 is a graphical representation of the cumulative amount of protonated lidocaine delivered by various pH buffered electrodes versus the charge applied to the electrodes.

The cumulative amount of protonated lidocaine collected in the receptor compartment 712, as determined by HPLC, is plotted against the applied charge in FIG. 14 for Example 4 and Comparative Example 5. The mean amount of protonated lidocaine that accumulated in the receptor compartment 712 after a period of 40 minutes is numerically presented in Table 5 and is graphically visible in FIG. 14 for Example 4 and Comparative Example 5. These results in Table 5 and FIG. 14 demonstrate that the electrode 210 of the present invention delivered about 2 times more protonated lidocaine than the single fleece layer electrode of Comparative Example 5.

Figure 15:
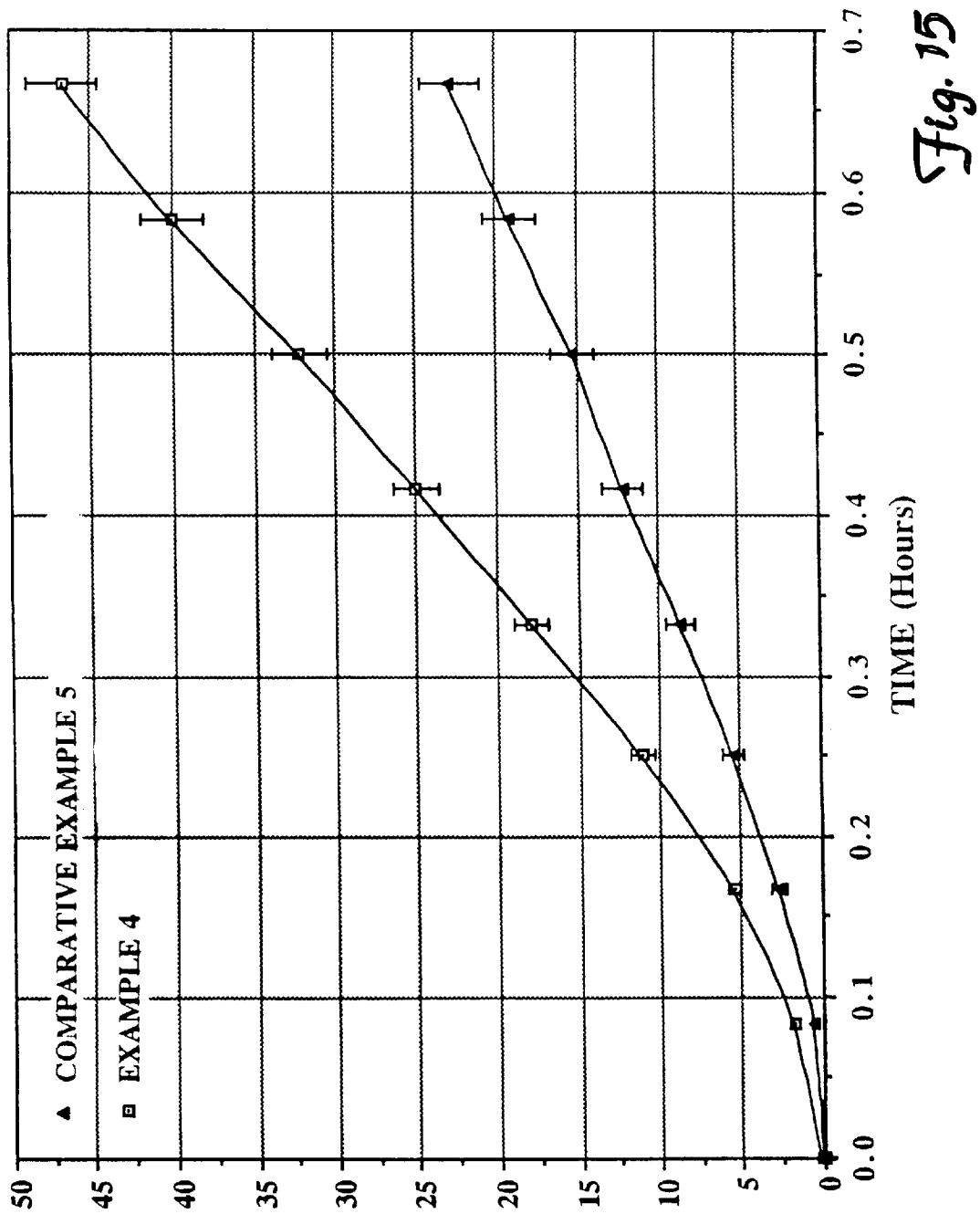
FIG. 15 is a graphical representation of the cumulative amount of protonated lidocaine delivered by various pH buffered electrodes, per unit effective delivery area of the electrodes, versus time of electrode operation.

The cumulative amount of protonated lidocaine delivered to the receptor compartment 712, per unit of effective delivery area of the electrodes of Example 4 and Comparative Example 5, are plotted in FIG. 15 as a function of time. The steady state flux of protonated lidocaine from the donor compartment 714 into the receptor compartment 712 was calculated as set forth above based on the slope of the linear portion of each plot of FIG. 15. The lag time for protonated lidocaine delivery into the receptor compartment 712 was found to be about 10 minutes for the electrodes of Example 4 and Comparative Example 5.

The steady state fluxes of protonated lidocaine from the donor compartment 714 into the receptor compartment 712 for Example 4 and Comparative Example 5 are presented in Table 5. These results demonstrate that the steady state flux of the protonated lidocaine from the electrode of Example 4 was 79.0 μg/cm$^2$-hr, whereas the steady state flux of the protonated lidocaine from the electrode of Comparative Example 5 was only 40.4 μg/cm$^2$-hr.

EXAMPLE 5 AND COMPARATIVE EXAMPLE 6

In this Example and Comparative Example, a solution of 0.5 weight % minoxidil tartrate in deionized water was prepared. The minoxidil tartrate solution contained a mixture of minoxidil ions and tartrate ions that were formed by dissociation of minoxidil tartrate in the solution. The minoxidil tartrate solution was injected into the component 12 in Example 5 and into the component 14 in Comparative Example 6. It is believed that the minoxidil tartrate solution was absorbed substantially uniformly into both the component 12 and the component 14 in Example 5. The amount of the minoxidil tartrate solution that was injected into the electrode of Example 5 was 4 cc, and the amount of the minoxidil tartrate solution that was injected into the electrode of Comparative Example 6 was 3 cc, as seen in Table 6 below.

The electrodes of the Example and Comparative Example were positioned in the cell 710 with the wicking layer 212 disposed against the mouse skin 726. The system 710 was then permitted to operate for a period of 40 minutes with a current of 4 amps in the positive polarity mode applied to the conductor 722. Since the effective delivery area of the electrodes used in Example 5 and Comparative Example 6, proximate the mouse skin 726, was about 22 cm$^2$, the current density for each replicate of each Example and Comparative Example was about 0.18 mA/cm$^2$, as indicated in Table 6. At least 15 experimental replicates were conducted for each Example and Comparative Example, as shown in Table 6.

TABLE 6

| Aqueous Medicament Solution | Comparative Example 6<br>3 cc of 0.5% wt.<br>Minoxidil<br>Tartrate | Example 5<br>4 cc of 0.5% wt.<br>Minoxidil<br>Tartrate |
|---|---|---|
| Time of operation (t), min | 40 | 5–30 |
| Current (I), mA | 4 | 4 |
| Polarity | Positive | Positive |
| Effective Delivery Area, cm$^2$ | 22 | 22 |
| Current Density (i), mA/cm$^2$ | 0.18 | 0.18 |
| Mean amount of Medicament Delivered After 40 minutes, μg ± sd | 19.6 ± 7.5 | 99.7.6 ± 29.8 |
| Medicament Delivery Rate, μg/mA.min | 0.13 | 0.75 |
| Steady State Medicament Flux, μg/cm$^2$/hour | 1.4 | 8.1 |
| Number of Experimental Replicates | 16 | 17 |

Figure 16:
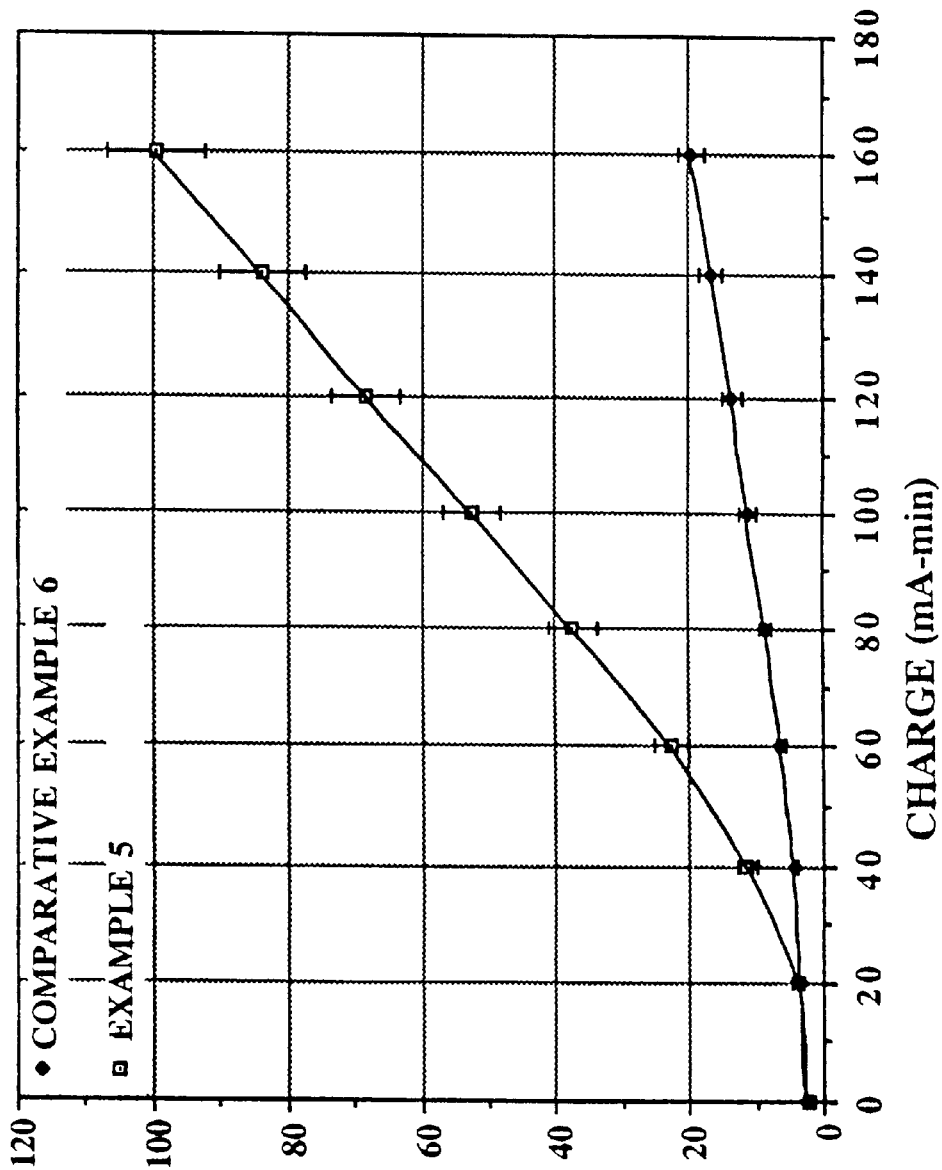
FIG. 16 is a graphical representation of the cumulative amount of minoxidil ions delivered by various pH buffered electrodes versus the charge applied to the electrodes.

The cumulative amount of minoxidil ions collected in the receptor compartment 712, as determined by HPLC, is plotted against the applied charge in FIG. 16 for Example 5 and Comparative Example 6. The mean amount of minoxidil ions that accumulated in the receptor compartment 712 after a period of 40 minutes is numerically presented in Table 6 and is graphically visible in FIG. 16 for Example 5 and Comparative Example 6. These results in Table 6 and FIG. 16 demonstrate that the electrode 210 of the present invention delivered about five times more minoxidil ions than the single foam layer electrode of Comparative Example 6.

Figure 17:
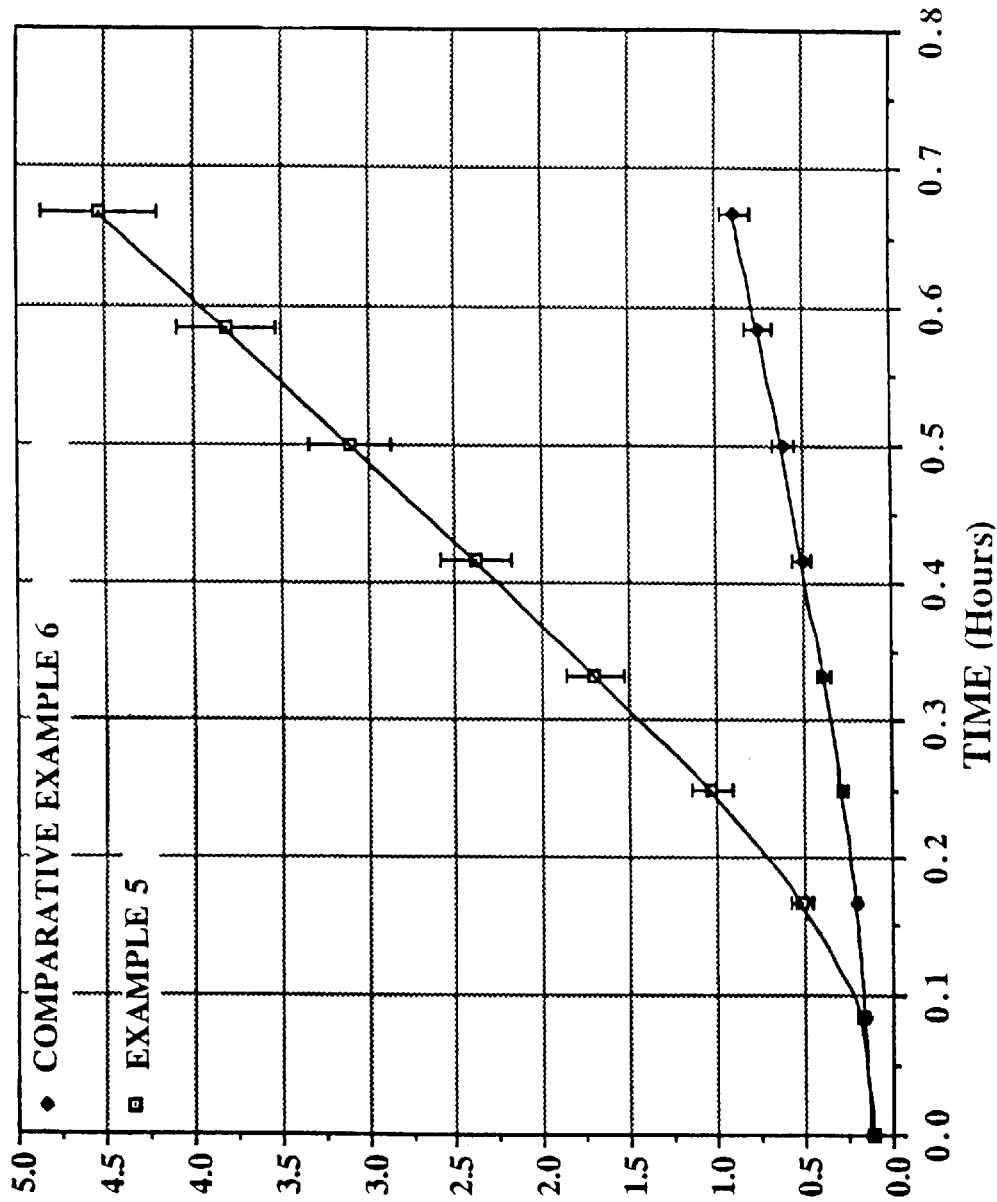
FIG. 17 is a graphical representation of the cumulative amount of minoxidil ions delivered by various pH buffered electrodes, per unit effective delivery area of the electrodes, versus time of electrode operation.

The cumulative amount of minoxidil ion delivered to the receptor compartment 712, per unit of effective delivery area of the electrodes of Example 5 and Comparative Example 6, are plotted in FIG. 17 as a function of time. The steady state flux of minoxidil ions from the donor compartment 714 into the receptor compartment 712 was calculated as set forth above based on the slope of the linear portion of each plot of FIG. 17. The lag time for minoxidil ions delivery into the receptor compartment 712 was found to be about 10 minutes for the electrodes of Example 5 and Comparative Example 6.

The steady state fluxes of minoxidil ions from the donor compartment 714 into the receptor compartment 712 for Example 5 and Comparative Example 6 are presented in Table 6. These results demonstrate that the steady state flux of the minoxidil ions from the electrode of Example 5 was 8.1 μg/cm²-hr, whereas the steady state flux of the minoxidil ions from the electrode of Comparative Example 6 was only 1.4 μg/cm²-hr.

Although the present invention has been described with reference to preferred embodiments, workers skilled in the art will recognize that changes may be made in form and detail without departing from the spirit and scope of the invention.

What is claimed is:

1. An iontophoresis electrode comprising:
   a buffer component, the buffer component comprising:
      a first absorbent material; and
      a pH buffering agent heterogeneously dispersed and substantially entrapped within the first absorbent material;
   a component for delivering medicament to a body, the medicament delivery component located adjacent to and in contact with the buffer component and the medicament delivery component comprising a second absorbent material; and
   an electrical connection in electrical communication with the buffer component.

2. The electrode of claim 1 wherein the pH buffering agent comprises one or more different ion-exchange functional groups that are selected from the group consisting of a carboxyl group, an amino group, a —SO$_3$H group, and an —OPO$_3$H$_2$ group.

3. The electrode of claim 1 wherein the buffer component further comprises a carrier for dispersing the pH buffering agent within the first absorbent material.

4. The electrode of claim 3 wherein the carrier is selected from the group consisting of glycerine, a solution of polyvinyl alcohol, a solution of polyethylene glycol, a solution of polyethylene oxide, a solution of a peptide-based gelatin, a solution of a plant-based gum, a dispersant, and a mixture of any of these.

5. The electrode of claim 1 wherein the first absorbent material and the second absorbent material are selected from the group consisting of a resinous material, a fibrous material, a colloidal material and a mixture of any of these.

6. The electrode of claim 5 wherein:
   the resinous material is selected from the group consisting of polyurethane, polyvinylpyrrolidone, polyvinyl alcohol, polyethylene oxide, polyacrylic acid, polyethylene glycol, polyacrylamide, and a cellulose derivative; and
   the fibrous material is selected from the group consisting of polyester, rayon, cotton, and wool.

7. The electrode of claim 1 wherein the first absorbent material, the second absorbent material, or both the first absorbent material and the second absorbent material comprise an absorption aid.

8. The electrode of claim 7 wherein the absorption aid is selected from the group consisting of glycerine, a solution of polyethylene glycol, a solution of polyethylene oxide, a solution of polyvinyl alcohol, a primary alcohol ethoxylate, a secondary alcohol ethoxylate, a polyoxypropylene-polyoxyethylene block copolymer, and a mixture of any of these.

9. The electrode of claim 1, the electrode further comprising conductive filler dispersed within the first absorbent material, the conductive filler capable of making the buffer component electrically conductive.

10. The electrode of claim 1, the electrode further comprising a distinct interface between the medicament delivery component and the buffer component, the medicament delivery component located adjacent to and in contact with the buffer component at the distinct interface, the distinct interface being present during the life of the electrode.

11. The electrode of claim 10 wherein the distinct interface prevents the first absorbent material from merging with the second absorbent material during the life of the electrode.

12. The electrode of claim 1 wherein the first absorbent material is capable of absorbing at least about 500 milliliters of electrolytic solution per square meter of first absorbent material surface area within about 5 seconds or less and the second absorbent material is capable of absorbing at least about 500 milliliters of electrolytic solution per square meter of second absorbent material surface area within about 5 seconds or less.

13. The electrode of claim 1 wherein the first absorbent material is capable of absorbing at least about 2000 milliliters of electrolytic solution per square meter of first absorbent material surface area within about 5 seconds or less and the second absorbent material is capable of absorbing at least about 2000 milliliters of electrolytic solution per square meter of second absorbent material surface area within about 5 seconds or less.

14. The electrode of claim 1 wherein the first absorbent material is capable of absorbing at least about 0.5 milliliters of electrolytic solution per gram of the first absorbent material within about 3 minutes or less and the second absorbent material is capable of absorbing at least about 0.5 milliliters of electrolytic solution per gram of the second absorbent material surface area within about 3 minutes or less.

15. The electrode of claim 1 wherein the first absorbent material is capable of absorbing at least about 1.0 milliliters of electrolytic solution per gram of the first absorbent material within about 3 minutes or less and the second absorbent material is capable of absorbing at least about 1.0 milliliters of electrolytic solution per gram of the second absorbent material surface area within about 3 minutes or less.

16. The iontophoresis electrode of claim 1 wherein the pH buffering agent comprises ion exchange resin, the ion exchange resin dispersed within the first absorbent material.

17. The iontophoresis electrode of claim 1 wherein the medicament delivery component is capable of supporting medicament delivery to the body without passage of medicament through the buffer component.

18. The iontophoresis electrode of claim 1 wherein the medicament delivery component is capable of being placed in contact with the body.

19. The iontophoresis electrode of claim 1 wherein the buffer component is located between the medicament delivery component and the electrical connection.

20. An iontophoresis electrode comprising:
   a medicament reservoir that is capable of containing electrolytic solution;
   a buffer component located in working relation with the medicament reservoir, the buffer component comprising:
      an absorbent material; and
      a pH buffering agent heterogeneously dispersed within or coated upon the absorbent material;
   an electrical connection in working relation with the medicament reservoir; and
   wherein the electrode is capable of delivering dexamethasone phosphate to a patient's body at a steady state flux of at least about 26 µg/cm²/hour when a current of about −4 mA is applied to the electrical connection, while maintaining the pH of the electrolytic solution in the range of about 4 to about 8.

21. An iontophoresis electrode comprising:
a buffer component, the buffer component comprising: open cell polyurethane foam; and
a pH buffering agent dispersed within the foam;
a component for delivering medicament, the medicament delivery component located adjacent to and in contact with the buffer component and the medicament delivery component comprising open cell polyurethane foam; and
an electrical connection in electrical communication with the buffer component.

22. The electrode of claim 21 wherein the buffer component further comprises glycerine, polyvinyl alcohol, polyethylene glycol, polyethylene oxide, a peptide-based gelatin, a plant-based gum, a dispersant, or a mixture of any of these for dispersing the pH buffering agent within the first absorbent material.

23. The electrode of claim 21 wherein the open cell polyurethane foam of the buffer component has:
an average pore density in the range of about 70 to about 80 pores per linear inch of polyurethane foam surface; and
an average pore size in the range of approximately 200 to approximately 240 micrometers.

24. The electrode of claim 21 wherein the open cell polyurethane foam of the medicament delivery component has:
an average pore density in the range of about 5 to about 200 pores per linear inch of polyurethane foam surface; and
an average pore size ranging from approximately 150 to approximately 1000 micrometers.

25. The iontophoresis electrode of claim 21 wherein the buffer component is located between the medicament delivery component and the electrical connection.

26. An iontophoresis electrode comprising:
a buffer component, the buffer component comprising:
a first absorbent material; and
a pH buffering agent coated on the first absorbent material;
a component for delivering medicament to a body, the medicament delivery component located adjacent to the buffer component, the medicament delivery component comprising a second absorbent material, and the medicament delivery component separated from the pH buffering agent by the first absorbent material of the buffer component;
an electrical connection in electrical communication with the buffer component.

27. The iontophoresis electrode of claim 26 wherein
the first absorbent material has at least a first surface and a second surface, the first surface and the second surface located on opposing sides of the first absorbent material;
the pH buffering agent is coated upon the first surface of the first absorbent material; and
the medicament delivery component is located adjacent to the second surface of the first absorbent material.

28. The iontophoresis electrode of claim 26 wherein the pH buffering agent comprises ion exchange resin, the ion exchange resin coated on the first absorbent material.

29. The electrode of claim 26 wherein the pH buffering agent comprises one or more different ion-exchange functional groups that are selected from the group consisting of a carboxyl group, an amino group, a —$SO_3H$ group, and an —$OPO_3H_2$ group.

30. The electrode of claim 26 wherein the first absorbent material and the second absorbent material are selected from the group consisting of a resinous material, a fibrous material, a colloidal material and a mixture of any of these.

31. The electrode of claim 30 wherein:
the resinous material is selected from the group consisting of polyurethane, polyvinylpyrrolidone, polyvinyl alcohol, polyethylene oxide, polyacrylic acid, polyethylene glycol, polyacrylamide, and a cellulose derivative; and
the fibrous material is selected from the group consisting of polyester, rayon, cotton, and wool.

32. The electrode of claim 26, the electrode further comprising a distinct interface between the medicament delivery component and the buffer component, the medicament delivery component located adjacent to and in contact with the buffer component at the distinct interface, the distinct interface being present during the life of the electrode.

33. The electrode of claim 32 wherein the distinct interface prevents the first absorbent material from merging with the second absorbent material during the life of the electrode.

34. The electrode of claim 26 wherein the first absorbent material is capable of absorbing at least about 500 milliliters of electrolytic solution per square meter of first absorbent material surface area within about 5 seconds or less and the second absorbent material is capable of absorbing at least about 500 milliliters of electrolytic solution per square meter of second absorbent material surface area within about 5 seconds or less.

35. The electrode of claim 26 wherein the first absorbent material is capable of absorbing at least about 2000 milliliters of electrolytic solution per square meter of first absorbent material surface area within about 5 seconds or less and the second absorbent material is capable of absorbing at least about 2000 milliliters of electrolytic solution per square meter of second absorbent material surface area within about 5 seconds or less.

36. The electrode of claim 26 wherein the first absorbent material is capable of absorbing at least about 0.5 milliliters of electrolytic solution per gram of the first absorbent material within about 3 minutes or less and the second absorbent material is capable of absorbing at least about 0.5 milliliters of electrolytic solution per gram of the second absorbent material surface area within about 3 minutes or less.

37. The electrode of claim 26 wherein the first absorbent material is capable of absorbing at least about 1.0 milliliters of electrolytic solution per gram of the first absorbent material within about 3 minutes or less and the second absorbent material is capable of absorbing at least about 1.0 milliliters of electrolytic solution per gram of the second absorbent material surface area within about 3 minutes or less.

* * * * *